(12) United States Patent
Du et al.

(10) Patent No.: US 10,004,766 B2
(45) Date of Patent: Jun. 26, 2018

(54) TRABECULAR MESHWORK STEM CELLS

(71) Applicant: University of Pittsburgh—of the Commonwealth System of Higher Education, Pittsburgh, PA (US)

(72) Inventors: Yiqin Du, Pittsburgh, PA (US); James L. Funderburgh, Pittsburgh, PA (US); Joel Steven Schuman, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 20 days.

(21) Appl. No.: 14/605,216

(22) Filed: Jan. 26, 2015

(65) Prior Publication Data

US 2015/0231180 A1 Aug. 20, 2015

Related U.S. Application Data

(62) Division of application No. 13/361,908, filed on Jan. 30, 2012, now abandoned.

(60) Provisional application No. 61/462,255, filed on Jan. 31, 2011, provisional application No. 61/438,163, filed on Jan. 31, 2011.

(51) Int. Cl.
*A61K 35/30* (2015.01)
*A61K 9/00* (2006.01)

(52) U.S. Cl.
CPC ............ *A61K 35/30* (2013.01); *A61K 9/0048* (2013.01)

(58) Field of Classification Search
CPC .............................. A61K 35/30; A61K 9/0048
See application file for complete search history.

(56) References Cited

FOREIGN PATENT DOCUMENTS

WO    WO 2010130418 A2  * 11/2010    ........... A61K 9/0051

OTHER PUBLICATIONS

Tay et al., Identification and characterization of mesenchymal stem cells derived from the trabecular meshwork of the human eye. Stem Cells and Development, vol. 21, No. 9 (2012) pp. 1381-1390.*
Johnson et al., Neuroprotective effects of intravitreal mesenchymal stem cell transplantation in experimental glaucoma. Investigative Ophthalmology & Visual Science, vol. 51, No. 4 (Apr. 2010) pp. 2051-2059.*
Levin et al., Stem cell therapy for ocular disorders. Archives of Ophthalmology, vol. 122 (Apr. 2004) pp. 621-627.*
U.S. Appl. No. 13/361908 (Abandoned), filed Jan. 30, 2012 (Sep. 20, 2012).
U.S. Appl. No. 13/361,908, Mar. 10, 2015 Notice of Abandonment.
U.S. Appl. No. 13/361,908, Aug. 25, 2014 Non-Final Office Action.
U.S. Appl. No. 13/361,908, Feb. 11, 2014 Amendment and Request for Continued Examination (RCE).
U.S. Appl. No. 13/361,908, Dec. 11, 2013 Response to Final Office Action.
U.S. Appl. No. 13/361,908, Sep. 11, 2013 Final Office Action.
U.S. Appl. No. 13/361,908, Jun. 17, 2013 Response to Non-Final Office Action.
U.S. Appl. No. 13/361,908, Jan. 16, 2013 Non-Final Office Action.
U.S. Appl. No. 13/361,908, Dec. 21, 2012 Response to Restriction Requirement.
U.S. Appl. No. 13/361,908, Oct. 25, 2012 Restriction Requirement.
"Adult Stem Cells", edited by Kursad Turksen, Human Press Inc., Totowa, New Jersey, Table of Contents (2004)
"Stem Cells Handbook", edited by Stewart Sell, Human Press Inc., Totowa, New Jersey, Table of Contents (2004).
Alexander et al., "Expression of Matrix Metalloproteinases and Inhibitor by Human Trabecular Meshwork", Investigative Ophthalmology & Visual Science, 32(1):172-180 (1991).
Alvarado et al., "Trabecular meshwork cellularity in primary open-angle glaucoma and nonglaucomatous normals," Ophthalmology 91:564-579 (1984).
Alvarado et al., "Age-related changes in trabecular meshwork cellularity," Invest Ophthalmol Vis Sci 21:714-727 (1981).
Arsenijevic et al., "Isolation of Multipotent Neural Precursors Residing in the Cortex of the Adult Human Brain," Experimental Neurology, 170:48-62 (2001).
Beltrami et al., "Adult Cardiac Stem Cells Are Multipotent and Support Myocardial Regeneration," Cell, 114:763-776 (2003).
Bill A. Editorial: The drainage of aqueous humor. Invest Ophthalmol 1975; 14:1-3.
Buller et al., "Human trabecular meshwork phagocytosis. Observations in an organ culture system," Investigative Ophthalmology & Visual Science 31:2156-2163 (1990).
Camargo et al., "Hematopoietic Stem Cells do not Engraft with Absolute Efficiencies," Blood, 107:501-507 (2006).
Challa et al., "Gene expression profile in a novel cell type in primary cultures of human trabecuiar meshwork," Invest Ophtha!moi Vis Sci 44:E-Abstract 3164 (2003).
Clark et al., "Glucocorticoid-induced formation of cross-linked actin networks in cultured human trabecular meshwork cells," Investigative Ophthalmology & Visual Science, 35(1):281-294 (Jan. 1994).
Coles et al., "Facile Isolation and the Characterization of Human Retinal Stem Cells", PNAS, 101(44):15772-15777 (2004).
Collinson et al., "The roks of Pax6 in the cornea, retina, an<1 olfactory epithelium of the developing mouse embryo," Dev Biol. 255:303-312 (2003).
Daley et al., "Prospects for stem cell-based therapy," Cell, 132:544-548 (2008).

(Continued)

*Primary Examiner* — Kara Johnson
(74) *Attorney, Agent, or Firm* — Baker Botts L.L.P.

(57) ABSTRACT

Provided herein are isolated populations of multipotent stem cells capable of differentiating into trabecular meshwork (TM) cells, methods of obtaining an isolated population of TM cells, and isolated populations of TM cells obtained therefrom. Compositions, kits, and devices comprising the isolated populations of multipotent stem cells or TM cells are also provided herein. Further provided are methods of using the compositions, kits, and devices for decreasing intraocular pressure in an eye, increasing cell density in a trabecular meshwork of an eye, increasing outflow of aqueous humor from an eye, or treating or preventing a medical condition in a subject.

15 Claims, 20 Drawing Sheets

(56) References Cited

OTHER PUBLICATIONS

Ding et al., "ABCG2: A Potential Marker of Stem Cells and Novel Target in Stem Cell and Cancer Therapy," Life Sciences, 85:631-637 (2010).
Du et al., Multipotent stem cells from trabecular meshwork becomes phagocytic TM cells. Glaucoma, 53(3):1566-1575 (Mar. 2012).
Du et al., "Stem cell therapy restores transparency to defective murine corneas," Stem Cells 27:1635-1642 (2009).
Du et al., "Multipotent stem cells in human corneal stroma," Stem Cells 23:1266-1275 (2005).
Du et al., "Secretion and organization of a cornea-like tissue in vitro by stem cells from human corneal stroma," Invest Ophthalmol Vis Sci 48:5038-5045 (2007).
Du et al., "Stem cells from trabecular meshwork home to TM tissue in vivo," Invest Ophtahlmol Vis Sci., 54:1450-1459 (2013).
Eveleth, "Cell-based therapies for ocular disease", Journal of Ocular Pharmacology and Therapeutics, 29(10):844-854 (2013).
Fan et al., "Glaucoma: genes, phenotypes, and new directions for therapy," The Journal of Clinical Investigation, 120(9):3064-3072 (2010).
Funderburgh et al., "PAX6 expression identifies progenitor cells for corneal keratocytes," Faseb J, 19:1371-1373 (2005).
Gonzalez et al. "Characterization of free-floating spheres from human trabecular meshwork (HTM) cell culture in vitro," Exp Eye Res, 82:959N967 (2006).
Goodell et al., "Isolation and functional properties of murine hematopoietic stem cells that are replicating in vivo," J Exp Med 183:1797-180 (1996).
Goodell et al., "Stem Cell identification and Sorting Using the Hoechst 33342 Side Population (SP)," Current Protocols in Cytometry, Supplement 34:9.18.1-9.18.11 (2005).
Gregory-Evans et al., "Ex vivo gene therapy and vision," Current Gene Therapy, 12:103-115 (2012).
Gupta D. Glaucoma diagnosis and management: Lippincott Williams & Wilkins; 2004.
Halleux et al., "Multi-Lineage Potential of Human Mesenchymal Stem Cells Following Clonal Expansion," J. Musculoskel Neuron Interact, 2(1):71-76 (2001).
He et al., "Mitochondrial complex I defect induces ROS release and degeneration in trabecular meshwork cells of POAG patients: protection by antioxidants," Invest Ophthalmology & Visual Science, 49:1447-1458 (2008).
Jiang et al., "Pluripotency of Mesenchymal Stem Cells Derived from Adult Marrow," Nature, 418:41-49 (2002).
Johnson et al., "Trabecular meshwork recovery after phagocytic challenge," Curr Eye Res 8:1121-1130 (1989).
Jung et al., "Expression of MUC1 on Corneal Endothelium of Human," Cornea, 21(7):691-695 (2002).
Kelley et al., "Stem cells in the trabecular meshwork: present and future promises," Exp Eye Res 88:747-751 (2009).
Kim et al., "Human trabecular meshwork and ciliary body epithelial cells express MUC1 Mucin," Investigative Ophthalmology & Visual Science, 43:E-Abstract 2461 (2002).
Kim et al., "The Multidrug Resistance Transporter ABCG2 (Breast Cancer Resistance Protein 1) Effluxes Hoechst 33342 and Is Overexpressed in Hematopoietic Stem Cells," Clinical Cancer Research, 8:22-28 (2002).
Le et al., "Risk factors associated with the incidence of open-angle glaucoma: the visual impairment project," Invest. Ophthalmology & Visual Science 44:3783-3789 (2003).
Levkovitch-Verbin, "Animal models of optic nerve diseases," Eye, 18:1066-1074 (2004).
Liton et al., "Identification of genes differentially expressed by Chitinase 3-like 1 in human trabecular meshwork cells," Invest. Ophthalmology & Visual Science 50:4859 (2009).
Liton et al., "Genome-Wide Expression Profile of Human Trabecular Meshwork Cultured Cells, Nonglaucomatous and Primary Open Angle Glaucoma Tissue," Molecular Vision, 12:774-790 (2006).
Liu, "Keratocan-deficient mice display alterations in corneal structure," J Biol Chem 278:21672-21677 (2003).
Lutjen-Drecoll E., "Orphological changes in glaucomatous eyes and the role of TGFβ2 for the Pathogenesis of the Disease," Exp Eye Res 81:1-4 (2005).
Marchetti et al., "Steming vision loss with stem cells," The Journal of Clinical Investigation, 120(9):3012-3021 (2010).
Martin et al., "Persistent Expression of the ATP-Binding Cassette Transporter, Abcg2, Identifies Cardiac SP Cells in the Developing and Adult Heart," Developmental Biology, 265:262-275 (2004).
Matthew et al., "ABCG2-Mediated Dyecycle Violet Efflux Defined Side Population on Benign and Malignant Prostate," Cell Cycle, 8(7):1053-1061 (2009).
McGowan et al., "Stem cell markers in the human posterior limb us and corneal endothelium of unwounded and wounded corneas," Mol Vis 13:1984-2000 (2007).
McKenna et al., "Injection of Soluble Antigen into the Anterior Chamber of the Eye Induces Expansion and Functional Unresponsiveness of Antigen-Specific CD8+ T Cells," The Journal of Immunology, 169:5630-5637 (2002).
Mimura et al., "Replication competence and senescence in central and peripheral human corneal endothelium," Investigative Ophthalmology & Visual Science, 47:1387-1396 (2006).
Mukhopadhyay et al., "Mucins in the pathogenesis of breast cancer: implications in diagnosis, prognosis and therapy," Biochim Biophys Acta, 1815:224-240 (2011).
Nagai et al., "Multilineage potential of stable human mesenchymal stem cell line derived from fetal marrow," PLoS One 2:e1272 (2007).
Oshima et al., "Isolation of Sphere-Forming Stem Cells from the Mouse Inner Ear," Auditory and Vestibular Research: Methods and Protocols, 493:141-162 (2009).
Paez-Gonzalez et al., "Ank3-Dependent SVZ Niche Assembly is Required for the Continued Production of New Neurons," Neuron, 71:61-75 (2011).
Patel et al., "Multipotent menstrual blood stromal stem cells: isolation, characterization, and differentiation," Cell Transplant 17:303-311 (2008).
Pillai, "Stem cells for ocular tissue engineering and regeneration," Current Topics in Medicinal Chemistry, 11:1606-1620 (2011).
Recklies et al., "Inflammatory cytokines induce production of CHI3L1 by articular chondrocytes," J. Biol. Chem. 280:41213-41221 (2005).
Ruiz-Ederra et al., "Aquaporin-1-facilitated keratocyte migration in cell culture and in vivo corneal wound healing models," Exp Eye Res 89:159-165 (2009).
Sarkadi et al., "Evaluation of ABCG2 Expression in Human Embryonic Stem Cells: Crossing the Same River Twice?", Stem Cells, 28:174-176 (2010).
Scharenberg et al., "The ABCG2 Transporter is an Efficient Hoechst 33324 Efflux Pump and is Preferentially Expressed by Immature Human Hematopoietic Progenitors," Blood, 99:507-512 (2002).
Sivak et al., "Pax-6 Expression and Activity Are Induced in the Reepithelializing Cornea and Control Activity of the Transcriptional Promoter for Matrix Metalloproteinase Gelatinase B," Developmental Biology, 222:41-54 (2000).
Stamer et al., "Cultured human trabecular meshwork cells express aquaporin-1 water channels," Curr Eye Res 14:1095-1100 (1995).
Stamer et al., "Localization of aquaporin CHIP in the human eye: implications in the pathogenesis of glaucoma and other disordersof ocular fluid balance," Investigative Ophthalmology & Visual Science 35:3867-3872 (1994).
Steely et al., "The effects of dexamethasone on fibronectin expression in cultured human trabecular meshwork cells," Investigative Ophthalmology & Visual Science, 33(7):2242-2250 (1992).
Stone et al., "Identification of a Gene That Causes Primary Open Angle Glaucoma," Science, 275:668-670 (1997).
Swetha et al., "Treatment viability of stem cells in ophthalmology," Current Opinion in Ophthalmology, 21:213-217 (2010).
Tamm, "Myocilin and Glaucoma: Facts and Ideas," Progress in Retinal and Eye Research 21:395-428 (2002).

(56) References Cited

OTHER PUBLICATIONS

Tamm, "The trabecular meshwork outflow pathways: Structural and functional aspects," Experimental Eye Research, 88:648-655 (2009).

Tay et al., "Identification and characterization of mesenchymal stem cells derived from the trabecular meshwork of the human eye," Stem Cells and Development, 21(9):1381-1390 (2012).

Telford et al., "Side population analysis using a violet-excited cell-permeable DNA binding dye," Stem Cells 25:1029-1036 (2007).

Telford, "Applications of Flow Cytometry in Stem Cell Research and Tissue Regeneration", Edited by Krishan, et al., Wiley-Blackwell, A John Wiley & Sons, Inc. Chapter 3:25-44 (2010).

Tropepe et al., "Retinal Stem Cells in the Adult Mammalian Eye," Science, 287:2032-2036 (2000).

Verfaillie, "Adult stem cells: assessing the case for pluripotency," Trends Cell Biol 12:502-508 (2002).

Vittitow et al., "Genes expressed in the human trabecular meshwork during pressure-induced homeostatic response," J Cell Physiol. 201:126-137 (2004).

Wang et al., "Activation of a Tissue-Specific Stress Response in the Aqueous," Nature Medicine, 7(3):304-309 (2001).

Xue et al., "Presence of an established calcification marker in trabecular meshwork tissue of glaucoma donors," Investigative Ophthalmology & Visual Science 48:3184-3194 (2007).

Yin et al., "ABCG2 Expression and Side Population Abundance Regulated by a Transforming Growth Factor β-Directed Epithelial-Mesenchymal Transition," Cancer Research, 68(3):800-807 (2008).

Yoshida et al., "Isolation of Multipotent Neural Crest-Derived Stem Cells from the Adult Mouse Cornea," Stem Cells, 24:2714-2722 (2006).

Yu et al., "Progenitors for the corneal endothelium and trabecular meshwork: A potential source for personalized stem cell therapy in corneal endothelial diseases and glaucoma," Journal of Biomedicine and Biotechnology, 2011(Article IDS 412743):13 pages (2011).

Zhang et al., "Dexamethasone inhibition of trabecular meshwork cell phagocytosis and its modulation by glucocorticoid receptor beta," Exp. Eye Res 84:275-284 (2007).

Zhou et al., "Bcrp1 Gene Expression is Required for Normal Numbers of Side Population Stem Cells in Mice, and Confers Relative Protection to Mitozantrone in Hematopoietic Cells In Vivo," PNAS, 99(19):12339-12344 (2002).

Zhou et al., "The ABC Transporter Bcrp1/ABCG2 is Expressed in a Wide Variety of Stem Cells and is a Molecular Determinant of the Side-Population Phenotype," Nature Medicine, 7(9):1028-1034 (2001).

* cited by examiner

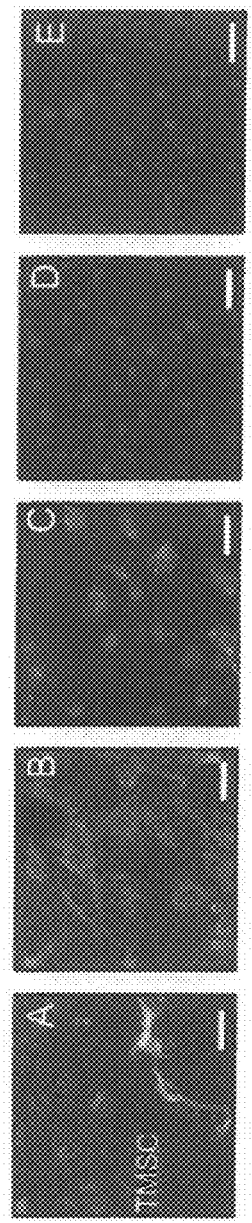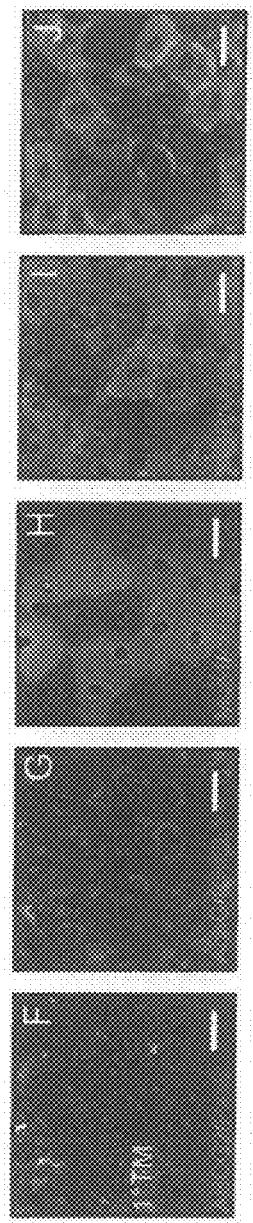

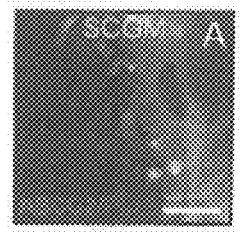 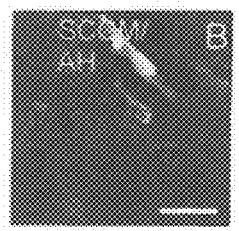 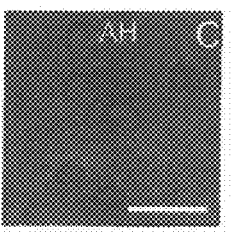 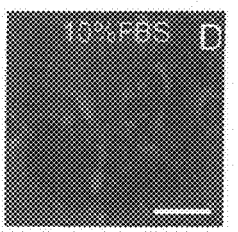
FIG. 4A  FIG. 4B  FIG. 4C  FIG. 4D
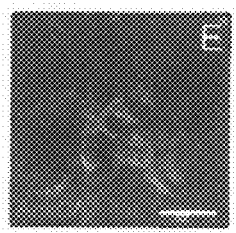 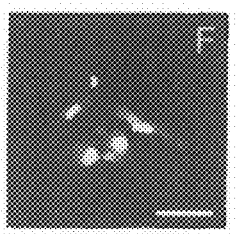 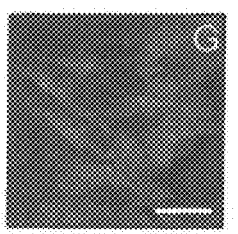 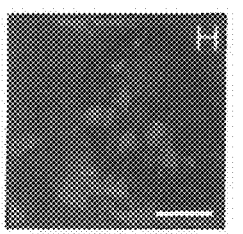
FIG. 4E  FIG. 4F  FIG. 4G  FIG. 4H
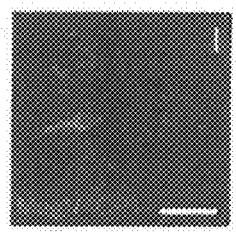 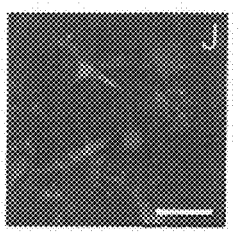 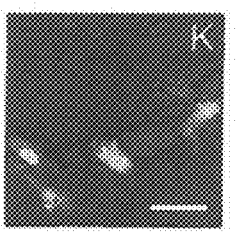 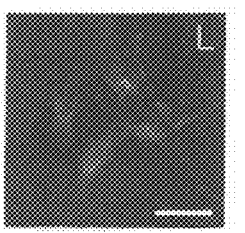
FIG. 4I  FIG. 4J  FIG. 4K  FIG. 4L
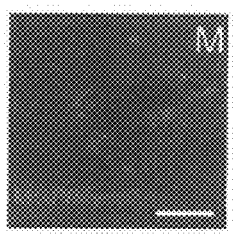 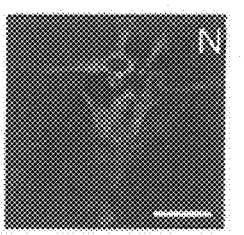 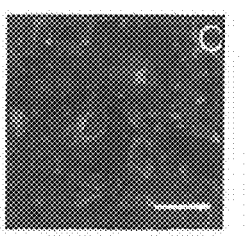 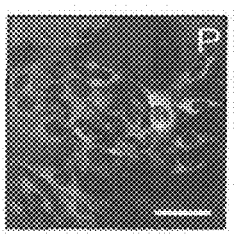
FIG. 4M  FIG. 4N  FIG. 4O  FIG. 4P
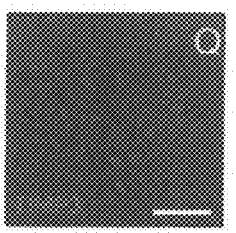 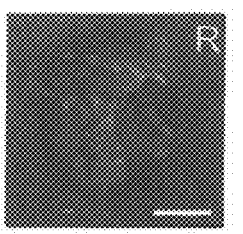 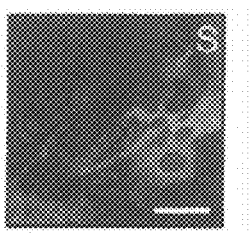 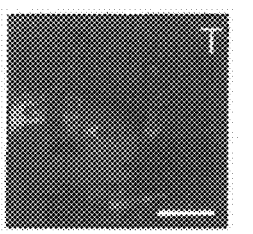
FIG. 4Q  FIG. 4R  FIG. 4S  FIG. 4T

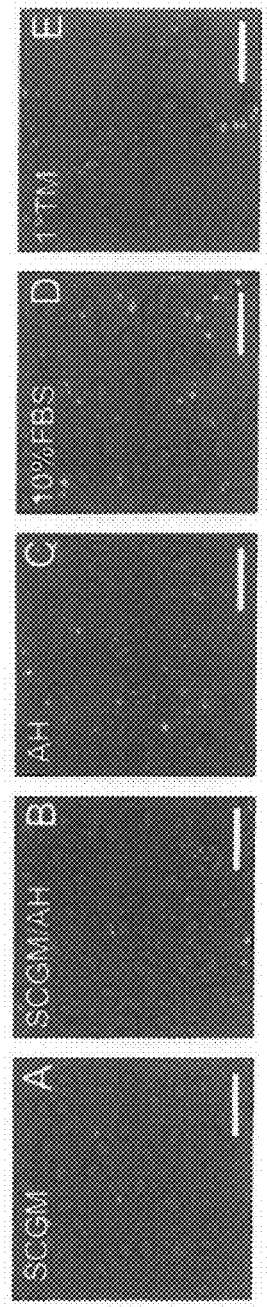
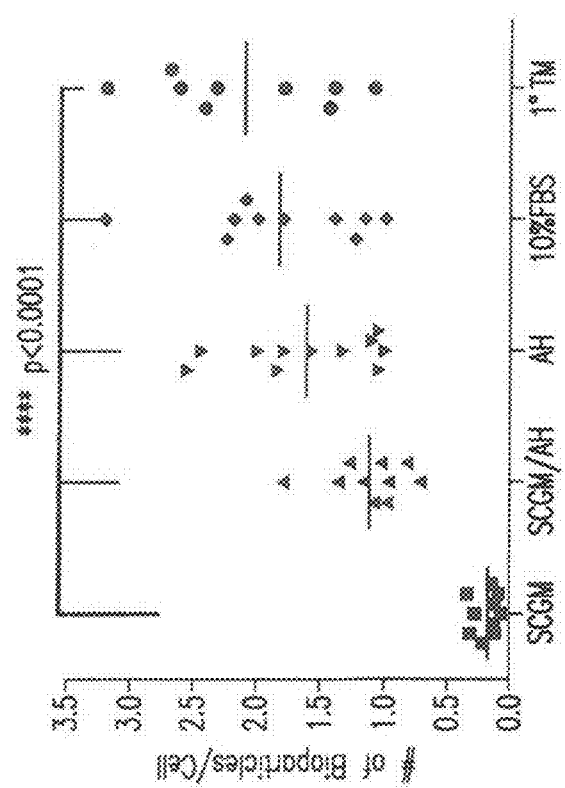

  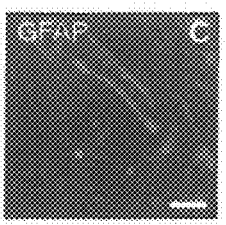 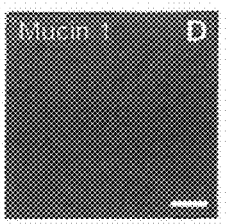
FIG. 6A  FIG. 6B  FIG. 6C  FIG. 6D
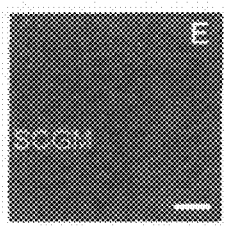 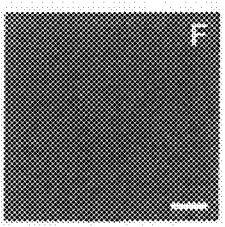 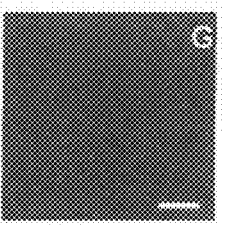 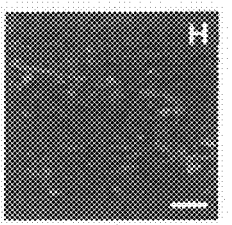
FIG. 6E  FIG. 6F  FIG. 6G  FIG. 6H
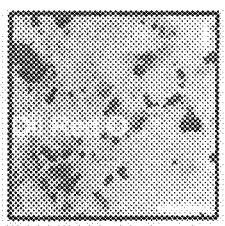 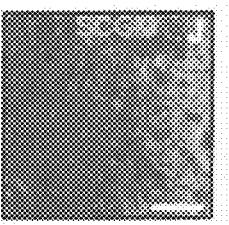 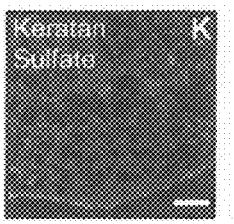 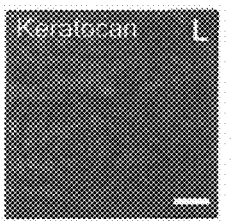
FIG. 6I  FIG. 6J  FIG. 6K  FIG. 6L
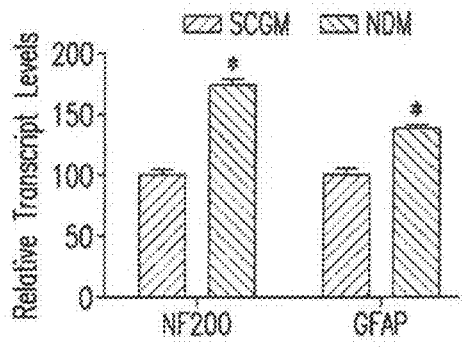 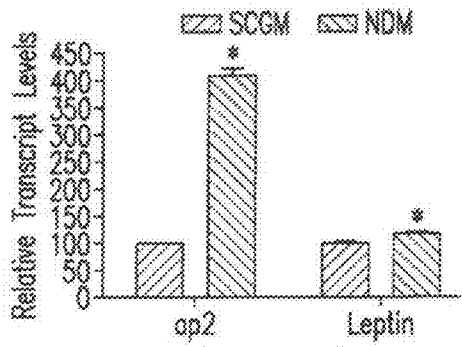
FIG. 6M  FIG. 6N

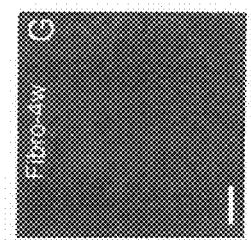
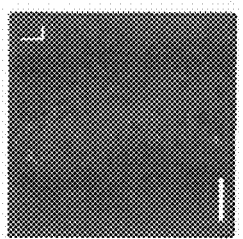
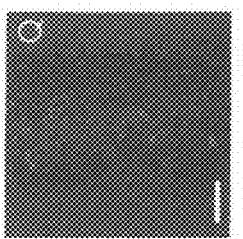
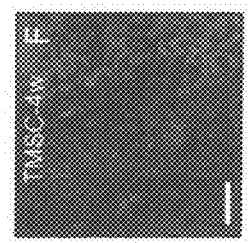
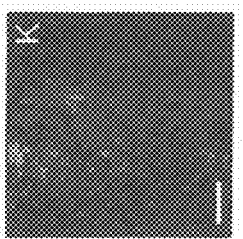
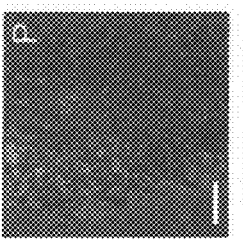
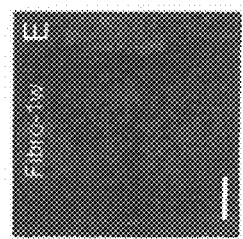
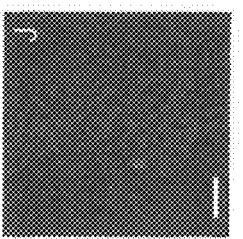
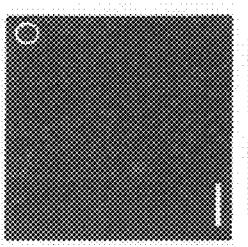
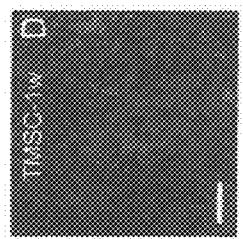
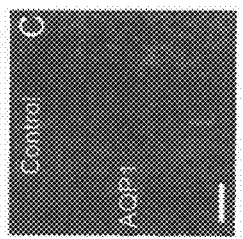

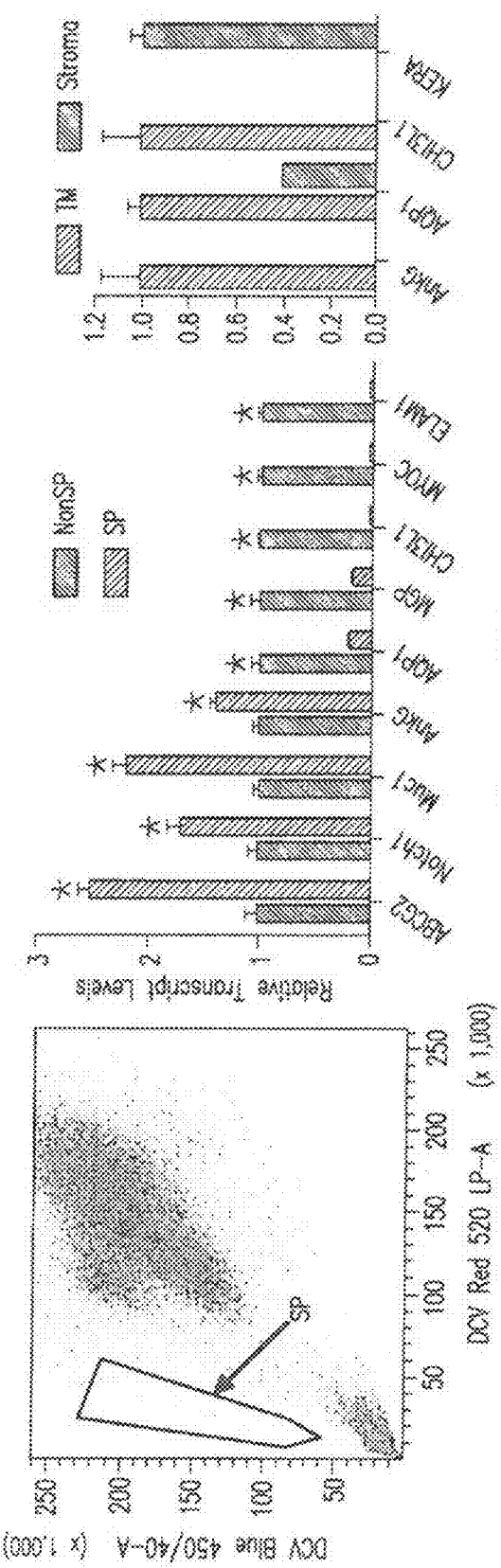

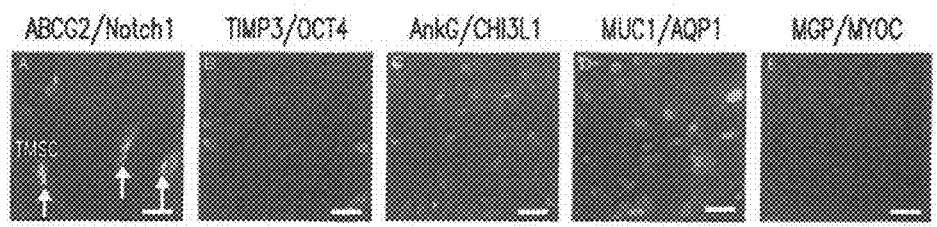
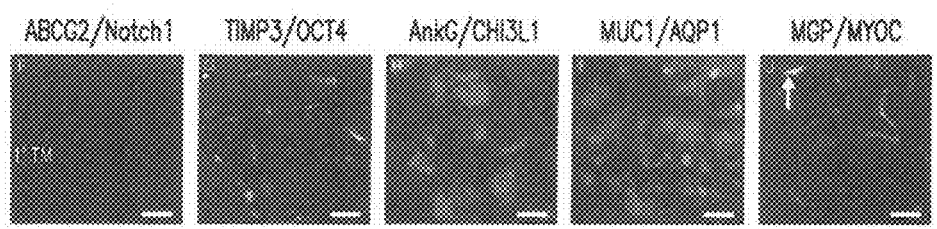
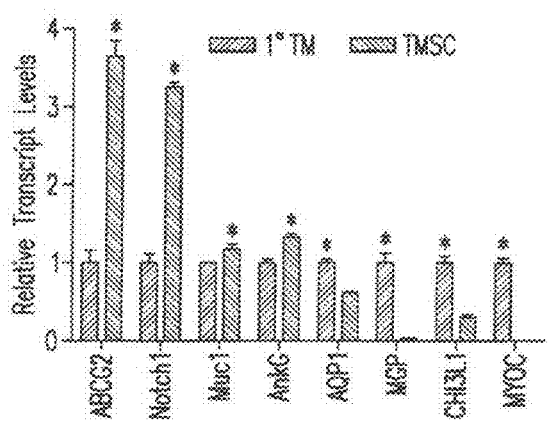
FIG. 9A FIG. 9B FIG. 9C FIG. 9D FIG. 9E
FIG. 9F FIG. 9G FIG. 9H FIG. 9I FIG. 9J
FIG. 9K

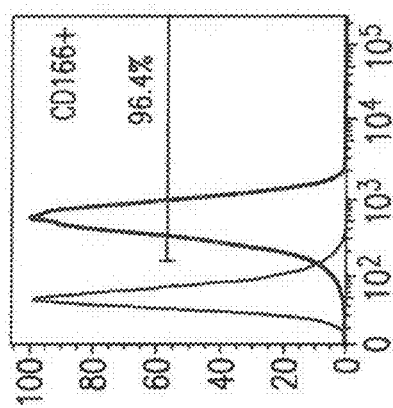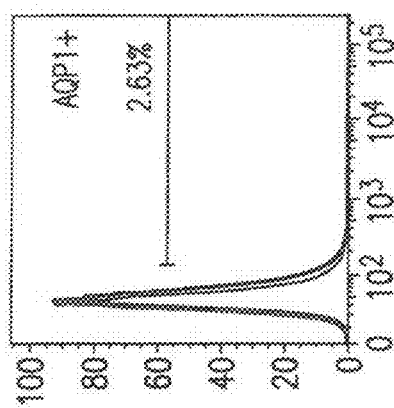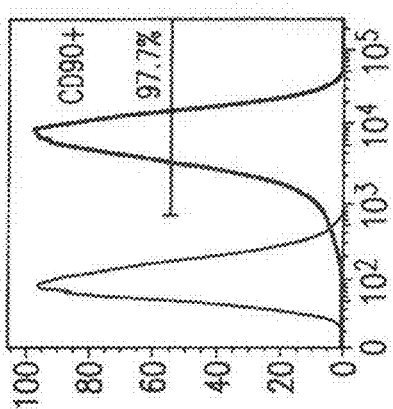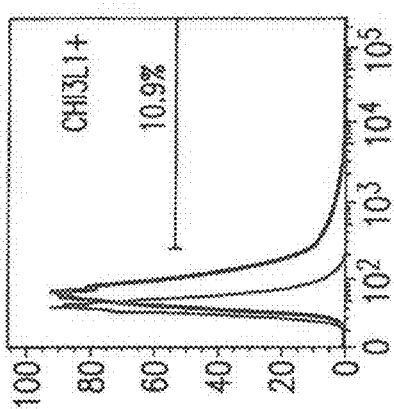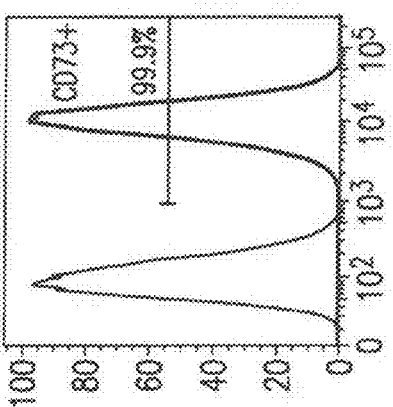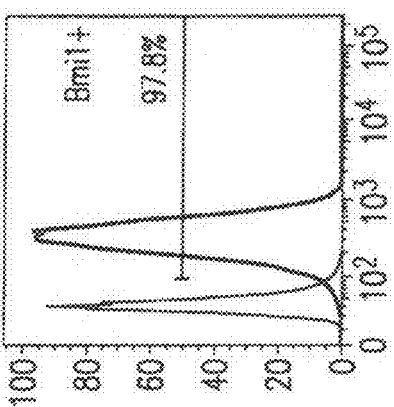

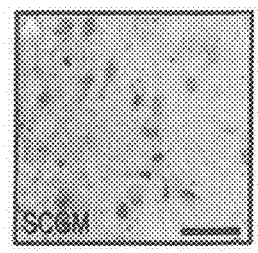 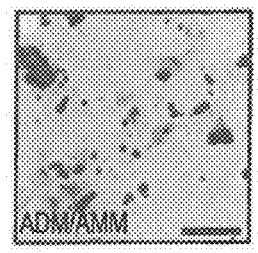
FIG. 12A  FIG. 12B
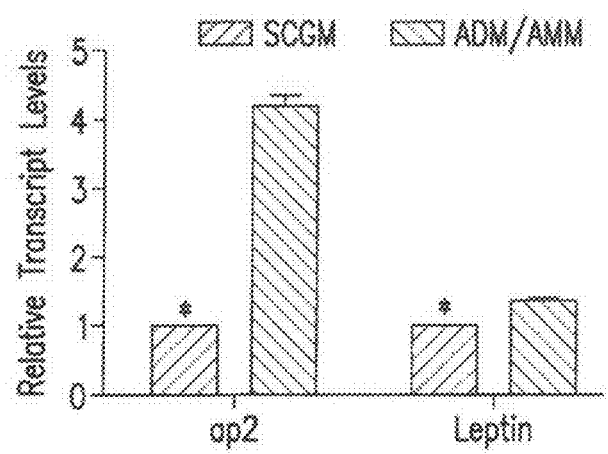
FIG. 12C

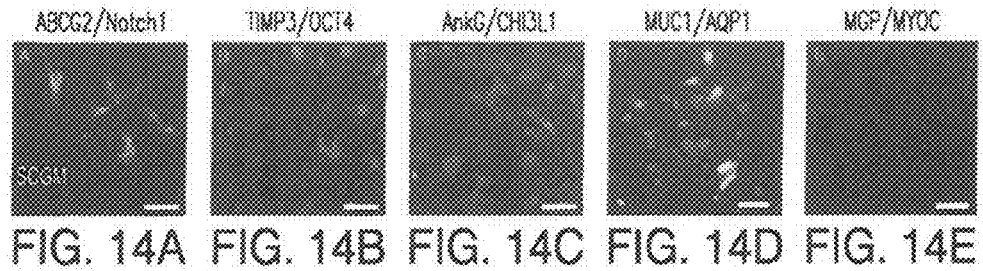
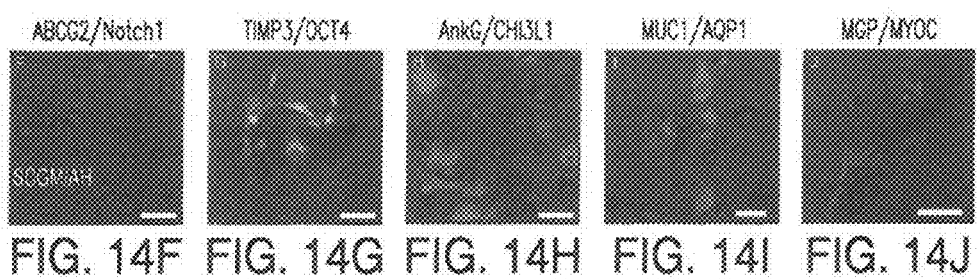
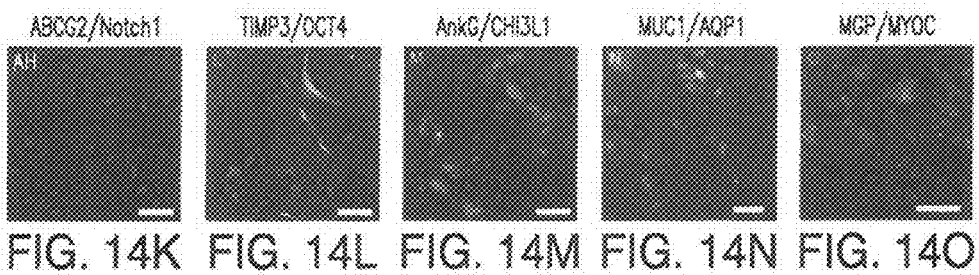
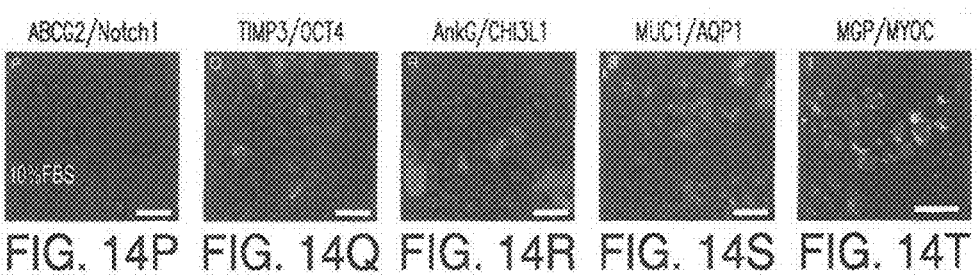
FIG. 14A FIG. 14B FIG. 14C FIG. 14D FIG. 14E
FIG. 14F FIG. 14G FIG. 14H FIG. 14I FIG. 14J
FIG. 14K FIG. 14L FIG. 14M FIG. 14N FIG. 14O
FIG. 14P FIG. 14Q FIG. 14R FIG. 14S FIG. 14T

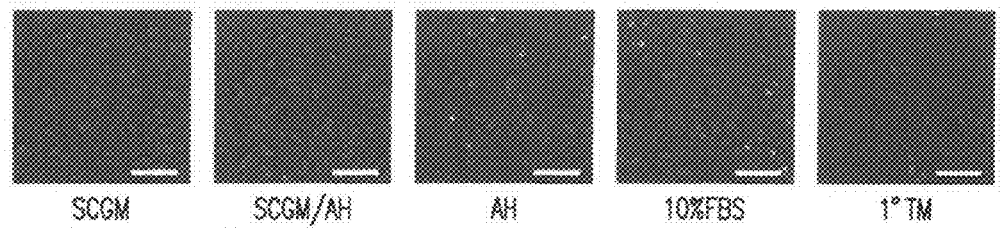
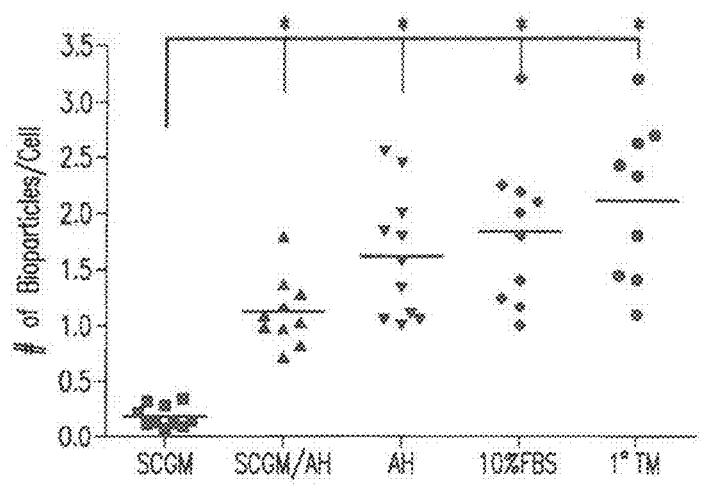
FIG. 16F

SEQUENCE LISTING

```
<160> NUMBER OF SEQ ID NOS: 80

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccctgtaatt ggaatgagtc cac                                            23

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctggaatta ccgcggct                                                  18

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgcaacatgt actggcgaag a                                              21

<210> SEQ ID NO 4
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tcttccacaa gccccagg                                                    18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caatcaaaac gtgtccaacg                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tagccaggtt gcgaagaact                                                  20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gttcctgtag tccaggccta tg                                               22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcaggaatgc tgctgtttag aa                                               22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccaacttcac cagcaaatac aa                                               22

<210> SEQ ID NO 10
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccagtttgtc tctgagcact gt                                                 22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtctgctctt ctgcctcttg at                                                 22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcatatttcc atttgccaaa ca                                                 22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cgagttggcc ctagacttag aa                                                 22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctttgtgatc cgaccatgag ta                                                 22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gccttaacgc tgtgtgtatg ac                                                 22

<210> SEQ ID NO 16
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 16
acctggagat gccagagagt ag                                                  22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaagggtggg ggcaggggag                                                     20

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
agtgtgtcta tctactgtgt cccaggc                                             27

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agtctctgca gtgctggaag ta                                                  22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cttgcagtac tggtcgtaca gg                                                  22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
accctgggtc ttgaggaagt                                                     20

<210> SEQ ID NO 22
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 22
tgccttgaga tgggaactct                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccattccact ccactcaggt                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccacatgagc ttccacacac                                              20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cattcctcca cgcaagtgta                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtgggttggc cagtttatgt                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ctgcacaggc ttgctgtatg                                              20

<210> SEQ ID NO 28
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 28
tgttccttgg gctgcaacta                                                   20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gccgccttag cggtagtaac                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tctctgctga ggggatatga                                                   20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccttgaccgc ttcctctgta                                                   20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtgttgagca tgccgtagag                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atctgcagca ccttcacctt                                                   20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 34
cattggaatt ggtggtttga                                                    20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aagcccacct acccctacac                                                    20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tccagtggcc taggcagtat                                                    20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acacctccac ggaagctatg                                                    20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aattgcaacc aggtgtgtgt a                                                  21

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tggacctgga ggaaatcttg                                                    20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agaatggccg agttcatgag                                        20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
catggccaaa cctaacatga                                        20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aattcctggc ccagtatgaa                                        20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tcctggattc ctttccttca                                        20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
caatcgagga gggcagaata                                        20

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccctgtaatt ggaatgagtc cac                                    23

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 46
gctggaatta ccgcggct                                                 18

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgcaacatgt actggcgaag a                                             21

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tcttccacaa gccccagg                                                 18

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
caatcaaaac gtgtccaacg                                               20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tagccaggtt gcgaagaact                                               20

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
agtctctgca gtgctggaag ta                                            22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
```
cttgcagtac tggtcgtaca gg                                            22

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccattccact ccactcaggt                                               20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccacatgagc ttccacacac                                               20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cattcctcca cgcaagtgta                                               20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gtgggttggc cagtttatgt                                               20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ctgcacaggc ttgctgtatg                                               20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tgttccttgg gctgcaacta                                                20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gccgccttag cggtagtaac                                                20

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tctctgctga ggggaatatg a                                              21

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccttgaccgc ttcctctgta                                                20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gtgttgagca tgccgtagag                                                20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aagcccacct acccctacac                                                20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
tccagtggcc taggcagtat                                                20

```
<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
acacctccac ggaagctatg                                                   20

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
aattgcaacc aggtgtgtgt a                                                 21

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tggacctgga ggaaatcttg                                                   20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
agaatggccg agttcatgag                                                   20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gaggaacacc aagtgggaga                                                   20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ctcctcctct ttggcctctt                                                   20
```

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
actacatcgc cctccacatc                                               20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
caaaggcaca gttcccagat                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
catggccaaa cctaacatga                                               20

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
aattcctgcc cagtatgaa                                                19

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tcctggattc ctttccttca                                               20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
caatcgagga gggcagaata                                               20

```
<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
atctgcagca ccttcacctt                                                 20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cattggaatt ggtggtttga                                                 20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cattggcacc tggaactacc                                                 20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ggcttgagga ccactgagtt                                                 20
```

TRABECULAR MESHWORK STEM CELLS

PRIORITY CLAIM

This application is a divisional of, and claims priority to, U.S. Ser. No. 13/361,908, filed Jan. 30, 2012, and claims priority to provisional application U.S. Ser. No. 61/462,255, filed Jan. 31, 2011 and provisional application U.S. Ser. No. 61/438,163, filed Jan. 31, 2011, both of which are hereby incorporated by reference herein in their entireties.

GRANT FUNDING

This invention was made with government support under Grant Nos. EY016415 and EY008098, awarded by the National Institutes of Health. The government has certain rights in the invention.

SEQUENCE LISTING

The specification further incorporates by reference the Sequence Listing submitted herewith via EFS on Jun. 1, 2012. Pursuant to 37 C.F.R. § 1.52(e)(5), the Sequence Listing text file, identified as 72396478.txt, is 18,411 bytes and was created on May 21, 2012. The Sequence Listing, electronically filed herewith, does not extend beyond the scope of the specification and thus does not contain new matter.

BACKGROUND

The trabecular meshwork (TM) is a region of spongy tissue in the eye located around the base of the cornea and near the ciliary body. The TM functions to drain the aqueous humor from the eye into the circulatory system via the anterior chamber and a series of tubes called Schlemm's canal. In addition to producing and secreting extracellular matrix proteins and proteolytic enzymes, cells of the TM (i.e., TM cells) phagocytose extracellular debris to prevent blockage of Schlemm's canal. Decreased TM cellularity and impaired TM function lead to the pathogenesis of glaucoma, a medical condition of the eye in which aqueous humor outflow is decreased and/or levels of aqueous are increased, either or both of which ultimately lead to an elevation in intraocular pressure.

Current treatments for glaucoma include medications, laser treatment, or surgical treatment. Laser trabeculoplasty is a surgery in which a laser makes tiny, evenly spaced burns in the TM to re-stimulate its drainage function. Laser trabeculoplasty surgery increases cell division in the TM, thereby increasing TM cellularity. Within days of the procedure, cells found in the anterior, non-filtering region of the TM, called the insert area, migrate out of this region and repopulate the laser-burned sites. While laser trabeculoplasty is a quick, easy, convenient, and relatively low-risk procedure, there are drawbacks to this technique. For example, about half of the patients require further medical or surgical treatment within two to five years. Also, for example, the procedure has a relatively small effect on lowering the eye pressure and repeat treatments are usually not very effective. In some people, such as individuals with glaucoma from eye inflammation or eye trauma, the procedure has no benefit and can even worsen the glaucoma.

Surgical treatment options for glaucoma, such as trabeculectomy, also have risks. In some cases, the glaucoma operation fails and requires glaucoma medication or another glaucoma operation. Frequently, the eye pressure becomes severely reduced immediately after surgery. While this is harmless over a short period of time, this can lead to vision changes if the reduced eye pressure continues over a long period of time. Also, surgery treatment most often requires general anesthesia. Further, a leak from the surgery, bleeding in the eye, or infection of the eye can occur post-surgery.

Alternatively, the application or administration of stem cells that have the potential to differentiate into TM cells is an attractive means of treating or preventing glaucoma. It has been postulated that the insert area contains stem-like cells that serve as a source of TM cell renewal, and some groups report attempts to isolate such cells through surgical dissection of the TM insert area. However, Kelley et al., Exp Eye Res 88(4); 747-751 (2009) concede that this method represents a difficult technique. Other groups have cultured TM cells or have produced neurospheres from human TM cultures with an aim to isolate multipotent progenitor cells from the TM. While these groups report the expression profiles of the isolated cells, none have demonstrated that the isolated cells are capable of differentiating into TM cells.

In view of the foregoing, there exists a need in the art for isolated populations of multipotent stem cells that are capable of differentiating into TM cells and non-invasive, efficient methods of obtaining such populations.

SUMMARY

Presented herein for the first time are data which demonstrate that multipotent stem cells exist throughout the TM and are not limited to the insert area (also known as "insert region") of the TM. Once isolated, the multipotent stem cells can be cultivated and passaged in vitro, undergoing multiple cellular divisions without losing their likeness to stem cells, are capable of differentiating into functional trabecular meshwork (TM) cells, and are capable of localizing to the TM after injection into the eye.

Accordingly, the present disclosures provide isolated populations of multipotent stem cells which are capable of differentiating into TM cells. In some embodiments, the isolated population comprises multipotent stem cells isolated from a TM, e.g., a TM obtained from a tissue bank. In exemplary aspects, the TM is a TM of a mammal, e.g., a human, pig, horse, cow, dog, monkey, and the like. In exemplary aspects, the isolated population comprises multipotent stem cells isolated from a filtering region of a TM, and in some embodiments, the isolated population comprises multipotent stem cells isolated from both a filtering region and non-filtering region of the TM. In exemplary embodiments, the isolated population comprises multipotent stem cells isolated from a region other than the insert area of the TM, and in other embodiments, the isolated population comprises multipotent stem cells isolated from the insert area of the TM and from a region other than the insert area.

In exemplary embodiments, the isolated population represents a highly purified population of multipotent stem cells, wherein, for example, at least 90% of the cells of the population are multipotent stem cells. In exemplary aspects, at least 90% of the cells of the population express a stem cell marker selected from the group consisting of ABCG2, Pax6, Nestin, Ankyrin G, Mucin 1, CD73, CD90, CD 166, Bmi-1, CD I 17, Notch I, Oct4, KLF4, and a combination thereof. In exemplary aspects, at least 90% of the cells of the population express Ankyrin G and Mucin 1.

In exemplary embodiments, the stem cells are multipotent insofar as the multipotent stem cells are capable of differentiating into TM cells (e.g., phagocytic TM cells), corneal keratocytes, neural cells, and adipocytes. In exemplary embodiments, the multipotent stem cells represent a single type of precursor cells or progenitor cells that has the capacity to become TM cells (e.g., phagocytic TM cells), the capacity to become corneal ketocytes, the capacity to become neural cells, and the capacity to become adipocytes.

Also provided herein are methods of obtaining an isolated population of TM cells. An exemplary method comprises obtaining an isolated population of multipotent stem cells and culturing the isolated population of multipotent stem cells in a medium comprising factors present in fetal bovine serum, aqueous humor, or in both fetal bovine serum and aqueous humor, to induce differentiation of the multipotent stem cells into TM cells. In exemplary aspects, the isolated population of multipotent stem cells is any one of the presently disclosed isolated populations of multipotent stem cells, e.g., those isolated from a trabecular meshwork. In exemplary aspects, the isolated population of multipotent stem cells is obtained by side population cell sorting of cells of a trabecular meshwork. In exemplary aspects, the isolated population of multipotent stem cells is obtained by clonal expansion of cells of a trabecular meshwork. In exemplary aspects, the isolated population of multipotent stem cells is obtained by selective expansion of stem cells of a trabecular meshwork. The isolated populations of TM cells obtained therefrom are moreover provided.

Further provided herein are compositions comprising the presently disclosed isolated population of multipotent stem cells or the presently disclosed isolated population of TM cells. In exemplary aspects, the composition comprises a pharmaceutically acceptable carrier, diluents, or excipient, such that the composition may be considered as a pharmaceutical composition. In exemplary aspects, the composition comprises a medium comprising factors present in fetal bovine serum, aqueous humor, or in both fetal bovine serum and aqueous humor. In exemplary aspects, the cells are from a human and the aqueous humor is from a non-human. In exemplary aspects, the cells are in solution. In exemplary aspects, the cells are cryopreserved. In exemplary aspects, the compositions are formulated for administration to a subject by implantation or injection. In exemplary aspects, the compositions are formulated for sustained, continuous release. In exemplary aspects, the cells are in a matrix, capsule, or gel.

Furthermore provided are kits and devices comprising the compositions of the present disclosures. In exemplary aspects, the kits comprise instructions for use, e.g., instructions for administration of the composition to a subject, and/or comprise a device for administration of the composition to a subject. In exemplary aspects, the device is a syringe, a matrix, a capsule, or an intravenous bag.

The present disclosures additionally provide multiple different uses of the presently disclosed compositions. In exemplary embodiments, the composition is used in a method of decreasing intraocular pressure in an eye. The method comprises administering to a subject in need thereof a composition comprising an isolated population of multipotent stem cells or TM cells of the present disclosures, in an amount effective to decrease the intraocular pressure in the eye.

In additional exemplary embodiments, the composition comprising an isolated population of multipotent stem cells or TM cells of the present disclosures is used in a method of increasing cell density in a trabecular meshwork of an eye. The method comprises administering to a subject in need thereof a composition comprising an isolated population of multipotent stem cells or TM cells of the present disclosures, in an amount effective to increase cell density in the trabecular meshwork of an eye.

In yet other exemplary embodiments, the composition comprising an isolated population of multipotent stem cells or TM cells of the present disclosures, is used in a method of increasing outflow of aqueous humor from an eye. The method comprises administering to a subject in need thereof a composition comprising an isolated population of multipotent stem cells or TM cells of the present disclosures, in an amount effective to increase outflow of aqueous humor from the eye.

The present disclosures furthermore provide a method of treating or preventing a medical condition. In exemplary aspects, the medical condition is caused by or associated with decreased cell density in a trabecular meshwork, increased intraocular pressure in an eye, decreased outflow of aqueous humor from an eye, or a combination thereof. The method comprises administering to a subject in need thereof a composition comprising an isolated population of multipotent stem cells or TM cells of the present disclosures, in an amount effective to treat or prevent the medical condition. In exemplary aspects, the medical condition is glaucoma.

COLOR FIGURES

The patent or application file contains at least one drawing executed in color. Copies of this patent or patent application publication with color drawing(s) will be provided by the office upon request and payment of the necessary fee.

BRIEF DESCRIPTION OF THE DRAWINGS

FIG. 1A: Immunofluorescent staining on cryosections of human anterior segment shows the distribution of cells positive to stem cell markers ABCG2, Pax6, Muc1 or AnkG (Red) in human TM tissue which is outlined by the TM cell markers AQPI, MGP, CHI3L1, TIMP3 (Green). The cells positive to stem cell markers spread through the TM tissue and are not limited to a specific region. DAPI stains nuclei as blue. Schlemm's canal, TM and cornea are pointed out by arrows. Bars=50 um. FIG. 1B: Expression of stem cell genes (ABCG2, Pax6, Muc1, AnkG) and TM cell genes (AQPI, MGP, CHI3L1) was detected by qPCR to compare the differences between the tissue of TM and of insert region. Corneal keratocyte specific marker keratocan was also compared to exclude the contamination with corneal cells. Both TM and insert express stem cell markers as well as TM markers but not keratocan. Error bars show SD of triplicate analyses. Abbreviations: TM, trabecular meshwork; ABCG2, ATP-binding cassette sub-family G member 2; Muc1, mucin 1; AnkG, ankyrin G; MGP, matrix gla protein; AQPI, aquaporin 1; CH13L1, chitinase 3-like 1; TIMP3, tissue inhibitor of metalloproteinases-3; qPCR, quantitative reverse transcription-polymerase chain reaction, Kera, keratocan.

FIG. 2A: The SP cells were isolated by fluorescence activated cell sorting (FACS) from cultured human TM cells. Passage-three TM cells stained with DyeCycle Violet Dye (DCV) were analyzed using violet 405-nm excitation with blue (450/40) and red (620 LP) emission. Cells showing reduction of both blue and red fluorescence (SP cells) were collected as defined by the box outlined on the left (arrow) which can be eliminated by preincubation with ABCG2 inhibitor fumitremorgin C (FTC). FIG. 2B: The sorted SP and non-SP cells were passaged in vitro and mRNA pools for stem cell makers ABCG2, Muc1 AnkG; TM markers AQP 1, MGP, CHI3L 1; and glaucoma markers myocilin and ELAM 1 were quantified by qPCR to compare the differences between the passaged non-SP and SP cells at passage-eight. Error bars show SD of triplicate analyses. Asterisks indicate significant (p<0.05) difference between non-SP and SP. Abbreviations: SP, side population; TM, trabecular meshwork. Myoc, myocilin, ELAM1, endothelial-leukocyte adhesion molecule 1.

FIG. 3A-3L demonstrates exemplary expression of stem cell markers in passaged TM stem cells. Different expression of stem cell markers ABCG2, Pax6, Ankyrin G, Mucin1 and TM differentiation markers CHI3L1, AQPI, MGP, TTMP3 as well as glaucoma related marker myocilin was detected by immunofluorescent staining on TMSC FIG. 3A-3E and primary TM cells FIG. 3F-3J. FIG. 3A and FIG. 3F show double-stain of ABCG2 and Pax6, FIG. 3B and FIG. 3E are stains of Ankyrin FIG. 3G and CHI3L1, FIG. 3C and FIG. 3H are Mucin 1 and AQP1, FIG. 3D and FIG. 3I are MGP and Myocilin, FIG. 3E and FIG. 3J are T1MP3 stain. DAPI stains nuclei as blue. Bars=50 um. FIG. 3K: mRNA pools for stem cell makers ABCG2, Muc1, AnkG; TM markers AQP1, MGP, CHI3L1; and glaucoma markers myocilin and ELAM1 were quantified by qPCR to compare the differences between the primary cultured TM cell culture and TM stem cells at passage-four. Error bars show SD of triplicate analyses. Asterisks indicate significant (p<0.05) difference between the primary TM cells and TMSC. FIG. 3L: Western blotting shows the passage-four TMSC retained the expression of stem cell markers ABCG2, Pax6, Muc1 but with little expression of TM markers AQP 1, MGP and TIMP3. Line 1, human corneal fibroblasts as control; Line2, passage-4 TMSC. Abbreviations: TMSC, trabecular meshwork stem cells; 1° TM, primary trabecular meshwork cells.

FIG. 4A-4X demonstrates an exemplary induction of TMSC differentiation into TM cells. FIG. 4A: Double fluorescent staining compares the different expression of the TMSC cultured in SCGM (the first column: FIG. 4A, 4E, 4I, 4M, 4Q) and the induced TM cells in SCGM and AH (the second column: FIG. 4B, 4F, 4J, 4N, 4R), in AH only (the third column: FIG. 4C, 4G, 4K, 4O, 4S), or in 10% FBS (the fourth column: FIG. 4D, 4H, 4L, 4P, 4T). FIG. 4A-4D show double-stain of ABCG2 and Pax6, FIG. 4E-4H are stains of Ankyrin G and CHI3L1, I-L are Mucin 1 and AQP1, M-P are MGP and Myocilin, Q-T are TIMP3 stain. DAPI stains nuclei as blue. Bars=50 um.

FIGS. 4V-4X demonstrate differential gene expression among passaged TMSC and differentiated TM cells. FIG. 4V: rnRNA pools for stem cell makers ABCG2, Pax6, CD73, CD90, CD 166, CD 117, Bmi 1, 0CT4, Notch 1, KLF4, Muc1 and AnkG were quantified by qPCR to compare the differences between passaged TM stem cells and induced TM cells with aqueous humor at passage-two as well as passage-five. Error bars show SD of triplicate analyses. Asterisks indicate significant (p<0.05) difference between passaged TMSC and induced TM cells. FIG. 4W: mRNA pools for TM cell makers AQP1, MGP and CHI3L1 were quantified by qPCR to compare the differences between passaged TM stem cells and induced TM cells with aqueous humor at passage-two as well as passage-five. Error bars show SD of triplicate analyses. Asterisks indicate significant (p<0.05) difference between passaged TMSC and induced TM cells. FIG. 4X: Different expression levels of MMPI (interstitial collagenase) were compared by qPCR on passaged TMSC, induced TM cells and fibroblasts. Error bars show SD of triplicate analyses. Asterisks indicate significant (p<0.05) difference between the cells and other groups.

FIG. 5A-5F demonstrates an exemplary phagocytosis of TM cells induced from TMSC. Passaged TMSC were induced to differentiate into TM cells by culturing in STC-MIAH, in AH or in 10% FBS for one week. Phagocytic function was detected by incubating the cells with *Staphylococcus aureus* bioparticles (Green) as described in Materials and Methods. Green particles in FIGS. 5A-5E are the ingested bioparticles by the cells and the yellow dots are not washed out free particles with conjugating with the red secondary antibody. DAPI stains nuclei as blue. Bars=50 um. FIG. 5F The number of ingested bioparticles per cell was counted and compared in TMSC, in the induced TM cells in different induction media and the primary TM cells. Asterisks indicate significant (p<0.0001) difference between TMSC and the induced TM cells. There is no significant difference among the different induction conditions and the primary TM cells. Abbreviations: SCGM, stem cell culture medium; SCGM/AH, 50% stem cell culture medium+50% aqueous humor; AH, aqueous humor; FBS, fetal bovine serum; 1° TM, primary TM cells.

FIG. 6A-6N demonstrates an exemplary induction of TMSC into neural cells, adipocytes and keratocytes. The TMSC were cultured in NDM for neural induction and in ADM and AMM for adipogenic induction as described in the Materials and Methods. The keratocyte differentiation was induced as three dimensional culture in KDM. Immunofluorescent stain compares the cells in NDM FIG. 6A-6D and in. SCGM FIG. 6E-6F. FIG. 6A and FIG. 6E are the stain of NF200; FIG. 6B and FIG. 6F are that of –tubulin HI; FIG. 6C and FIG. 6G are GFAP; FIG. 6D and FIG. 6H are Mucin 1. FIGS. 6I and (7) show oil red O stain on cells induced in ADM and AMM FIG. 6I and cells in SCGM FIG. 6J as control. FIG. 6K and FIG. 6L show the stains on the cryosections of cells cultured as pellets in KDM. Expression of corneal stromal extracellular matrix keratocan sulfate (Green) and keratocan (Red) was shown in FIG. 6K and FIG. 6L, respectively. DAPI stains for nuclei as blue. Bars=50 um. Abbreviations: TMSC, trabecular meshwork stem cells; NDM, neural differentiation medium; ADM, adipogenic differentiation medium; AMM, adipogenic maintenance medium; KDM, keratocyte differentiation medium; NF200, neurofilament 200; GFAP, glial fibrillary acidic protein.

7F, 7K 7P, on fibroblast injection at 1 week FIG. 7E, 7J, 7O and 4 weeks FIG. 7G, 7L, 7Q and on normal wild mouse tissue FIG. 7C, 7H, 7M as controls.

FIG. 8A-8C demonstrate isolation of TMSC as side population (SP) cells. FIG. 8A SP cells were isolated by FACS from passage-three human TM cells using DyeCycle Violet Dye. Cells showing reduction of both blue and red fluorescence (SP cells) were collected as defined by the box outlined on the left (arrow). FIG. 8B The sorted SP and non-SP cells were passaged and assessed for differential gene expression by qRT-PCR. Error bars show SD of triplicate analyses. * p<0.05 (n=3, Student's t test). FIG. 8C RNAs extracted from dissected TM tissue and the adjacent corneal stroma tissue were compared on the expression of TM markers AnkG, CHI3L1; stromal marker KERA and the common marker for both TM and stroma AQP1 to assess if the dissected TM tissue contains corneal tissue. SP, side population; FACS: fluorescence-activated cell sorting.

FIG. 9A-K demonstrate differential expression of stem cell- and TM-markers between TMSC and primary TM cells. Clonal passaged TMSC FIG. 9A-9E and primary TM cells FIG. 9F-9J were double-stained with stem cell markers ABCG2 (green), Notch1 (red), OCT4 (red), AnkG (green), MUC1 (green); TM markers TIMP3 (green), CHI3L1 (red), AQP1 (red), MGP (green); and MYOC (red). Arrows in A point to the ABCG2 and Notch1 double-positive cells. Arrow in J points the MGP and MYOC double-positive cell. DAPI stains nuclei blue. Bars=50 μm. FIG. 9K Expression of stem cell- and TM-markers from primary TM cells and clonal TMSC at passage-four was quantified by qRT-PCR. Error bars show SD of triplicate analyses. * p<0.05 (n=3, Student's t test). TMSC, trabecular meshwork stem cells; 1° TM, primary trabecular meshwork cells.

FIG. 10A-F demonstrates flow analysis of passage-four TMSC to assess the cell purity. Stem cell markers FIG. 10A CD73, FIG. 10B CD90, Figure C CD166, Bmi1 and TM cell markers FIG. 10E CHI3L1, AQP1 were analyzed by flow cytometry. The peak on the left in each histogram represents the isotype control for comparison with the cells labeled for each marker (on the right).

FIG. 11I Neural markers NF and GFAP from TMSC in SCGM and in NDM for neural induction were quantified by qRT-PCR. Error bars show SD of triplicate analyses. * p<0.05 (n=3, Student's t test). TMSC, trabecular meshwork stem cells; NDM, neural differentiation medium; SCGM, stem cell growth medium; GFAP, glial fibrillary acidic protein. NF, neurofilament.

FIG. 12A-C demonstrate induction of adipocyte differentiation from TMSC. TMSC were cultured in ADM and AMM alternately for adipogenic induction. Oil red O (red) staining was compared on TMSC in SCGM FIG. 12A and in ADM/AMM FIG. 12B. Hematoxylin stains nuclei blue. Bars=50 μm. FIG. 12C Adipocytic markers ap2 and Leptin from TMSC in SCGM and induced cells in ADM/AMM were quantified by qRT-PCR. Error bars show SD of triplicate analyses. * p<0.05 (n=3, Student's t test). ADM, adipogenic differentiation medium; AMM, adipogenic maintenance medium; ap2, adipocyte protein 2.

FIG. 13G Keratocytic markers KERA and ALDH from TMSC in SCGM and TMSC cultured as pellets in KDM were quantified by qRT-PCR. Error bars show SD of triplicate analyses. * p<0.05 (n=3, Student's t test). KDM, keratocyte differentiation medium; KERA, keratocan; ALDH, aldehyde dehydrogenase.

FIG. 14A-T demonstrate different protein expression of TMSC and induced TM cells. Immunofluorescence compares different expression of stem cell markers ABCG2, Notch1, OCT4, AnkG, MUC1; TM markers TIMP3, CHI3L1, AQP1, MGP and MYOC of TMSC cultured in SCGM FIG. 14A-14E, in 50% AH in SCGM (SCGM/AH) FIG. 14F-14J, in AH FIG. 14K-14O, or in 10% FBS (P-T). Double-stain model is the same as FIG. 2A-2B and the markers are labeled as green/red on top. DAPI stains nuclei blue. Bars=50 nm. SCGM, stem cell growth medium; AH, aqueous humor; FBS, fetal bovine serum.

FIG. 15A mRNA pools for stem cell makers ABCG2, Pax6, Notch1, MUC1, AnkG; TM markers AQP1, MGP; and MYOC and ELAM1 were quantified by qRT-PCR to compare the differences between TMSC and TM cells induced in different media. Error bars show SD of triplicate analyses. FIG. 15B Western blotting compares expression of stem cell markers ABCG2, OCT4 and TM cell markers AQP1, MGP and CHI3L1 on passage-four TMSC in SCGM, 1° TM cells, induced TM cells in SCGM/AH, AH or 10% FBS. α-tubulin serves as loading control. 1° TM, primary trabecular meshwork cells.

FIG. 16A-F demonstrate phagocytosis. FIGS. 16A-E show phagocytosis assay to compare TMSC, induced and primary TM cells. Green dots are phagocytosed fluorescently-conjugated *S. aureus* bioparticles. Yellow dots are unphagocytosed free bioparticles labeled with red secondary antibody. DAPI stains nuclei blue. Bars=50 μm. FIG. 16F The number of phagocytosed bioparticles per cell shows on the y-axis. The green particles and the nuclei in each view were counted and at least ten different views were counted in each condition. * p<0.0001 between TMSC in SCGM and induced TM cells in different media and 1° TM (n=10, one-way ANOVA followed by the Tukey post-test).

DETAILED DESCRIPTION

Isolated Populations of Multipotent Stem Cells

Figure 1A:
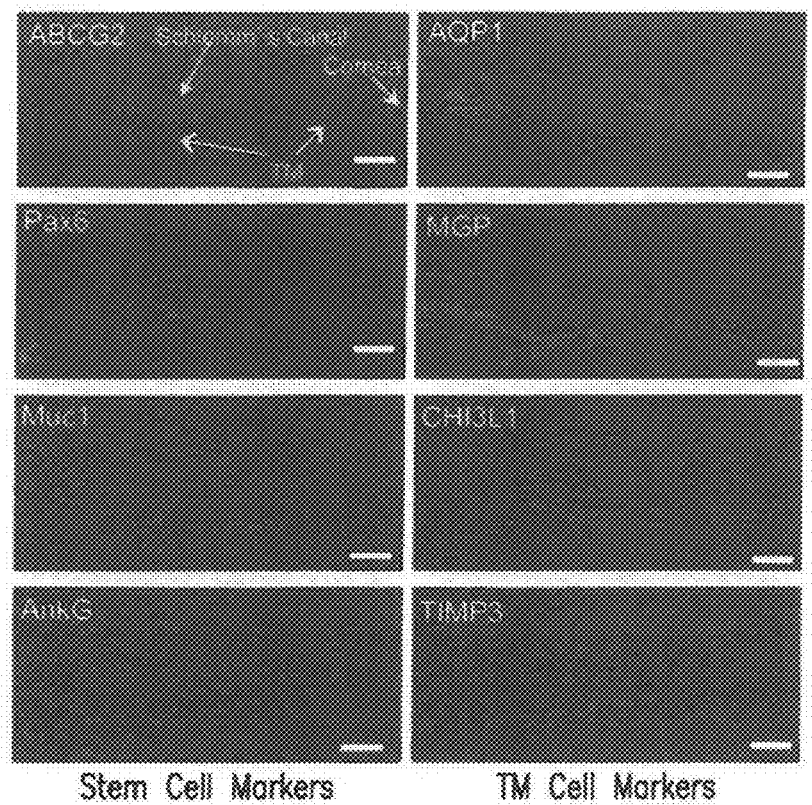
FIG. 1A-1B demonstrates an exemplary distribution of stem cells in trabeculate meshwork.

The present disclosures provide isolated populations of multipotent stem cells which are capable of differentiating into TM cells (e.g., phagocytic TM cells). As used herein, the term "multipotent" refers to adult stem cells or somatic stem cells that can develop into two or more (e.g., two, three, four, five, six, seven, eight, nine, ten, or more) different differentiated cell types. The multipotent stem cells of the isolated populations provided herein are not embryonic stem cells, and, therefore, are neither totipotent stem cells nor pluripotent stem cells, which stem cells are described in Kefley et al., Exp Eye Res. 88 (4): 747-751 (2009). In some embodiments, the stem cells are multipotent due to their potential for differentiating into any of TM cells, corneal ketocytes, neural cells, or adipocytes. In exemplary embodiments, the multipotent stem cells represent a single type of precursor cell or progenitor cell that has the capacity to become TM cells, the capacity to become corneal ketocytes, the capacity to become neural cells, and the capacity to become adipocytes. In some aspects, the multipotent stem cells of the isolated populations provided herein have only these four capacities (e.g., can only differentiate into one of TM cells, corneal ketocytes, neural cells, and adipocytes). In alternative aspects, the multipotent stem cells of the isolated populations provided herein have the capacity to differentiate into additional cell types other than TM cells, corneal ketocytes, neural cells, and adipocytes. In some aspects, the multipotent stem cells which are capable of differentiating into TM cells have the capacity to differentiate into phagocytic TM cells. Additional features and descriptions of the differentiated cells derived from the multipotent stem cells are provided below in the section entitled "Differentiated Cell Types."

In some aspects, the multipotent stems cells of the isolated populations provided herein express one or more (e.g., one, two, three, four, five, six, seven, eight, nine, ten, eleven, twelve, thirteen, fourteen, fifteen, sixteen, seventeen, eighteen, nineteen, twenty, or more) stem cell markers. In the context of the cells of the present disclosures, a cell marker refers to a molecule, such as a polypeptide, protein, mRNA, that is expressed by the cells and assists scientists in the identification of that cell type (either alone, in the case of certain cell type-specific markers, or in combination with other markers or cellular characteristics. For example a stem cell marker is a marker that is expressed by stem cells and is useful for distinguishing a stem cell from other types of cells, such as differentiated cells, e.g., a TM cell, a neural cell, a corneal keratocyte, corneal fibroblasts, a stromal cell, an adipocyte. In exemplary embodiments, the stem cells marker is CD34, CD38, CD90, CD 133, CD105, c-kit, CD73, CD90, CD166, Bmi-1, ABCG2, Pax6, Nestin, Ankyrin G, Mucin 1, bone morphogenetie protein receptor, Lineage surface antigen (lin), Stro-1 antigen, Oct4, or KLF4. In some aspects, the multipotent stem cells express one or more stem cell markers selected from the group consisting of CD73, CD90, CD 166, Bmi-1, Oct4, KLF4, ABCG2, Pax6, Nestin, Ankyrin G, and Mucin 1. In some aspects, the multipotent stem cells express two, three, four, five, six, seven, eight, nine, ten, or all of the stem cell markers CD73, CD90, CD166, Bmi-1, Oct4, KLF4, ABCG2, Pax6, Nestin, Ankyrin G, and Mucin 1. In exemplary aspects, the multipotent stem cells express Mucin 1 and Ankyrin G. In some aspects, the multipotent stem cells express the stem cell marker at a level which is detectable by standard immunohistochemistry techniques, including but not limited to immunofluorescence, fluorescent activated cell sorting (FACS) analysis, and the like, or by polymerase chain reaction (PCR) based techniques, e.g., quantitative PCR. In some aspects, the multipotent stem cells express the stem cell marker at an increased level, as compared to the expression level of the stem cell marker in a differentiated cell, e.g., a TM cell, a neural cell, a corneal keratocyte, corneal fibroblasts, a stromal cell, an adipocyte, and the like.

In some aspects, the multipotent stem cells of the isolated populations provided herein express one or more (e.g., one, two, three, four, five, or more) non-stem cell markers at reduced or undetectable levels. In exemplary instances, the multipotent stem cells express at a reduced or undetectable level a marker that is characteristic of a differentiated cell which is derived from the stem cell. In some instances, the multipotent stem cells express one or more (e.g., one, two, three, four, five, or more) of TM cell markers at reduced levels or at undetectable levels as compared to that expressed by a TM cell (e.g., a differentiated TM cell, a mature TM cell). In some aspects, the TM cell marker is selected from a group consisting of: AQP1, MGP, and CH13L1, NCAM, and TIMP3, or lack of detectable expression of MYOC, or a combination of these TM cell markers. In some aspects, the multipotent stem cells express one or more keratocyte markers at reduced levels or at undetectable levels, as compared to that expressed by keratocytes. In some aspects, the keratocyte marker is keratocan. In some aspects, the multipotent stem cells express one or more neural cell markers at reduced levels or at undetectable levels, as compared to that expressed by neural cells. In some aspects, the neural cell marker is GFAP, neurofilament, (3-tubulin III, or a combination thereof. In some aspects, the multipotent stem cells express one or more adipocyte markers at reduced levels or at undetectable levels, as compared to that expressed by adipocytes. In some aspects, the adipocyte marker is selected from the group consisting of leptin, adiponectin, FABP4, GLUT4, and adipocyte lipid-binding protein (ALBP/ap2). In some aspects, the adipocyte marker is formation of lipoid deposits, e.g., as detected by Oil Red O staining.

In some embodiments, the multipotent stem cells of the isolated populations provided herein may be considered as tissue-specific stem cells that differentiate into the cells of the tissue from which the multipotent stem cells are isolated or obtained. Tissue-specific stem cells are further described in Kelley et al., supra. Accordingly, in some embodiments, the isolated population provided herein comprises multipotent stem cells isolated from the trabecular meshwork, e.g., TM of a mammal (e.g., rat, mouse, pig, cow, dog, chimpanzee, primate, human, and the like). In exemplary aspects, the isolated population comprises multipotent stem cells isolated from a filtering region of the TM, and in same embodiments, the isolated population comprises multipotent stem cells isolated from both a filtering region and non-filtering region of the TM. In some aspects, the isolated population comprises multipotent stem cells that are isolated only from a filtering region of the TM and not from a non-filtering region of the TM. In some aspects, the multipotent stem cells are cells isolated from a region of the TM other than the insert area. In some aspects, the multipotent stem cells are cells isolated from the insert area of the TM and from a region of the TM other than the insert area.

In some aspects, greater than or about 50% (e.g., greater than or about 60%, greater than or about 70%, greater than or about 80%, greater than or about 90%, greater than or about 95%, greater than or about 98%, or almost 100%) of the multipotent stem cells of the isolated population are from a filtering region of the TM. In some aspects, less than or about 50% (e.g., less than or about 40%, less than or about 30%, less than or about 20%, less than or about 10%, less than or about 5% less than or about 2%, or almost 0%) of the multipotent stem cells of the isolated population are from a non-filtering region of the TM. In some aspects, the isolated population lacks multipotent stem cells isolated from the insert area of the TM. In some aspects, the isolated population of multipotent stem cells comprise the multipotent stem cells obtained in accordance with one of the methods of obtaining an isolated population of multipotent stem cells provided herein.

In alternative embodiments, the multipotent stem cells of the isolated populations provided herein are not tissue-specific stem cells. Accordingly, in some aspects, the multipotent stem cells are isolated from a tissue other than the TM. In some aspects, the multipotent stem cells are isolated from a tissue other than a neural tissue. In some aspect, the multipotent stem cells are isolated from a tissue other than adipose. In some aspects, the multipotent stem cells are isolated from bone marrow, adipose tissue, skin, umbilical cord, amniotic fluid.

As used herein, the term "isolated" means having been removed from its natural environment and separated from some or all of the coexisting materials in the natural environment. Accordingly, the isolated populations of multipotent stem cells are stem cells that have been removed from their natural environment and separated from some or all of the other cells and/or tissue of the origin of the multipotent stem cells. For example, an isolated population of multipotent stem cells from a TM represents multipotent stem cells removed from the TM and separated from some or all of the coexisting TM cells and fibroblasts (and connective tissue) found in a TM. In a further example, an isolated population of multipotent stem cells isolated from the filtering region of the TM represents multipotent stem cells removed from the filtering region of the TM and separated from other cells of the filtering region of the TM. In yet another example, an isolated population of multipotent stem cells isolated from the filtering region and non-filtering region of the TM, e.g., the insert area, represent cells removed from the filtering region and non-filtering region, e.g., the insert area, of the TM and separated from other cells of the filtering region and non-filtering region of the TM.

In exemplary aspects, the isolated populations provided herein are purified, e.g., purified from other components (e.g., cells) of the natural environment from which the cells were isolated. The term "purified" as used herein means having been increased in purity, wherein "purity" is a relative term, and not to be necessarily construed as absolute purity. For example, the purity can be greater than or about 50% (e.g., greater than or about 60%, greater than or about 70%, greater than or about 80%, greater than or about 90%, greater than or about 95%, greater than or about 98%, or almost 100%) The isolated populations in some aspects may be purified of cells of the TM which are not stem cells, e.g., the isolated populations are purified from TIv1 cells.

In some embodiments, the isolated population represents a substantially purified population of multipotent stem cells, wherein, for example, greater than or about 50% (e.g., greater than or about 60%, greater than or about 70%, greater than or about 80%, greater than or about 90%, greater than or about 95%, greater than or about 98%, or almost 100%) of the cells of the population are multipotent stem cells. In some aspects, greater than or about 50% (e.g., greater than or about 60%, greater than or about 70%, greater than or about 80%, greater than or about 90%, greater than or about 95%, greater than or about 98%, or almost 100%) of the cells of the population express at least one stem cell marker selected from the group consisting of ABCG2, Ankyrin 5 Pax6, Nestin, Mucin 1, CD73, CD90, CD166, Bmi-1, Oct4, CD117, Notch1, and KLF4. In some embodiments, the stem cell marker is expressed by greater than or about 50% (e.g., greater than or about 60%, greater than or about 70%, greater than or about 80%, greater than or about 90%, greater than or about 95%, greater than or about 98%, or almost 100%) of the cells of the population at an increased level, as compared to cells which are known not to be stem cells, e.g., non-stem cells (e.g., TM cells, fibroblasts, keratocytes, neural cells, adipocytes, and the like).

In some aspects, less than or about 50% (e.g., less than or about 40%, less than or about 30%, less than or about 20%, less than or about 10%, less than or about 5%, less than or about 2%, or almost 0%) of cells of the isolated population are cells other than multipotent stem cells. In some aspects, less than or about 50% (e.g., less than or about 40%, less than or about 30%, less than or about 20%, less than or about 10%, less than or about 5%, less than or about 2%, or almost 0%) of the cells of the isolated population are non-stem cells (e.g., TM cells, fibroblasts, keratocytes, neural cells, adipocytes, and the like).

In some aspects, the isolated populations are homogeneous populations consisting of only one type of cell, the multipotent stem cells. In some aspects, the isolated populations are substantially homogenous populations consisting essentially of multipotent stem cells. In exemplary embodiments, greater than or about 50% (e.g., greater than or about 60%, greater than or about 70%, greater than or about 80%, greater than or about 90%, greater than or about 95%, greater than or about 98%, or almost 100%) of the cells of the isolated populations provided herein are multipotent stem cells, e.g., multipotent stem cells that express one or more stem cell markers, as described herein. In some aspects, the isolated population is a clonal population of multipotent stem cells in which each cell of the population is genetically indistinct from another cell of the population. In alternative aspects, the isolated population consists of only or consists essentially of multipotent stem cells, but the isolated population is not a clonal population of genetically indistinct multipotent stem cells.

Methods of Obtaining Isolated Populations of Multipotent Stem Cells

The presently disclosed isolated populations of multipotent stem cells may be obtained through one of a variety of methods. In exemplary embodiments, the multipotent stem cells are from a TM. In exemplary aspects, the TM is a TM of a mammal, such as any mammal described herein, e.g., mouse, rat, pig, human, dog, cat, horse, cow, chimpanzee, primate. In exemplary aspects, the human is an adult (e.g., aged 18 years or more). In exemplary aspects, the human is a child or a fetus. In exemplary aspects, the human is living. In exemplary aspects, the human is deceased, e.g., recently deceased (e.g., deceased within 1 month, 2 weeks, 1 week, 3 days, 2 days, 1 day, 12 hours, 6 hours, from time of TM collection). In exemplary embodiments, the cells of a trabecular meshwork are cells of an eye, or part thereof (e.g., cornea, sclera rim, TM) obtained from a tissue bank, e.g., a human tissue bank. Collection of TM tissue from a cornea obtained from a tissue bank and processing of the TM tissue to obtain cells are described herein (Example 1).

In exemplary embodiments, the multipotent stem cells are from a source other than a TM, e.g., bone marrow, adipose tissue, skin, umbilical cord, amniotic fluid.

In exemplary embodiments in which the multipotent stem cells are from a TM, the isolated population of multipotent stem cells are obtained by side population cell sorting of cells of a TM. Such cell sorting methods are described herein (e.g., Example 1) and, in the context of other cell types, in, e.g., Goodell, Curr Protocols in Cytometry 34: 9.18.1-

9.18.11 (2005), Telford, "Stem Cell Side Population Analysis and Sorting Using DyeCycle Violet," Current Protocols in Cytometry Unit 9.30 (2010), Telford et al., Stem Cells 25: 1029-1036 (2007), Telford, Applications of Flow Cytometry in Stem Cell Research and Tissue Regeneration, ed. Krishan et al., pages 25-44 (2010), and Camargo et al., Blood 107: 501-507 (2006).

In exemplary aspects, the isolated population of multipotent stem cells which are capable of differentiating into TM cells are obtained through a side population cell sorting method comprising (i) contacting cells isolated from a trabecular meshwork with a dye which (a) is effluxed by an ABCG2 protein and (b) emits a detectable signal at a known wavelength, (ii) isolating cells exhibiting a reduced emission of the detectable signal at the known wavelength from cells exhibiting an increased emission of the detectable signal at the known wavelength.

In exemplary aspects, the cells isolated from a TM are propagated or cultured at a low cell density before being contacted with the dye. For example, in some aspects, the cells are propagated at a cell density of about 1000 cells/cm$^2$ to about 20,000 cells/cm$^2$. In exemplary aspects, the cells are propagated or cultured at the low cell density for about 14 to about 28 days or at least or about 2 (e.g., at least or about three, at least or about four, at least or about five, at least or about six, at least or about seven, at least or about eight, at least or about nine, at least or about ten) passages.

In exemplary aspects, the dye used in the side population cell sorting method is a dye that intercalates into DNA. In some aspects, the dye is a fluorescent dye. In some aspects, the dye is a cell membrane permeable, fluorescent vital dye that intercalates into DNA and is a substrate for ABCG2-mediated efflux, e.g., DyeCycle Violet. Such dyes are commercially available through vendors, such as Invitrogen (Carlsbad, Calif.). In some aspects, the dye is Hoechst 33342, which is commercially available from Sigma-Aldrich, St. Louis, Mo.).

In alternative embodiments, the isolated population of multipotent stem cells are obtained by clonal expansion of cells of a trabecular meshwork, which cells express stem cell markers. Such methods are described herein (e.g., Example 1) and, in the context of other cell types, in, e.g., Halleux et al., J Musculoskele Neuron Interact 2(1): 71-76 (2001).

In yet other embodiments, the isolated population of multipotent stem cells is obtained by selective expansion of stem cells of a TM in a culture medium which promotes growth of stem cells while preventing or inhibiting growth of non-stem cells of the TM (e.g., mature TM cells, fibroblasts). In exemplary aspects, the culture medium is a culture medium comprising growth factors and cytokines (e.g., IL-6, stem cell factor) suitable for the growth of stem cells. In exemplary aspects, the culture medium substantially lacks growth factors or cytokines necessary for the growth of TM cells or fibroblasts.

Once obtained, the isolated populations of multipotent stem cells may be cultured under any suitable culturing conditions known in the art, e.g., conditions which promote cellular growth and expansion. Suitable culturing conditions include those described herein (e.g., Example 1) and in Adult Stem Cells, Turksen, ed., Humana Press, 2004, and Stem Cells Handbook, Sell, ed., Humana Press, 2003, or conditions varied therefrom which conditions may be empirically determined. In exemplary embodiments, the isolated populations of multipotent stem cells are cultured in a medium comprising serum, epidermal growth factor, pituitary extract, ascorbic acid, chondroitin sulfate, calcium chloride, or a combination thereof. In exemplary aspects, the medium comprises at least one antibiotic, e.g., penicillin, streptomycin, gentamicin, and the like.

Methods of Obtaining Isolated Populations of Differentiated Cells

Presented herein for the first time are data which demonstrate that multipotent stem cells can be induced to differentiate into functional trabecular meshwork cells, e.g., phagocytic TM cells. As demonstrated herein, the multipotent stem cells that have the capacity to differentiate into TM cells also are capable of differentiating into other cells types, including, but not limited to, keratocytes, neural cells, and adipocytes, thus, demonstrating the multipotent nature of the stem cells. Accordingly, the present disclosures also provide methods of obtaining an isolated population of differentiated TM cells, differentiated keratocytes, differentiated neural cells, or differentiated adipocytes from multipotent stem cells. In exemplary embodiments, the method comprises obtaining an isolated population of multipotent stem cells (e.g., from a TM) and culturing the isolated population of multipotent stem cells in a medium comprising factors sufficient and appropriate for induction of differentiation of the multipotent stem cell into the differentiated cell (e.g., TM cell. keratocyte, neural cell, adipocyte).

In exemplary embodiments, the step of obtaining the isolated population of multipotent stem cells is preformed as described herein (e.g., the section entitled "Methods of obtaining isolated populations of multipotent stem cells"). In exemplary aspects, the isolated population of multipotent stem cells is obtained via side population cell sorting of cells of a TM, clonal expansion of cells of a TM, or selective expansion of stem cells of a TM in a culture medium which promotes growth of stem cells while preventing of inhibiting growth of non-stem cells of the TM.

In exemplary embodiments, the method provided herein is a method of obtaining an isolated population of differentiated TM cells. In exemplary aspects, the method comprises obtaining an isolated population of multipotent stem cells (e.g., via side population cell sorting, clonal expansion of cells of a TM, selective expansion of stem cells of a TM). In exemplary aspects, the isolated population of multipotent stem cells is in accordance with the descriptions of isolated populations of multipotent stem cells described herein (see, e.g., "Isolated populations of multipotent stem cells"). Once obtained, the isolated population of multipotent stem cells are cultured in a medium comprising factors present in fetal bovine serum, aqueous humor, or in both fetal bovine serum and aqueous humor. In exemplary aspects, the medium comprises aqueous humor, fetal bovine serum, or both aqueous humor and fetal bovine serum. In exemplary aspects, the aqueous humor is obtained from a non-human mammal (e.g., cow, pig, horse, dog, cat, monkey) and the multipotent stem cells are human multipotent stem cells. In some aspects, the medium comprises at least or about 25% (v/v) aqueous humor. In exemplary aspects, the medium comprises at least or about 30% (e.g., 35%, 40%, 45%, 50%, 55%, 60%, 65%, 70%, 75%, 80%, 85%, 90%, 95%, 100%) (v/v) aqueous humor. In some aspects, the medium comprises X % (v/v) aqueous humor and Y % stem cell growth medium (e.g., as described herein), wherein Y %=(100%−X %) and X % is an integer between 0 and 100. In some aspects, the medium comprises at least or about 5% (v/v) fetal bovine serum. In exemplary aspects, the medium comprises at least or about 10% (e.g., 15%, 20%, 25%, 30%, 35%, 40%, 45%, 50% or more (e.g., 55%, 60%, 65%, 70%, 75%, 80%, 85%, 90%, 95%, 100%)) (v/v) fetal bovine serum. In exemplary aspects, the medium comprising fetal bovine serum comprises Dulbecco's Modified Eagle Medium (DMEM): Nutrient Mixture F-12 (DMEMIF"12)® (Invitrogen, Carlsbad, Calif.). In exemplary aspects, the multipotent stem cells used in the method of obtaining an isolated population of differentiated TM cells are the multipotent stem cells of the present disclosures. Such methods are further described herein (e.g., Example 1).

In exemplary embodiments, the method provided herein is a method of obtaining an isolated population of differentiated keratocytes. In exemplary aspects, the method comprises obtaining an isolated population of multipotent stem cells (e.g., via side population cell sorting or clonal expansion of cells of a TM) and culturing the isolated population in a keratocyte differentiation medium (KDM). In some aspects, the KDM comprises fibroblast growth factor-2 and/or ascorbic acid-2-phosphate. In some aspects, the KDM comprises Advanced® MEM (Invitrogen) supplemented with fibroblast growth factor-2 and/or ascorbic acid-2-phosphate. In some aspects, the multipotent stem cells are the multipotent stem cells of the present disclosures. Such methods are further described herein (e.g., Example 1).

In exemplary embodiments, the method provided herein is a method of obtaining an isolated population of differentiated neural cells. In exemplary aspects, the method comprises obtaining an isolated population of multipotent stem cells (e.g., via side population cell sorting or clonal expansion of cells of a TM) and culturing the isolated population in a neural differentiation medium (NDM). In some aspects, the NDM comprises epithelial growth factor, fibroblast growth factor, all-trans retinoic acid, or a combination thereof. In some aspects, the NDM comprises penicillin, streptomycin, gentamicin, or a combination thereof. In some aspects, the NDM comprises Advanced® DMEM (Invitrogen) supplemented with epithelial growth factor, fibroblast growth factor, all-trans retinoic acid, penicillin, streptomycin, gentaraicin, or a combination thereof. In exemplary aspects, the multipotent stem cells in the NDM are plated onto a dish (e.g., a plastic dish) coated with a medium which promotes attachment of cell to the dish, e.g., FNC Coating Mix® (AthenaES). In exemplary aspects, the multipotent stem cells used in the method of obtaining an isolated population of differentiated neural cells are the multipotent stem cells of the present disclosures. Such methods are further described herein (e.g., Example 1).

In exemplary embodiments, the method provided herein is a method of obtaining an isolated population of differentiated adipocytes. In exemplary aspects, the method comprises obtaining an isolated population of multipotent stem cells (e.g., via side population cell sorting or clonal expansion of cells of a TM) and culturing the isolated population in an adipogenic differentiation medium (ADM). In some aspects, the ADM comprises fetal bovine serum, dexamethasone, methyl-isobutylxanthine, insulin, or a combination thereof. In some aspects, the ADM comprises indomethacin, penicillin, streptomycin, gentamicin, or a combination thereof. In some aspects, the ADM comprises DMEM-Law glucose (Invitrogen) supplemented with fetal bovine serum, dexamethasone, methyl-isobutylxanthine, insulin, indomethacin, penicillin, streptomycin, gentainicin, or a combination thereof. In exemplary aspects, the multipotent stem cells in the ADM are plated onto a dish (e.g., a plastic dish) coated with gelatin (e.g., 1% (v/v) gelatin). in exemplary aspects, the multipotent stem cells used in the method of obtaining an isolated population of differentiated adipocytes are the multipotent stem cells of the present disclosures. Such methods are further described herein (e.g., Example 1).

Differentiated Cell Types

In addition to providing methods of obtaining isolated populations of differentiated cells, the present disclosures further provide the isolated populations of the differentiated cells obtained through these methods. In exemplary aspects, the differentiated cells (e.g., the TM cells, corneal keratocytes, neural cells, or adipocytes) obtained through the above-described methods express a stem cell marker at a reduced level or an undetectable level, as compared to multipotent stem cells, e.g., the multipotent stem cells from which the cells derived or originated. In exemplary aspects, the stem cell marker is selected from the group consisting of ABCG2, Pax6, Nestin, AnkyriuG, Mucin1, CD73, CD9Q, CD166, Bmi-1, CD117, Notch1, Oct4, KLF4, and a combination thereof. Further descriptions of each type of differentiated cells are provided below.

A. TM Cells

When the differentiated cells are TM cells, the TM cells in some aspects express a TM cell marker at an increased level, as compared to multipotent stem cells, e.g., the multipotent stem cells from which the cells derived or originated. In exemplary aspects, the TM cell marker is selected from the group consisting of MGP, AQP1, CHI3L1, NCAM, TIMP3, and a combination thereof.

In exemplary aspects, the differentiated TM cells are phagocytic TM cells, For example, in certain aspects, the TM cells of the isolated populations provided herein are capable of phagocytosing extracellular debris, such that the TM cells function to prevent blockage of Schlemm's canal in an eye.

In accordance with the foregoing, the present disclosures further provide isolated populations of TM cells, e.g., phagocytic TM cells, which are obtained through the presently disclosed methods, e.g., obtained through induced differentiation of multipotent stem cells. In exemplary aspects, the isolated populations of TM cells are purified or homogenous or substantially homogenous as taught above, with respect to isolated populations of multipotent stem cells. For example, in some aspects, the isolated population of TM cells is purified or homogenous or substantially homogenous such that greater than or about 50% (e.g., greater than or about 60%, greater than or about 70%, greater than or about 80%, greater than or about 90%, greater than or about 95%, greater than or about 98%, or almost 100%) of the cells of the isolated population are TM cells. In further aspects, less than or about 50% (e.g., less than or about 40%, less than or about 30%, less than or about 20%, less than or about 10%, less than or about 5%, less than or about 2%, or almost 0%) of the cells of the isolated population are cells other than a TM cell, e.g., a multipotent stem cell, a keratocyte, a neural cell, adipocyte.

B. Corneal Keratocytes

When the differentiated cells are corneal keratocytes, the corneal keratocytes in some aspects express a keratocyte marker at an increased level, as compared to multipotent stem cells, e.g., the multipotent stem cells from which the cells derived or originated. In exemplary aspects the keratocyte marker is keratocan.

In accordance with the foregoing, the present disclosures provides isolated populations of corneal keratocytes which are obtained through the presently disclosed methods, e.g., obtained through induced differentiation of multipotent stem cells. In exemplary aspects, the isolated populations of corneal keratocytes are purified or homogenous or substantially homogenous as taught above, with respect to isolated populations of multipotent stem cells. For example, in some aspects, the isolated population of corneal keratocytes is purified or homogenous or substantially homogenous such that greater than or about 50% (e.g, greater than or about 60%, greater than or about 70%, greater than or about 80%, greater than or about 90%, greater than or about 95%, greater than or about 98%, or almost 100%) of the cells of the isolated population are corneal keratocytes. In further aspects, less than or about 50% (e.g., less than or about 40%, less than or about 30%, less than or about 20%, less than or about 10%, less than or about 5%, less than or about 2%, or almost 0%) of the cells of the isolated population are cells other than a corneal keratocyte, e.g., a multipotent stem cell, a TM cell, a neural cell, an adipocyte.

C. Neural Cells

When the differentiated cells are neural cells, the neural cells in some aspects express a neural cell marker at an increased level, as compared to multipotent stem cells, e.g., the multipotent stem cells from which the cells derived or originated. In exemplary aspects the neural cell marker is selected from the group consisting of GFAP, neurofilament, and J3-tubulin III, and a combination thereof.

In accordance with the foregoing, the present disclosures provides isolated populations of neural cells which are obtained through the presently disclosed methods, e.g., obtained through induced differentiation of multipotent stem cells. In exemplary aspects, the isolated populations of neural cells are purified or homogenous or substantially homogenous as taught above, with respect to isolated populations of multipotent stem cells. For example, in some aspects, the isolated population of neural cells is purified or homogenous or substantially homogenous such that greater than or about 50% (e.g., greater than or about 60%, greater than or about 70%, greater than or about 80%, greater than or about 90%, greater than or about 95%, greater than or about 98%, or almost 100%) of the cells of the isolated population are neural cells. In further aspects, less than or about 50% (e.g., less than or about 40%, less than or about 30%, less than or about 20%, less than or about 10%, less than or about 5%, less than or about 2%, or almost 0%) of the cells of the isolated population are cells other than a neural cell, e.g., a multipotent stem cell, a TM cell, a corneal keratocyte, an adipocyte.

D. Adipocytes

When the differentiated cells are adipocytes, the adipocytes in some aspects express an adipocyte marker at an increased level, as compared to multipotent stem cells, e.g., the multipotent stem cells from which the cells derived or originated. In exemplary aspects the adipocyte marker is selected from the group consisting of leptin, adiponectin, FABP4, GLUT4, ALBP/ap2, and a combination thereof. In exemplary aspects, the adipocytes exhibit an increased level of lipoid deposits, as compared to the multipotent stem cells from which the adipocytes originated.

In accordance with the foregoing, the present disclosures provides isolated populations of adipocytes which are obtained through the presently disclosed methods, e.g., obtained through induced differentiation of multipotent stem cells. In exemplary aspects, the isolated populations of adipocytes are purified or homogenous or substantially homogenous as taught above, with respect to isolated populations of multipotent stem cells. For example, in same aspects, the isolated population of adipocytes is purified or homogenous or substantially homogenous such that greater than or about 50% (e.g., greater than or about 60%, greater than or about 70%, greater than or about 80%, greater than or about 90%, greater than or about 95%, greater than or about 98%, or almost 100%) of the cells of the isolated population are adipocytes. in further aspects, less than or about 50% (e.g., less than or about 40%, less than or about 30%, less than or about 20%, less than or about 10%, less than or about 5%, less than or about 2%, or almost 0%) of the cells of the isolated population are cells other than an adipocyte, e.g., a multipotent stem cell, a TM cell, a corneal keratocyte, a neural cell.

Single Cells

In addition to the isolated populations of multipotent stem cells and isolated populations of differentiated cells (e.g., TM cells, corneal keratocytes, neural cells, adipocytes), the present disclosures furthermore provides the cells in singular form. Accordingly, the present disclosures provides an isolated multipotent stem cell capable of differentiating into a TM cell, as well as an isolated differentiated cell e.g., an isolated TM cell, an isolated corneal keratocyte, an isolated neural cell, an isolated adipocyte. In exemplary embodiments, the isolated cell exhibits a marker expression profile in accordance with the teachings of the corresponding isolated population provided herein. For example, in some aspects, the isolated multipotent stem cell provided herein expresses a stem cell marker selected from the group consisting of ABCG2, Ankyrin 5 Pax6, Nestin, Mucin 1, CD73, CD9Q, CD166, Bmi-1, CD117, Notch1, Oct4, KLF4, and a combination thereof. Also, for example, the isolated TM cell provided herein expresses a TM cell marker selected from the group consisting of MGP, AQP1, CHI3LI, NCAM, TIMP3, and a combination thereof, at an increased level, as compared to the multipotent stem cell from which the TM cell originated. Further, for example, the isolated corneal keratocyte expresses keratocan at an increased level, as compared to the multipotent stem cell from which the keratocyte originated.

Furthermore, for example, the isolated neural cell expresses a neural cell marker selected from the group consisting of GFAP, neurofilament, (β-tubulin III and a combination thereof, at an increased level, as compared to the multipotent stem cell from which the neural cell originated. Moreover, for example, the isolated adipocyte exhibits an increased level of lipoid deposits, or an increased level of an adipocyte marker selected from the group consisting of leptin, adiponectin, FABP4, GLUT4, ALBP/ap2, and a combination thereof, as compared to the multipotent stem cell from which the adipocyte originated.

Genetically Modified Cells

In exemplary embodiments, the multipotent stem cells or the differentiated cells of the present disclosures are genetically modified to contain a recombinant nucleic acid. By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

In exemplary embodiments, the recombinant nucleic acid encodes a protein and the cell expresses the protein. In exemplary embodiments, the recombinant nucleic acid inhibits or prevents expression of a protein by the cell in which the recombinant nucleic acid resides. The protein may be any protein, e.g., an enzyme, signaling protein, a ligand binding protein, a structural protein, a cell surface receptor, a cytokine, a growth factor, a signal transduction factor, a transcription factor, and the like. The protein in some aspects is a protein which is naturally expressed by the cell in which the recombinant nucleic acid resides. In some aspects, the protein is one which is not naturally expressed by the cell in which the recombinant nucleic acid resides. In exemplary aspects, the protein is selected from the group consisting of the proteins listed in Table A set forth below.

Pharmaceutical Compositions and Formulations

The isolated populations or isolated cells of the present disclosures are optionally formulated into a composition, such as a pharmaceutical composition. In this regard, provided herein is a pharmaceutical composition comprising any of the presently disclosed isolated populations of multipotent stem cells, TM cells, corneal keratocytes, neural cells or adipocytes, and a pharmaceutically acceptable carrier. Also provided is a pharmaceutical composition comprising an isolated multipotent stem cell, an isolated TM cell, an isolated corneal keratocyte, an isolated neural cell, or an isolated adipocyte, of the present disclosures and a pharmaceutically acceptable carrier.

The carrier is any of those conventionally used and is limited only by chemico-physical considerations, such as solubility and lack of reactivity with the cells, and by the route of administration. The pharmaceutically acceptable carriers described herein, for example, vehicles, adjuvants, excipients, and diluents, are well-known to those skilled in the art and are readily available to the public. In one aspect, the pharmaceutically acceptable carrier is one which is chemically inert to the cells, and one which has no detrimental side effects or toxicity under the conditions of use. The choice of carrier will be determined in part by the particular agents comprising the pharmaceutical composition, as well as by the particular route used to administer the pharmaceutical composition. Accordingly, there are a variety of suitable formulations of the pharmaceutical composition of the present disclosures.

Depending on the route of administration, the particular cell or isolated population of cells intended for use, as well as other factors, the pharmaceutical composition may comprise additional pharmaceutically acceptable ingredients, including, for example, one or more of additives, adsorbents, anticoagulants, antimicrobial preservatives, antioxidants, buffering agents, cryoprotectant, diluents, preservatives, stabilizing agents, therapeutic agents, tonicity agents, toxicity agents, viscosity-increasing or -decreasing agents. Accordingly, in exemplary embodiments, the pharmaceutical composition comprises any one or more of the components in the Handbook of Pharmaceutical Excipients, Third Edition, A. H. Kibbe (Phamaceutical Press, London, UK, 2000), which is incorporated by reference in its entirety. Remington's Pharmaceutical Sciences, Sixteenth Edition, E. W. Martin (Mack Publishing Co., Easton, Pa., 1980), which is incorporated by reference in its entirety, discloses various components used in formulating pharmaceutically acceptable compositions and known techniques for the preparation thereof, provided that the component does not adversely affect the viability or functionality of the cells. Supplementary active ingredients also can be incorporated into the compositions.

When the compositions include a cryopreserved cells, the composition in some aspects comprises a cryoprotectant. In some embodiments, the cryoprotectant is a glycol, e.g., ethylene glycol, propylene glycol, glycerol, DMSO, formamide, 2-methyl,~2,4-pentadiol, sucrose, trehalose, and colloid. Methods of cryopreservation are known in the art and include, but not limited to those described in Lee et al., Ferl Steri193 (3): 976-985 (2008); Berz et al., Am J Hernatal 82(6): 463-472 (2007); Watt et al., Methods Ml. Biol. 368: 237-259 (2007); Warkentin et al., Prog Clin Biol Res 389; 643-647 (1994); Slaper-Cortenbach et al., Prog Clin Biol Res 389: 649-656 (1994), and Magrin et al., Haematologica 76 Suppl 1: 55-57 (1991).

In some embodiments, the compositions of the present disclosures comprises a cell culture medium suitable for the viability and functionality of the cells. In exemplary aspects, the composition comprises one or more growth factors and/or cytokines, optionally selected from the group consisting of: platelet derived growth factor (PDGF), a fibroblast growth factor (FGF), transforming growth factor (TGF), epidermal growth factor (EGF), interleukin-2 (IL-2), interleukin-6 (IL-6), granulocyte macrophage colony stimulating factor (GM-CSF), c-Kit, tumor necrosis factor (TNF), stromal cell-derived factor (SDF), granulocyte colony stimulating factor (G-CSF), interferon, bone morphogenetic protein (BMP), connective tissue growth factor (CTGF), and K1f4. In exemplary aspects, the composition comprises a medium comprising factors present in fetal bovine serum, aqueous humor, or in both fetal bovine serum and aqueous humor. In some embodiments, the compositions comprise growth factors and/or cytokines found in aqueous humor. In some embodiments, the compositions comprise a medium comprising serum or components thereof, e.g., fetal bovine serum, human serum albumin. In some embodiments, the compositions are serum-free. In exemplary aspects, the composition comprises a medium comprising fetal bovine serum and/or aqueous humor. In exemplary aspects, the aqueous humor is from a non-human (e.g., cow, pig, horse, mouse, rat, dog, cat, monkey) and the cells of the composition are from a human.

In some embodiments, the foregoing component(s), e.g., fetal bovine serum, aqueous humor, may be present in the pharmaceutical composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w1v. In some embodiments, the foregoing component(s) may be present in the pharmaceutical composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the pharmaceutical composition at any concentration range, such as, for example from about A to about B. In some embodiments, A is 0.0001% and B is 90%.

The pharmaceutical compositions may be formulated to achieve a physiologically compatible pH. In some embodiments, the pH of the pharmaceutical composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the pharmaceutical compositions may comprise buffering agents to achieve a physiological compatible pH. The buffering agents may include any compounds capable of buffering at the desired pH such as, for example, phosphate buffers (e.g., PBS), triethanolamine, Tris, bicine, TAPS, tricine, HEPES, TES, MOPS, PIPES, cacodylate, MES, and others. In certain embodiments, the strength of the buffer is at least 0.5 mM, at least 1 mM, at least 5 mM, at least 10 mM, at least 20 mM, at least 30 mM, at least 40 mM, at least 50 mM, at least 60 mM, at least 70 mM, at least 80 mM, at least 90 mM, at least 100 mM, at least 120 mM, at least 150 mM, or at least 200 mM. In some embodiments, the strength of the buffer is no more than 300 mM (e.g., at most 200 mM, at most 100 mM, at most 90 mM, at most 80 mM, at most 70 mM, at most 60 mM, at most 50 mM, at most 40 mM, at most 30 mM, at most 20 mM, at most 10 mM, at most 5 mM, at most 1 mM).

In some aspects, the cells of the composition are in solution, e.g., aqueous solution. In some aspects, the cells of the composition are cryopreserved.

Routes of Administration

In some embodiments, the pharmaceutical composition comprising the multipotent stem cells, TM cells, corneal keratocytes, neural cells or adipocytes is formulated for parenteral administration, intraanterior chamber administration, intraschlemm's canal administration, intravitreous administration, subconjunctival administration, subcutaneous administration, intravenous administration, intramuscular administration, or intra-arterial administration. In exemplary aspects, the pharmaceutical composition is formulated fro implantation or injection. In other embodiments, the pharmaceutical composition is administered via nasal, spray, oral, or aerosol administration.

Methods of administering stem cells are known in the art. see, for example, any of U.S. Pat. Nos. 5,423,778, 5,550,050, 5,662,895, 5,800,828, 5,800,829, 5,811,407, 5,833,979, 5,834,001, 5,834,029, 5,853,717, 5,855,619, 5,906,827, 6,008,035, 6,012,450, 6,049,026, 6,083,523, 6,206,914, 6,303,136, 6,306,424, 6,322,804, 6,352,555, 6,368,612, 6,479,283, 6,514,522, 6,534,052, 6,541,024, 6,551,338, 6,551,618, 6,569,147, 6,579,313, 6,599,274, 6,607,501, 6,630,457, 6,648,849, 6,659,950, 6,692,738, 6,699,471, 6,736,799, 6,752,834, 6,758,828, 6,787,357, 6,790,455, 6,805,860, 6,852,534, 6,863,900, 6,875,441, 6,881,226, 6,884,427, 6,884,428, 6,886,568, 6,918,869, 6,933,281, 6,933,286, 6,949,590, 6,960,351, 7,011,828, 7,031,775, 7,033,345, 7,033,603, 7,049,348, 7,070,582, 7,074,239, 7,097,832, 7,097,833, 7,135,172, 7,145,055, 7,157,080, 7,166,280, 7,176,256, 7,244,242, 7,452,532, 7,470,425, and 7,494,644, each of which are incorporated by reference in their entirety.

Parenteral

In some embodiments, the pharmaceutical composition described herein is formulated for parenteral administration. For purposes of the invention, parenteral administration includes, but is not limited to, intravenous, intraanterior chamber administration, intraschlemm's canal administration, intravitreous administration, subconjunctival administration, intraarterial, intramuscular, intracerebral, intracerebroventricular, intracardiac, subcutaneous, intraosseous, intradermal, intrathecal, intraperitoneal, intravesical, and intracavernosal injections or infusions.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The pharmaceutical composition are in various aspects administered via a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxalane-4-methanol, ethers, poly (ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which are optionally used in parenteral formulations include petroleum, animal, vegetable, or synthetic oils. Specific examples of oils include peanut, soybean, sesame, cottonseed, corn, olive, petrolatum, and mineral. suitable fatty acids for use in parenteral formulations include oleic acid, stearic acid, and isostearic acid. Ethyl oleate and isopropyl myristate are examples of suitable fatty acid esters.

The parenteral formulations in some embodiments contain preservatives or buffers. In order to minimize or eliminate irritation at the site of injection, such compositions optionally contain one or more nonionic surfactants having a hydrophile-lipophile balance (HLB) of from about 12 to about 17. The quantity of surfactant in such formulations will typically range from about 5% to about 15% by weight. suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations are in various aspects presented in unit-dose or multi-dose sealed containers, such as ampoules and vials, and can be stored in a cryopreserved condition along with a freezing agent, e.g., dimethyl sulfoxide (DMSO).

Injectable formulations are in accordance with the invention. The requirements for effective pharmaceutical carriers for injectable compositions are well-known to those of ordinary skill in the art (see, e.g., Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed., pages 622-630 (1986)).

In some embodiments, the cells of the isolated populations are administered via a cell delivery matrix. The cell delivery matrix in certain embodiments comprises any one or more of polymers and hydrogels comprising collagen, fibrin, chitosan, MATRIGEL, polyethylene glycol, dextrans including chemically crosslinkable or photocrosslinkable dextrans, and the like. In certain embodiments, the cell delivery matrix comprises one or more of: collagen, including contracted and non-contracted collagen gels, hydrogels comprising, for example, but not limited to, fibrin, alginate, agarose, gelatin, hyaluronate, polyethylene glycol (PEG), dextrans, including dextrans that are suitable for chemical crosslinking, photocrosslinking, or both, albumin, polyacrylamide, polyglycolyic acid, polyvinyl chloride, polyvinyl alcohol, poly(n-vinyl-2-pyrollidone), pmy(2-hydroxy ethyl methacrylate), hydrophilic polyuretlianes, acrylic derivatives, pluronics, such as polypropylene oxide and polyethylene oxide copolymer, or the like. The fibrin or collagen in certain embodiments are autologous or allogeneic with respect to the patient.

The matrix in some instances comprises non-degradable materials, for example, but not limited to, expanded polytetrafluoroethylene (ePTFE), polytetrafluoroethylene (PTFE), polyethyleneterephthaiate (PET), poly(butylenes terephthalate (PBT), polyurethane, polyethylene, polycabonate, polystyrene, silicone, and the like, or selectively degradable materials, such as poly (lactic-co-glycolic acid; PLGA), PLA, or PGA. (See also, Middleton et al., Biomaterials 21:2335 2346, 2000; Middleton et al., Medical Plastics and Biomaterials, March/April 1998, at pages 30 37; Handbook of Biodegradable Polymers, Donib, Kost, and Domb, eds., 1997, Harwood Academic Publishers, Australia; Rogalla, Minim. Invasive Surg. Nurs. 11:6769, 1997; Klein, Facial Plast. Surg. Clin. North Amer. 9:205 18, 2001; Klein et al., J. Dermatol. Surg. Oncol. 1 1:337 39, 1985; Frey et al., J. Urol. 154:812 15, 1995; Peters et al., J. Biomed. Mater. Res. 43:422 27, 1998; and Kuijpers et al., 3. Biomed. Mater. Res. 51:13645, 2000).

In exemplary aspects of the composition, the cells are in a matrix, capsule or gel. In exemplary aspects, the matrix, capsule or gel is implantable.

The pharmaceutical composition comprising the isolated populations of multipotent stem cells, TM cells, corneal keratocytes, or neural cells, in certain embodiments, comprises any of the components of a cell delivery matrix, including any of the components described herein.

Dose

For purposes herein, the amount or dose of the pharmaceutical composition administered to a subject are sufficient to effect, e.g., a therapeutic or prophylactic response, in the subject or animal over a reasonable time frame, For example, the dose of the pharmaceutical composition is sufficient to treat or prevent a medical condition as further described herein (e.g., glaucoma), in a period of from about 1 to 4 days or longer, e.g., 5 days, 6 days, 1 week, 10 days, 2 weeks, 16 to 20 days, or more, from the time of administration. In certain embodiments, the time period is even longer. Cell based therapies of the present disclosures have potential to provide sustained or permanent benefit. The dose is determined by the efficacy of the particular pharmaceutical composition and the condition of the animal (e.g., human), as well as the body weight of the animal (e.g., human) to be treated.

Many assays for determining an administered dose are known in the art. In some embodiments, an assay which comprises comparing the extent to which multipotent stem cells are localized to the TM of an eye upon administration of a given dose of such multipotent stem cells to a mammal among a set of mammals of which is each given a different dose of the multipotent stem cells is used to determine a starting dose to be administered to an animal. The extent to which multipotent stem cells are localized to a TM upon administration of a certain dose can be assayed by methods known in the art, including, for instance, the methods described herein.

Additionally or alternatively, an assay which comprises comparing the extent to which a particular dose of multipotent stem cells cause attenuation of a medical condition as further described herein (e.g., glaucoma), a decrease in intraocular pressure, an increase in TM cellularity, or increase in aqueous humor outflow from the eye, can be used to determine a starting dose to be administered to a mammal.

The dose of the pharmaceutical composition also will be determined by the existence, nature and extent of any adverse side effects that might accompany the administration of a particular pharmaceutical composition. Typically, the attending physician will decide the dosage of the pharmaceutical composition with which to treat each individual patient, taking into consideration a variety of factors, such as age, body weight, general health, diet, sex, therapeutic agent(s) of the pharmaceutical composition to be administered, route of administration, and the severity of the condition being treated. By way of example and not intending to limit the invention, the dose of the pharmaceutical composition can be such that at least about $0.5 \times 10^6$ (e.g., at least or about $10^4$, $10^5$, $10^6$, $10^7$, $10^8$) multipotent stem cells are administered to the patient.

Controlled Release Formulations

The pharmaceutical composition are in certain aspects modified into a depot form, such that the manner in which the pharmaceutical composition is released into the body to which it is administered is controlled with respect to time and location within the body (see, for example, U.S. Pat. No. 4,450,150). Depot forms are in various aspects, an implantable composition comprising the therapeutic or active agent(s) and a porous or non-porous material, such as a polymer, wherein the multipotent stem cells, TM cells, corneal keratocytes, neural cells or. adipocytes are encapsulated by or diffused throughout the material and/or degradation of the non-porous material. The depot is then implanted into the desired location within the body and the cells are released from the implant at a predetermined rate.

Accordingly, the pharmaceutical composition in certain aspects is modified to have any type of in vivo release profile. In some aspects of the invention, the pharmaceutical composition is an immediate release, controlled release, sustained release, extended release, delayed release, or biphasic release formulation. In some aspects, the pharmaceutical composition is formulated for sustained, continuous release, e.g., formulated for continuous release of the (same amount of) cells over a sustained period of time, including but not limited to at least $10^3$, $10^4$, $10^5$, $10^6$, $10^7$, $10^8$, $10^9$, $10^{10}$, $10^{11}$, $10^{12}$ cells released from the composition and into the subject over 1 hour, 2 hours, 3 hours, 4 hours, 5 hours, 6 hours, 7 hours, 8 hours, 9 hours, 10 hours, 11 hours, 12 hours, 24 hours, 48 hours, 36 hours, 72 hours, 5 days, 6 days, 1 week, 2 weeks, 3 weeks, 1 month.

Conjugates

In some embodiments of the present disclosures, the cells or the isolated populations of cells are attached or linked to a second moiety, such as, for example, a therapeutic agent or a diagnostic agent. The cells (e.g., multipotent stem cells) in some embodiments act as a targeting agent, since the cells are able to specifically localize to the TM. Accordingly, the present disclosures provide in one aspect a composition comprising a conjugate comprising multipotent stem cells attached to a therapeutic agent or a diagnostic agent. Suitable therapeutic agents and diagnostic agents for purposes herein are known in the art and include, but are not limited to, any of those mentioned herein. In alternative embodiments, the cells are conjugated into a matrix and the matrix is conjugated to a second moiety, such as, for example a therapeutic or diagnostic agent.

Combinations

In some embodiments, the multipotent stem cells, T1Vi cells, corneal keratocytes, neural cells or adipocytes of the isolated populations provided herein are administered alone, and in alternative embodiments, the multipotent stem cells, TM cells, corneal keratocytes, neural cells or adipocytes of the isolated populations provided herein are administered in combination with another therapeutic agent, e.g., another cell of the present disclosures but of a different type (e.g., a combination of multipotent stem cells, TM cells, corneal keratocytes, neural cells and/or adipocytes), or another therapeutic which is known to achieve the same effect as the cells of the isolated populations or which are known to aid in the growth, survival, expansion, localization, stability, prevention of rejection, therapeutic index, bioefficacy, of the cells of the isolated population. In exemplary embodiments, the cell or isolated population provided herein is administered simultaneously as the other therapeutic agent. In alternative embodiments, the cell or isolated population provided herein is administered either before or after the other therapeutic agent.

In some aspects, the other therapeutic agent is an anti-glaucoma agent, including, but not limited to: a beta blocker (e.g., betaxolol, carteolol, levobunolol, metipranolol, timolol); an alpha-2-agonist (e.g., apraclonidine, brimonidine); a carbonic anhydrase inhibitor (e.g., acetazolamide, methazolamide, brinzolamide, dorzolamide), a prostaglandin (e.g., bimatoprost, latanoprost, travoprost, unoprostone); a miotic (e.g., carbachol, echothiophate, and pilocarpine), a combination medication (e.g., Cosopt (timolol and dorzolamide)).

In some aspects, the isolated populations or cells are administered in conjunction with an anti-glaucoma therapeutic procedure, including a laser surgery, e.g. laser trabeculoplasty, or a glaucoma surgery, e.g., incisional glaucoma surgery, or implantation of a glaucoma drainage device (e.g., glaucoma implant). The laser trabeculoplasty in some aspects is a selective laser trabeculoplasty, a laser peripheral iridotomy, a laser peripheral iridoplasty, or a laser cyclophotocoagulation.

Uses

The present disclosures additionally provide uses of the isolated populations of multipotent stem cells, TM cells, corneal keratocytes, neural cells or adipocytes. In exemplary embodiments, the isolated populations, or composition comprising the same, wherein the cells of the isolated population are multipotent stem cells or TM cells, are used in a method of decreasing intraocular pressure in an eye. The method comprises administering to a subject in need thereof the isolated population, or composition comprising the same, in an amount effective to decrease the intraocular pressure in the eye. Methods of assaying intraocular pressure in an eye are known in the art, and include, but not limited to, measurement of pressure with a tonometer, e.g., a Goldmann tonometer.

In other exemplary embodiments, the isolated populations, or composition comprising the same, wherein the cells of the isolated population are multipotent stem cells or TM cells, are used in a method of increasing cell density in the trabecular meshwork of an eye. The method comprises administering to a subject in need thereof the isolated population, or composition comprising the same, in an amount effective to increase cell density in the trabecular meshwork of an eye. Methods of assaying cell density or cellularity in the TM of an eye are known in the art. Suitable methods include, but not limited to, immunohistochemistry, microscopy (e.g., confocal), and the methods described in Alvarado et al., Invest Ophthamol Vis Sci 21(5): 714-727 (1981), Alvarado et al., Ophthamology 91(6): 564-579 (1984); and Murphy et al., Invest Ophthamol Vis Sci 25(3): 312-322 (1984).

In yet other exemplary embodiments, the isolated populations, or composition comprising the same, wherein the cells of the isolated population are multipotent stem cells or TM cells, are used in a method of increasing outflow of aqueous humor from the eye. The method comprises administering to a subject in need thereof the isolated population, or composition comprising the same, in an amount effective to increase outflow of aqueous humor from the eye. Methods of assaying outflow of aqueous humor from an eye are known in the art and include but not limited the tonographic technique described in Grant, Arch Ophthal 44(2): 204-214 (1950), Toris et al., GlaucomA Today, pages 15-22 (September/October 2007), and Brubaker, Trans Am Ophthalmol Soc 80: 391-474 (1982).

With regard to the above methods, the increase or decrease achieved upon administration of the cells of the isolated populations, or compositions comprising the same, may be any level of increase or decrease. For example, the method of decreasing intraocular pressure in some aspects achieves at least or about a 10% decrease (e.g., at least or about a 20% decrease, at least or about a 30% decrease, at least or about a 40% decrease, at least or about a 50% decrease, at least or about a 60% decrease, at least or about a 70% decrease, at least or about a 80% decrease, at least or about a 90% decrease, at least or about a 95% decrease), as compared to a control level. The control level in exemplary aspects is the level of the intraocular pressure in subjects to which cells were (or the composition was) not administered or the level of the intraocular pressure exhibited by the subject before administration of the cells or composition. In some aspects, the method of decreasing intraocular pressure achieves a decrease, such that intraocular pressure is substantially restored to normal levels. Also, for example, the method of increasing aqueous humor outflow in some aspects achieves at least or about a 10% increase (e.g., at least or about a 20% increase, at least or about a 30% increase, at least or about a 40% increase, at least or about a 50% increase, at least or about a 60% increase, at least or about a 70% increase, at least or about a 80% increase, at least or about a 90% increase, at least or about a 95% increase), as compared to a control level. The control level in exemplary aspects is the level of the aqueous humor outflow in subjects to which cells were (or the composition was) not administered or the level of the aqueous humor outflow exhibited by the subject before administration of the cells or composition. In some aspects, the method of increasing aqueous humor outflow achieves an increase, such that aqueous humor outflow is substantially restored to art-recognized normal levels. Further, for example, the method of increasing cellularity or cell density of a TM in some aspects achieves at least or about a 10% increase (e.g., at least or about a 20% increase, at least or about a 30% increase, at least or about a 40% increase) or at least or about a 50% increase (e.g., at least or about a 60% increase, at least or about a 70% increase, at least or about a 80% increase, at least or about a 90% increase, at least or about a 95% increase), as compared to a control level. The control level in exemplary aspects is the level of TM cellularity or cell density in subjects to which cells were (or the composition was) not administered or the level of TM cellularity of cell density exhibited by the subject before administration of the cells or composition. In some aspects, the method of increasing TM cellularity or cell density achieves an increase, such that the cellularity or cell density is substantially restored to normal levels. As used herein "normal levels" refers to a level within a range of intraocular pressure, range of aqueous humor outflow, or range of TM cellularity or cell density, which range is considered by a physician, e.g., an ophthalmologist, as representative of a healthy subject or an undiseased subject. In exemplary aspects, a normal level of intraocular pressure as measured by a Goldmann tonometer is a measure within the range of 10 to 22.

The present disclosures furthermore provide a method of treating or preventing a medical condition in a subject in need thereof. The medical condition in some embodiments is a medical condition that is caused by or associated with decreased cell density in the trabecular meshwork, increased intraocular pressure in an eye, decreased outflow of aqueous humor from the eye, or a combination thereof. The method comprises administering to a subject in need thereof the isolated population, or composition comprising the same, wherein the cells of the isolated population are multipotent stem cells or TM cells, in an amount effective to treat or prevent the medical condition.

As used herein, the terms "treat," and "prevent" as well as words stemming therefrom, do not necessarily imply 100% or complete treatment or prevention. Rather, there are varying degrees of treatment or prevention of which one of ordinary skill in the art recognizes as having a potential benefit or therapeutic effect. In this respect, the methods of treatment or prevention provided herein can provide any amount of any level of treatment or prevention of a medical condition in a subject. Furthermore, the treatment or prevention provided by the methods of treatment or prevention provided herein in same aspects includes treatment or prevention of one or more conditions or symptoms of the medical condition being treated or prevented. Also, for purposes herein, "prevention" in some aspects encompasses delaying the onset of the medical condition, or a symptom or condition thereof.

In exemplary aspects, the medical condition is glaucoma. In some aspects, the glaucoma is open-angle glaucoma, angle-closure glaucoma, congenital glaucoma, or secondary glaucoma. Methods of diagnosing or monitoring glaucoma are known in the art and include but not limited to gonioscopy-mediated examination, tonometry, optic nerve imaging, papillary reflex response, retinal examination, slit lamp examination, visual acuity, visual field measurement.

In exemplary aspects, the presently disclosed method treats or prevents a symptom of glaucoma. In exemplary aspects, the symptom of glaucoma is tunnel vision, severe eye pain, cloudy vision, decreased vision, nausea, vomiting, halos around lights, red eye, cloudiness of the front of the eye, enlargement of the eye, light sensitivity, tearing.

Because glaucoma is the second most common cause of blindness in the United States, treatment of glaucoma may be considered as a prevention or delay or slowing of blindness. Accordingly, the medical condition prevented by the method of the present disclosures in exemplary aspects is blindness.

In alternative aspects, the medical condition is one that is caused by a decrease in keratocytes in a subject or in a tissue thereof. In some aspects, the decrease in keratocytes is due to an increase in keratocyte degeneration, keratocyte cell injury, or keratocyte cell death (e.g., apoptosis, necrosis). The method comprises administering to a subject in need thereof the isolated population, or composition comprising the same, wherein the cells of the isolated population are multipotent stem cells or corneal keratocytes, in an amount effective to treat or prevent the medical condition.

In alternative aspects, the medical condition is one that is caused by a decrease in neural cells in a subject or in a tissue thereof. In some aspects, the decrease in neural cells is due to an increase in neural cell degeneration, neural cell cell injury, or neural cell cell death (e.g., apoptosis, necrosis). The method comprises administering to a subject in need thereof the isolated population, or composition comprising the same, wherein the cells of the isolated population are multipotent stem cells or neural cells, in an amount effective to treat or prevent the medical condition.

In alternative aspects, the medical condition is one that is caused by a decrease in adipocytes in a subject or in a tissue thereof. In some aspects, the decrease in adipocytes is due to an increase in adipocyte degeneration, adipocyte cell injury, or adipocyte cell death (e.g., apoptosis, necrosis). The method comprises administering to a subject in need thereof the isolated population, or composition comprising the same, wherein the cells of the isolated population are multipotent stem cells or adipocytes, in an amount effective to treat or prevent the medical condition.

In exemplary aspects of the methods of treatment or prevention provided herein, the administered cells may be obtained through any of the methods of obtaining multipotent stem cells or of obtaining differentiated cells described herein. In relation to the subject receiving the cells, the source of the cells administered to the subject may be any source, as described herein. In some aspects, the source of the cells is a mammal. In specific aspects, the source of the cells is a human. In further aspects, the species of the source of cells is the same species as the subject to which the cells are administered. In some aspects, the source of the cells is the subject to which the cells are administered such that the cells are "autologous" to the subject. In some embodiments, the source of the cells is different from the subject, but the source and patient are of the same species, such that the cells are considered as "allogeneic" cells with reference to the subject.

Subjects

With regard to the present disclosures, the subject may be any living organism, e.g., an organism comprising a TM. In exemplary aspects, the subject is a mammal. As used herein, the term "mammal' refers to any vertebrate animal of the mammalia class, including, but not limited to, any of the monotreme, marsupial, and placental taxis. In some embodiments, the mammal is one of the mammals of the order Rodentia, such as mice and hamsters, and mammals of the order Logomorpha, such as rabbits. In certain embodiments, the mammals are from the order Carnivora, including Felines (cats) and Canines (dogs). In certain embodiments, the mammals are from the order Artiodactyla, including Bovines (cows) and S wines (pigs) or of the order Perssodactyla, including Equines (horses). In some instances, the mammals are of the order Primates, Ceboids, or Simoids (monkeys) or of the order Anthropoids (humans and apes). In particular embodiments, the mammal is a human.

Kits

The present disclosures furthermore provide kits comprising any of the isolated populations of multipotent stem cells, TM cells, corneal keratocytes, neural cells or adipocytes, described herein, or any of the compositions comprising the cells or isolated populations described herein. In some aspects, the cells of the kit are provided in a container, e.g., a vial, tube, plate, well, flask, and the like. In certain aspects, the cells of the kit are provided in a cryopreserved form. In alternative aspects, the cells of the kit are provided in a ready to use form (e.g., are in solution) and are not cryopreserved. In some aspects, the cells of the kit are provided in a device for administration of the cells to a subject. In some aspects, the cells are provided in an intravenous bag, a syringe, a matrix, e.g., an implantable matrix, a capsule, e.g., an implantable capsule, ready for administration to a subject. In some aspects, the kit comprises a device for administration.

In exemplary aspects, the kit comprises a set of instructions for use in accordance with any of the methods described herein. The set of instructions, in some embodiments, comprise instructions for using the cells in a method of obtaining an isolated population of TM cells, corneal keratocytes, neural cells or adipocytes. The set of instructions, in alternative embodiments, comprise instructions for using the cells in a method of decreasing intraocular pressure in an eye, increasing cell density in the TM of an eye, or increasing outflow of aqueous humor from an eye. The set of instructions, in other embodiments, comprise instructions for using the cells in a method of treating or preventing a medical condition, e.g., a medical condition described herein. In exemplary aspects, the kit comprises instructions for administration of the composition comprising the cells to a subject.

Devices

The present disclosures furthermore provides a device comprising any of the isolated populations of multipotent stem cells, TM cells, corneal keratocytes, neural cells or adipocytes, described herein, or any of the compositions comprising the cells or isolated populations described herein. In exemplary aspects, the device is a device for administration to a subject. Accordingly, in some aspects, the device is an intravenous bag, a syringe, a matrix, e.g., an implantable matrix, or a capsule, e.g., an implantable capsule.

The following examples are given merely to illustrate the present invention and not in any way to limit its scope.

Example 1

The following materials and methods were used in the studies described in Example 2.

Antibodies

Primary antibodies used in the studies described below included ABCG2 (Clone BXP-21; Chemicon International, Temecula, Calif.), Pax6 (Covance, Princeton, N.J.), mucin 1, ankyrin G, AQP1, MGP, TIMP-3, myocilin (Santa Cruz Biotechnology, Inc., Santa Cruz, Calif.), CHI3L1 (R&D Systems, Minneapolis, Minn.), beta-tubulin III, glial fibrillary acidic protein (GFAP) (Chemicon International), and NF200 against neurofilament protein (Sigma-Aldrich, St. Louis, Mo.).

Secondary antibodies for Western blotting were purchased from Santa Cruz Biotechnology, Inc. (Santa Cruz, Calif.). For fluorescent staining, anti-mouse Alexa 488, anti-rabbit Alexa 488, anti-rabbit Alexa 647, nuclear dye DAPI, and Vybrant DiQ were obtained from Molecular Probes, Inc. (Eugene, Oreg.).

Table 1 provides further details on the types of antibodies used.

TABLE I

| Antibody | Type | Source | Catalog# |
|---|---|---|---|
| ABCG2 | Mouse monoclonal | Chemicon | MAB4146 |
| Pax6 | Rabbit polyclonal | Covance | PRB278P |
| Nestin | Rabbit polyclonal | Chemicon | AB5922 |
| Mucin 1 | Mouse monoclonal | Santa Cruz | Sc-7313 |
| Ankyrin G | Mouse monoclonal | Santa Cruz | Sc-12719 |
| AQP1 | Rabbit polyclonal | Santa Cruz | Sc-20810 |
| MGP | Mouse monoclonal | Santa Cruz | Sc-81546 |
| CHI3L1 | Goat polyclonal | R&D | AF2599 |
| TIMP3 | Mouse monoclonal | Santa Cruz | Sc-101578 |
| NCAM | Mouse monoclonal | BD | 559049 |
| Myocilin | Rabbit polyclonal | Santa Cruz | Sc-20976 |

Primary Cell Culture

Human corneas were obtained from the Center for Organ Recovery & Education Pittsburgh, Pa.). Donor human corneas including sclera rim and hence trabecular meshwork (TM) that were not usable for transplantation, or corneoscleral rims after surgery were used for experiments. After careful removal of the iris, a cut was made through the inner edge of Schwalbe's line and the pigmented TM tissue was peeled.

For explant cultures, the tissue was cut into pieces and put in either a 35 mm dish or a 25 cm² flask. Medium was added and was left undisturbed for 10-14 days to let the cells migrate out from the explants.

For attachment cell cultures, the dissected TM tissue was digested in 0.3 mg/ml collagenase type L in Dulbecco's modified Eagle's medium (DMEM) containing albumin and glutamine overnight at 37° C. incubator. After digestion, the cells were filtered through a 70 gm mesh to remove the tissue and were washed in the same medium twice. Cells were seeded at $2 \times 10^4$ cells/cm² in TM stem cell growth medium (SCGM), described below.

For both cultures, the cells were passaged when they reached about 80-90% confluence by trypsinization and seeding at $2 \sim 5 \times 10^3$ cells/cm2 in SCGM.

The primary TM cells were cultured in medium without fetal bovine serum and any growth factors to keep their TM cell characteristics as a control.

SCGM was made by supplementing OptiMEM-1 (Invitrogen Life Technologies, Carlsbad, Calif.) with 5% fetal bovine serum (Hyclone, Logan, Utah), 10 ug/mL epidermal growth factor (EGF; Upstate Biotechnologies, Lake Placid, N.Y.), 100 µg/mL bovine pituitary extract (Biomedical Technologies, Stoughton, Mass.), 20 ug/mL ascorbic acid (Sigma-Aldrich, St. Louis, Mo.), 200, g/mL calcium chloride (Sigma-Aldrich), 0.08% chondroitin sulfate (Sigma-Aldrich), 100 IU/ml penicillin, 100 µg/ml streptomycin, and 50 ug/ml gentamicin (Sigma-Aldrich).

Isolation of Stem Cells by Side Population Cell Sorting

After 2-3 passages, trypsinized cells were incubated at $1.0 \times 10^6$ cells per ml in pre¬ warmed DMEM with 2% FBS and 1004 DyeCycle Violet (DCV) for 100 minutes at 37° C. To inhibit ABCG2-mediated efflux of DCV dye, cells were preincubated for 20 minutes with 25 µg/ml fumitremorgin C(FTC) before DCV incubation. After staining, the cells were washed twice in Hanks' balanced salt solution (HBSS) with 2% FBS and then stored in cold HBSS with 2% FBS on ice. Immediately before sorting, 2 ug/ml propidium iodide was added to identify nonviable cells for flow cytometric analysis. Cells were analyzed on a Beckton Dickinson & Co. (BD) fluorescence activated cell sorting (FACS) Aria flow cytometer high-speed cell sorter, using 405-nm excitation. Cells demonstrating a reduced fluorescence of both blue (450 nm) and red (670 nm), which cells are considered as a "side population," were collected. Dead cells stained with propidium iodide were omitted from the population.

Isolation of Stem Cells by Clonal Expansion

Clonogenic assays were performed by limiting dilution (0.3 cells/well in 96-well plate) followed by subcultivation. After obtaining a substantial number of cloned cells, a gene expression profile was obtained to determine which clones were undifferentiated ceils. The clones with expression of stem cell markers were passaged for further experiments.

Multipotency of TM Stem Cells

To analyze their ability to differentiate into different types of cells, the TM stem cells (TMSCs) were cultured under the following different conditions:

Corneal keratocytic differentiation: Aliquots of TMSCs $(2.5 \times 10^5)$ were collected in a conical-bottom 15-mL tube, centrifuged at 1500 rpm (400 g) for 5 minutes to form a pellet. The pellets of each aliquot were cultured in SCGM for 3 days and then transferred into keratocyte differentiation medium (KDM: advanced MEMTM (Invitrogen) with 10 mg/mL fibroblast growth factor 2 [FGF2] and 0.5 mM ascorbic acid-2-phosphate), which was changed every 3 days for up to 3 weeks.

Neural induction: TMSCs were seeded onto FNC Coating Mix® (AthenaES, Baltimore, Md.) coated 35 mm dishes at 10,000 cells/cm$^2$ in neural differentiation medium (NDM) containing Advanced D-MEM with 10 mg/ml epithelial growth factor, 10 mg/ml fibroblast growth factor and I μM all-trans retinoic acid, 100 IU/ml penicillin, 100 μg/ml streptomycin, and 50 μg/ml gentamicin. The medium was changed every 3 days and fresh all-trans retinoic acid was added each time. The cells were cultured for 3 weeks for induction.

Adipogenic differentiation: TMSCs were seeded onto 1% gelatin (Sigma-Aldrich) coated 35 mm dishes at 20,000 cells/cm2 in adipogenic differentiation medium (ADM) consisting of DMEM-Low glucose with 10% FBS, 1 μmM dexamethasone, 0.5 μM methyl-isobutylxanthine, 10 μg/ml recombinant human insulin, 200 μM indomethacin, 100 IU/ml penicillin, 100 μg/ml streptomycin, and 50 μg/ml gentanxicin. The cells were cultured in ADM for 7 days, then changed to adipogenic maintenance medium (AMM) containing of DMEM with 15% FBS, 10 μg/ml recombinant human insulin, 100 IU/ml penicillin, 100 μg/ml streptomycin, and 50 μg/ml gentamicin for 4 days. The medium was changed back to ADM for another 7 days, then changed to AMM for another 4 days and the cells were fixed for histology or lysed for RNA.

Trabecular meshwork cell differentiation: Bovine aqueous humor (AH) was collected from enucleated bovine eyes by inserting a 26-gauge needle through the cornea limbus and positioning its tip into the center of the anterior chamber. AH was pooled and centrifuged at 10,000 g for 1 hour at 4° C. to pellet any pigment or cellular debris followed by filtering through 0.22 μm to get rid of any potential contaminations. The AH was kept at −80° C. for later use. TM cell differentiation was induced by culturing the TMSC in 50% stem cell growth medium (SCGM) with 50% AH, 100% AH, or DMEM/F12 plus 10% FBS. The TMSC were cultured in those TM differentiation media and the media were changed every 3 days for up to 10 days.

Phagocytosis assay: This assay was performed following the procedures described by Zhang et al 14. In brief, Alexa 488 conjugated *Staphylococcus aureus* bioparticles (heat- or chemically killed) (Molecular Probes, Inc. Eugene, Oreg.) were incubated with *S. aureus* bioparticle opsonizing reagent (purified rabbit polyclonal IgG antibody; Molecular Probes) at 37 C for 1 hr for enhancing the uptake of these particles. The differentiated TM cells were incubated with rabbit IgG opsonized Alexa 488 conjugated *S. aureus* bioparticles at a ratio of 50 bioparticles per cell at 37 C for 1 hr. After incubation, the cells were fixed with 4% paraformaldehyde solution for 15 min at room temperature (RT) and incubated with Alexa Flour 546 goat anti-rabbit IgG secondary antibody at RT for 1 hr. The secondary antibody was believed to bind to the extracellular bioparticles opsonized with rabbit IgG, so that the unphagocytosed bioparticles would be excluded when counting. Cell nuclei were labeled with DAPI at 1 μg/ml for 10 min. Cellular phagocytosis of bioparticles, DAPI nuclei and cellular morphology were visualized and imaged with an Olympus FluoView FV 1000 confocal microscope. The number of phagocytic bioparticles were quantified by counting individual TM cells (DAPI stained nuclei) and total bioparticles ingested by these TM cells. At least ten individual views per condition were counted and averaged. The data were analyzed statistically by otte-way ANOVA followed by the lukey post-test to assess the significance of differences.

Quantitative Reverse Transcription-Polymerase Chain Reaction (qPCR)

The anterior part of human eye including the cornea, TM and part of the sclera, was stabilized in RNALater (Ambion, Austin, Tex.) overnight. The tissues of the TM, the TM insert and the corneal stroma, were separated under microscope and then were homogenized. The tissues or cultured cells were lysed with RLT buffer in the RNeasy mini kit (Qiagen, Valencia, Calif.) and RNAs were isolated following the manufacturer's instructions treated with DNAse I (Ambion) and concentrated by alcohol precipitation. cDNAs were transcribed from the RNAs using SuperScript II reverse transcriptase (Invitrogen). qPCR of cDNAs was. performed by direct dye binding (SYBR Green; Applied Biosystems) as previously described. 15 Primers for SYBR assays were designed using online software (Primer 3) with the sequences shown in Table 2.

TABLE 2

| Gene Name | DNA Sequence | | Seq. ID No. |
|---|---|---|---|
| 18S Ribosomal | Forward: | CCCTGTAATTGGAATGAGTCCAC | 1 |
| | Reverse: | GCTGGAATTACCGCGGCT | 2 |
| ABCG2 | Forward: | TGCAACATGTACTGGCGA.AGA | 3 |
| | Reverse: | TCTTCCACAAGCCCCAGG | 4 |
| Pax6 | Forward: | CAATCAAAACGTGTCCAACG | 5 |
| | Reverse: | TAGCCAGGTTGCGAAGAACT | 6 |
| CD73 | Forward: | GTTCCTGTAGTCCAGGCCTATG | 7 |
| | Reverse: | TCAGGAATGCTGCTGTTTAGAA | 8 |
| CD9Q | Forward: | CCAACTTCACCAGCAAATACAA | 9 |
| | Reverse: | CCAGTTTGTCTCTGAGCACTGT | 10 |
| CD 166 | Forward: | GTCTGCTCTTCTGCCTCTTGAT | 11 |
| | Reverse: | TCATATTTCCATTTGCCAAACA | 12 |
| CD 117 | Forward: | CGAGTTGGCCCTAGACTTAGAA | 13 |
| | Reverse: | CTTTGTGATCCGACCATGAGTA | 14 |
| Bmi1 | Forward: | GCCTTAACGCTGTGTGTATGAC | 15 |
| | Reverse: | ACCTGGAGATGCCAGAGAGTAG | 16 |
| OCT4 | Forward: | AAAGGGTGGGGGCAGGGGAG | 17 |
| | Reverse: AGTGTGTCTATCTACTGTGTCCCAGGC | | 18 |
| Notch1 | Forward: | AGTCTCTGCAGTGCTGGAAGTA | 19 |
| | Reverse: | CTTGCAGTACTGGTCGTACAGG | 20 |
| KLF4 | Forward: | ACCCTGGGTCTTGAGGAAGT | 21 |
| | Reverse: | TGCCTTGAGATGGGAACTCT | 22 |
| Muc 1 (Mucin 1) | Forward: | CCATTCCACTCCACTCAGGT | 23 |
| | Reverse: | CCACATGAGCTTCCACACAC | 24 |
| AnkG (Ankerin G) | Forward: | CATTCCTCCACGCAAGTGTA | 25 |
| | Reverse: | GTGGGTTGGCCAGTTTATGT | 26 |
| AQP1 (Aquaporin 1) | Forward: | CTGCACAGGCTTGCTGTATG | 27 |
| | Reverse: | TGTTCCTTGGGCTGCAACTA | 28 |
| MGP | Forward: GCCGCCTTAGCGGTAGTAAC TCTCTGCTGAGGGGATATGA | | 29 30 |
| CH13L1 | Forward: CCTTGACCGCTTCCTCTGTA GTGTTGAGCATGCCGTAGAG | | 31 32 |

TABLE 2-continued

| Gene Name | DNA Sequence | | Seq. ID No. |
|---|---|---|---|
| Kera (keratocan) | Forward: | ATCTGCAGCACCTTCACCTT | 33 |
| | Reverse: | CATTGGAATTGGTGGTTTGA | 34 |
| Myocilin | Forward: | AAGCCCACCTACCCCTACAC | 35 |
| | Reverse: | TCCAGTGGCCTAGGCAGTAT | 36 |
| ELAM1 | Forward: | ACACCTCCACGGAAGCTATG | 37 |
| | Reverse: | AATTGCAACCAGGTGTGTGTA | 38 |
| MMP1 | Forward: | TGGACCTGGAGGAAATCTTG | 39 |
| | Reverse: | AGAATGGCCGAGTTCATGAG | 40 |
| ap2 | Forward: | CATGGCCAAACCTAACATGA | 41 |
| | Reverse: | AATTCCTGGCCCAGTATGAA | 42 |
| Leptin | Forward: | TCCTGGATTCCTTTCCTTCA | 43 |
| | Reverse: | CAATCGAGGAGGGCAGAATA | 44 |

Amplification of 18S rRNA was performed for each cDNA (in triplicate) for normalization of RNA content. A negative control lacking cDNA was also included in each assay. Relative mRNA abundance was calculated as the Ct for amplification of a gene-specific cDNA minus the average Ct for 18S expressed as a power of 2(2-ΔΔCt). Three individual gene-specific values thus calculated were averaged to obtain mean±SD.

Animals

Female C57BL/6 mice (Charles River Laboratories International, Inc., Wilmington, Mass.), 9 weeks of age, were used in the experiments described below. AH experimental procedures were reviewed and approved by Institutional Animal Care and Use Committees and handled according to guidelines provided in the Association for Research in Vision and Ophthalmology Resolution on the Use of Animals in Ophthalmic and Vision Research.

TMSC Transplantation

At the fourth passage, the cloned TMSC cultured in SCGM were prelabeled with membrane dye Vybrant Di0 (Invitrogen) as described previously[16]. In brief, the cells were suspended in DMEM/F12 at 1×10$^6$ cells/ml and incubated with Di0 at 50 ug/ml for 20 minutes at 37° C. The cells were washed twice with DMEM/F-12 and resuspended in serum-free DMEM/F12 at 2.5×10$^4$ cells/μl for injection. Corneal fibroblasts (at passage 8) cultured in DMEM.F12 with 10% FBS served as controls.

TMSCs were transplanted into the anterior chamber of mice following the procedures of McKenna et al., J Immunol 169: 2630-5637 (2002) with subtle modifications. Briefly, all mice were anesthetized by i.p. injection of 2 mg of ketamine hydrochloride and 0.04 mg of xylazine (IVX Animal Health, Inc., St. Joseph, Mo.) in. 0.2 rnl of Dulbecco's phosphate buffered salt solution (PBS). The eyes were washed with PBS with antibiotics. The eyes were also anesthetized by topical drops of proparacaine HCl (Alcon Laboratories). The right eye of each mouse was used for stem cell or fibroblast injection and the left eye was used as control. The cornea was punctured by inserting a 30-gauge needle outside of the pupil area and parallel to the iris. Aqueous humor was allowed to flow out and was removed by an ophthalmic sponge (Microsponge; Alcon Laboratories). An air bubble was then introduced into the anterior chamber by injecting a 1.5 μl volume of air with a Hamilton micro syringe (Hamilton, Reno, Nev.) fitted with a 33-gauge beveled needle. Next, 50,000 TMSCs or fibroblasts in 2 μl of DMEM/F-12 was injected with a micro syringe fitted with a 33-gauge blunt needle (Hamilton). The air bubble seals the corneal puncture and prevents leakage. After injection, the eyes were treated once with gentamicin sulfate ophthalmic drops. The mice were sacrificed at 1 wk and 4 wks after transplantation. The mouse eyes were enucleated and fixed in 2% PFA at 4° C. overnight for histology, followed by either frozen in optimal cutting temperature embedding compound (Tissue-Tek OCT, Electron Microscopy Sciences, Hatfield, Pa.) and cut into 8 μm thick cryosections on a cryostat for immunofluorescent staining or stored at 4° C. in 50% glycerol and 50% PBS (v/v) for wholemount staining.

Histology

Cells cultured in plastic plates were rinsed briefly in PBS, fixed for 12-15 minutes in 3% paraformaldehyde (PFA) in PBS at room temperature, rinsed in PBS, and stored at 4° C. in 50% glycerol and 50% PBS (v/v) until stain. Cells cultured in pellets were rinsed and fixed as described above and then embedded in OCT compound and cut into 8 sections, stored at −80° C. until staining. PFA (2%) fixed mouse eyeballs were also embedded in OCT and cut into 8 mm sections for stain. Nonspecific binding was blocked with 10% heat-inactivated goat serum or 1% BSA and anti-mouse CD16/CD32 Fc γIII/II (BD Pharmingen) for mouse sections. Sections were incubated overnight at 4° C. with primary antibodies. After three washes, secondary antibodies were added followed by incubation for 2 hrs at room temperature. Samples were photographed using a confocal microscope (Olympus) with a 40× oil objective.

Oil Red O stain for adipogenic differentiation: Oil red O(Sigma-Aldrich) was prepared at 0.5% in isopropanol, diluted to 0.3% in water and filtered before use. Cells were stained with oil red O for 20 min and rinsed with 60% isopropanol followed by hematoxylin stain for nuclei. Bright-field micrography was performed with a 40× oil objective.

Wholemount stain: After fixation in 2% PFA and washed with PBS, the posterior part of the eyeball was removed from 1.5 mm posterior to the limbus including the lens and iris. The anterior part including the cornea and the TM were cut into half for wholemount stain and the cornea was cut in the middle to flatten the tissue. After blocking, the tissue was incubated with primary antibodies overnight at 4° C. Following 5 washes, tissue was incubated with fluorochrome-conjugated secondary antibodies with DAPI (Vector Laboratories) prior to confocal imaging.

Confocal Imaging of TM Whole Mounts

Images were acquired by sequential scanning to avoid fluorescence crossover on an Olympus Fluoview 100Qx confocal microscope. Z stacks through the tissue were acquired using ImageJ software. All image reconstructions were made using a MetaMorph (Molecular Devices; version: 7.5.4.0).

Example 2

Distribution of Stem Cells in Human TM Tissue.

Human tissue cryosections were stained with stem cell markers ABCG2, Pax6, Mucin 1, and Ankyrin G, as well as with TM markers AQP1, MGP, CHI3L1 and TIMP3.

The ATP-binding cassette transporter family 62 (ABCG2) is present at relatively high levels in undifferentiated human embryonic stem cells, and plays a protective role against toxins, drugs, or hypoxia(18). ABCG2 has also been identified as a specific marker for adult stem cells (15, 19-22). PAX6 is a homeobox transcription factor expressed in embryonic ocular precursor cells and epithelial cells (23) and this molecule may contribute to the stem cell phenotype as a proliferation moderator (24) Ankyrin G and Mucin1 are considered as markers for the stem cells of TM since they have been observed with high expression in Schlemm's canal cells (25) which are also called TM insert cells (26). Mucin 1 is a cell surface protein which functions as an interfacing protein to the aqueous fluid. The water channels aquaporin 1 (AQP1) has been detected to be present in the eye tissues of the corneal epitheliutn, the ciliary epithelium, the posterior iris epithelium and the trabecular meshwork endothelium (27) as well as in cultured human trabecular meshwork cells (1). The exact role of aquaporin 1 (AQP1) expression in TM and Schlemm's canal cell function has not yet been demonstrated, although it was hypothesized to influence osmotic permeability of the TM plasma membrane as well as the resting intracellular volume and, thus possibly paracellular permeability (28). Matrix Gla protein (MGP) encodes a protein involved in inhibition of calcification in cartilage and blood vessels; MGP has conserved the cation sensing mechanism present in vascular smooth muscle that responded to extracellular ionic calcium by upregulating its mRNA. So MGP plays a protective role in the TM and stress its position as an essential player at times of elevated pressure (29). Aqueous humor contains CHI3L1 which has a protective role against inflammation, extracellular matrix (ECM) remodeling and cell death in the outflow pathway (30). The matrix metalloproteinase (MMP) family and their tissue inhibitors, the TI.M1's, arc integrally involved in regulating the turnover of TM extracellular matrix (31). AQP1, MGP, CHI3L1 and TIMP 3 are considered as TM markers.

Figure 1B:
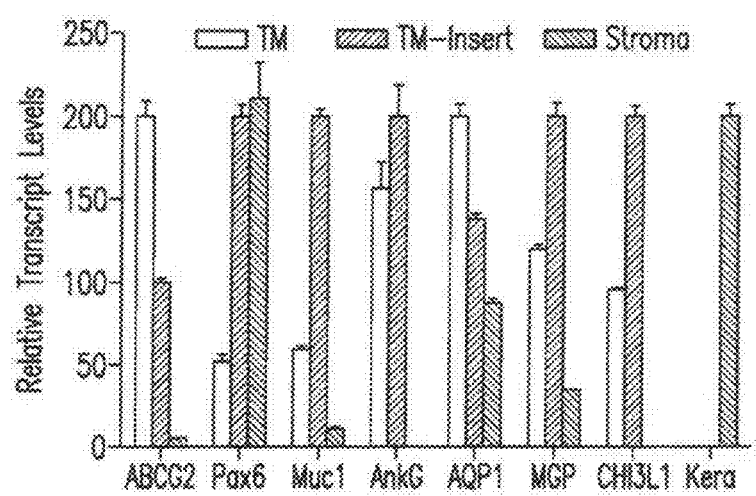

Immunofluorescent staining was observed in the TM tissue where the TM markers are expressed (FIG. 1A, right column) and some cells positive to the stem cell markers (FIG. 1A, left column) also were observed. The cells positive to stem cell markers were distributed throughout the TM tissue and not limited to any particular region of the TM. Quantitative RT-PCR was performed to compare gene expression of the cells from TM and insert region and the results demonstrated that there were no obvious differences in the gene expression pattern between the two regions of TM (FIG. 1B); no expression of the corneal stromal specific gene, keratocan, in TM and insert region indicates that the tissues do not contain keratocytes.

Isolation of Side Population Cells

Expression of ABCG2 has been implicated in the side population phenotype32. ABCG2 acts to remove Hoechst dye from cells, thus allowing isolation of cells as a "side population" (SP), in which ABCG2 is active, by use of flow cytometry (33, 34). Similarly, DyeCycle Violet (DCV) is a cell membrane permeable, fluorescent vital dye that intercalates into DNA and is a substrate for ABCG2-mediated efflux. DCV therefore is used to isolate SP cells on flow cytometry using violet lasers (35, 36) without the requirement for an ultraviolet laser for Hoechst 33342 emission.

Figure 2A:
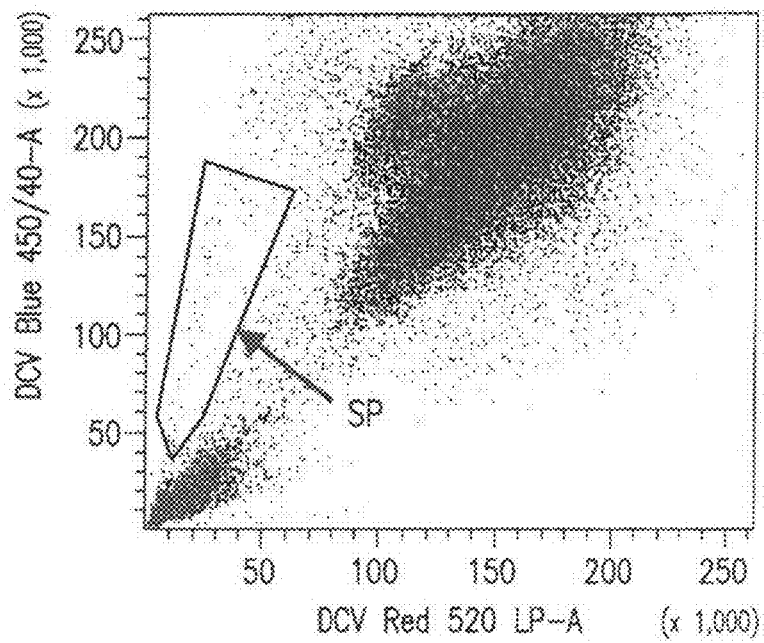
FIG. 2A-2B demonstrates an exemplary isolation and characteristics of Side Population cells.

The cultured cells were passaged in SCGM containing 5% FSS for 2-4 passages. After trypsinization, the cells were labeled with DCV for 100 min at 37° C., followed by cell sorting on a flow cytometry (FACSAria with FACSDIVA data analysis software; BD Biosciences) with violet lasers. FIG. 2A shows that the cultured TM cells contained a side population (the tail formed within the frame) which were collected by fluorescence activated cell sorting (FACS). To assess the purity of the collected cells, the collected cells were labeled with antibodies specific for one of the following stem cell markers: CD73, CD90, CD166, Bmi1, or antibodies specific for one of the TM cell markers: CHI3L1 and AQP1. The labeled cells were then analyzed via flow cytometry to determine the % labeled cells. The collected cells were 99.9% positive for expression of the stem cells marker CD73, 97.7% positive for expression of the stem cell marker CD9Q, 96.4% positive for expression of the stem cells marker CD166 and 97.8% positive for expression of the stem cell marker Bzni1. In contrast, the collected cells were only 10.9% positive for expression of the TM cell marker CHI3L1 and 2.63% positive for expression of the TM cell marker AQP1.

Figure 2B:
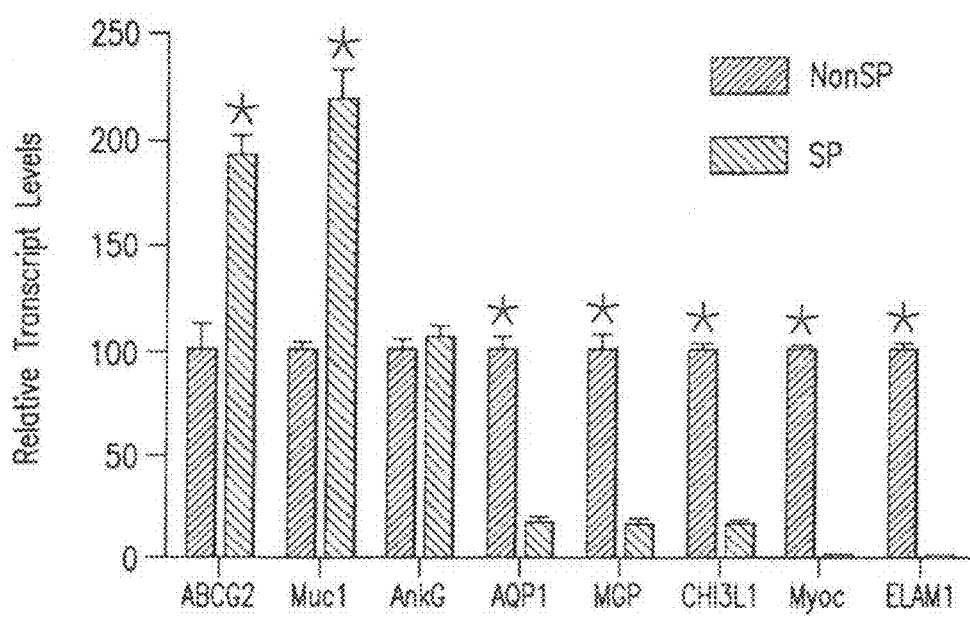

The isolated SP and non-SP cells were cultured in SCGM and at passage 8, the cells were lysed for extracting ruRNA. qPCR was done to compare the gene expression of SP and non-SP cells (FIG. 2B). The stem cell genes ABCG2 and mucin 1 (Muc1) of the SP cells was approximately 2-fold higher than that of the non-SP cells; the TM genes AQP1, MOP and CHI3L1 of the SP cells were approximately 4-fold lower as compared to that of the non-SP cells. SP cells demonstrated virtually no expression of the glaucomatous genes myocilin and ELAM-1. The differences are statistically significant ($p<0.05$) analyzed by one-tailed t-test. However, ankyrin G(AnkG) expression of SP was the same as that of non-SP cells.

Cultured TMSC Express Stem Cell Markers.

Figure 3K:
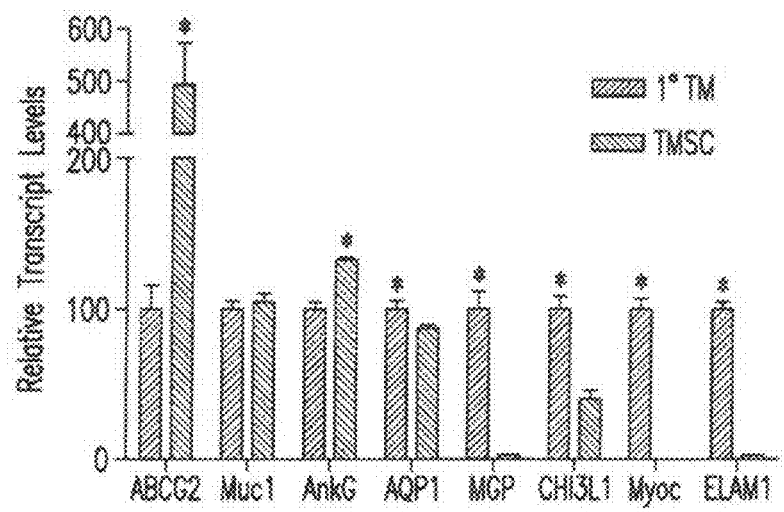
Figure 3L:
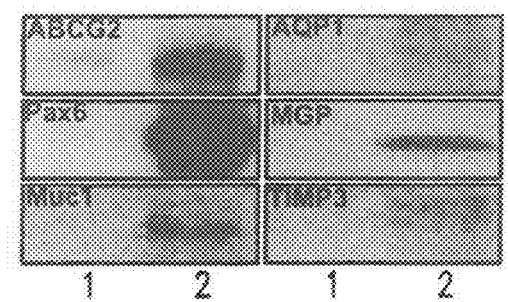

TMSC were cultured in SCGM for 4 passages and the primary TM cells were cultured in medium without fetal bovine serum and any growth factors to keep their TM cell characteristics as control. FIG. 3A-J show the immunofluorescent double staining on TMSC and primary TM cells with stem cell markers ABCG2, Pax6, ankyrin G, Mucin 1; TM cell markers AQP1, MGP, CHI3L1, TIMP3 and glaucomatous marker myocilin. FIG. 3A-E on the upper column show the TMSC were positive to stem cell marker proteins ABCG2, Pax6 FIG. 3A, ankyrin G FIG. 3B, mucin 1 FIG. 3C; but not TM cell markers CHI3L1 FIG. 3B, AQP1 FIG. 3C, MGP FIG. 3D, TIMP3 FIG. 3E and not glaucomatous marker myocilin (D). In contrast, the primary TM cells of the lower column FIG. 3F-3J did not express stem cell markers, but instead expressed TM cell markers. Few cells were positive to myocilin. Results obtained from qPCR (FIG. 3K) demonstrated the differential gene expression pattern between the primary TM cells and the TMSC. TMSC demonstrated increased expression of stem cell genes ABCG2 and ankyrin G, decreased TM cell genes AQP1, MGP, CHI3LI, and decreased glaucomatous genes myocilin and ELAM I, as compared to primary TM cells. The differences were statistically significant as determined by the one-tailed t-test. qPCR and Western Blotting (WB) confirmed similar expression levels. The expression of mucin I differed by very little among primary TM cells and TMSC. FIG. 3L shows the results of Western blotting that compare the different protein expression between corneal stromal fibroblasts and passage-4 TMSC. As evident in this figure, TMSC strongly expressed the stem cell markers ABCG2, Pax6, Mud and weakly expressed the TM cell markers AQP1, MGP and TIMP3.

TMSC can be Induced to Differentiate into Trabecular Meshwork Cells.

The TMSC were cultured in SCGM, and at passage-4, the TMSC were switched into different media for induction of differentiation into TM cells. The cells were induced in medium containing 50% SCGM with 50% aqueous humor, 100% aqueous humor, or with medium containing 10% FBS. The expression levels of stem cell markers arid TM cell markers were analyzed among the induced cells and the TMSC in SCGM by immunofluorescent staining and qPCR.

The first column of FIG. 4A, 4E, 4I, 4M, 4Q represents the stain of TMSC in SCGM; the second column (B, F<J, N, R) represents the stain of induced cells in SCGM/AH; the third column FIG. 4C, 4G, 4K, 4O, 4S represents the stain of cells in aqueous humor; the forth column FIG. 4D, 4H, 4L, 4P, 4T represents the stain of cells in medium containing 10% FBS. The top row of FIG. 4A, 4B, 4C, 4D (A, B, C, D) represents a double-stain of ABCG2 (green) and Pax6 (red); the second row represents a double-stain of ankyrin G (green) and CHI3L1 (red); the third row represents a double-stain of mucin 1 (green) and AQP1 (red); the fourth row represents a double-stain of MGP (green) and myocilin (red); the bottom row represents a stain of TIMP3 (green).

Figure 4U:
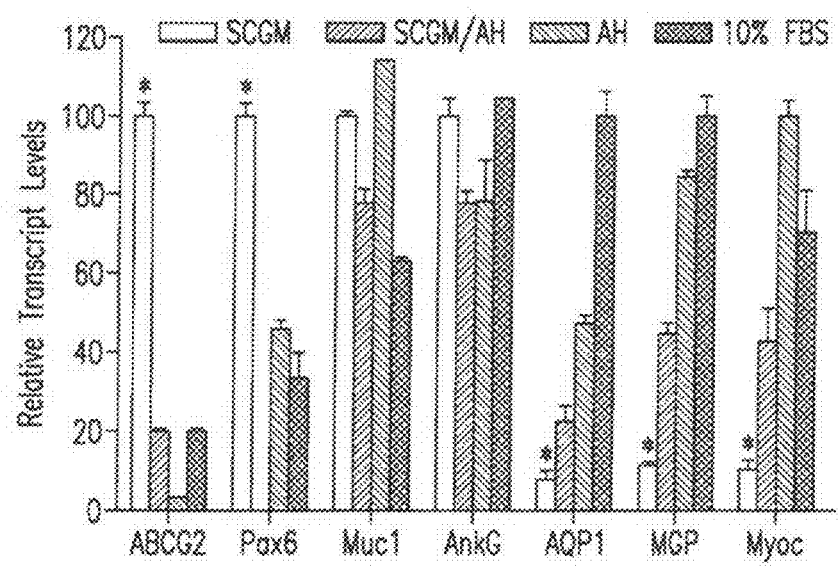
FIG. 4U: mRNA pools for stem cell makers ABCG2, Pax6, Muc1, AnkG; TM markers AQP1, MGP; and glaucoma markers myocilin were quantified by qPCR to compare the differences between the passaged TMSC and the induced TM cells in different media. Error bars show SD of triplicate analyses. Asterisks indicate significant (p<0.05) difference between the TMSC and the induced TM cells in all three different media. Abbreviations: SCGM, stem cell growth medium; 5CGM/AH, 50% stem cell growth medium+50% aqueous humor; AH, aqueous humor; FBS, fetal bovine serum.
Figure 4V:
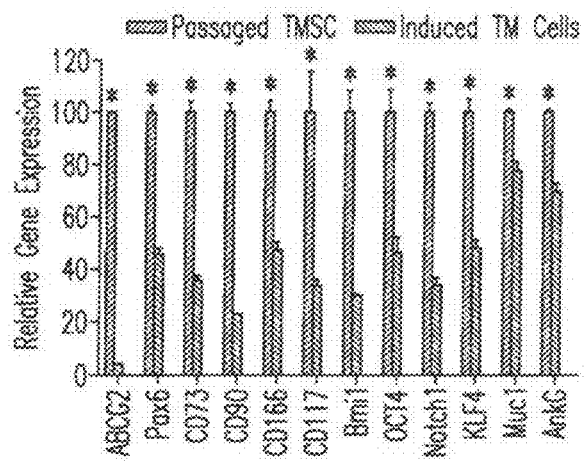

These data support that TMSC can be induced to differentiate into TM cells expressing TM markers and exhibiting lost or reduced expression of stem cell markers ABCG2, Pax6, AnkyrinG and mucin1. The TMSC cultured in SCGM remained the stem cell markers ABCG2 (FIG. 4A—green)), Pax6 (FIG. 4A—red)), Ankyrin G(FIG. 4E—green), Mucin1 (FIG. 4I—green), but not the TM differentiation markers CHI3L1 (FIG. 4E—red), AQP1 (FIG. 4I—red), MGP (FIG. 4M—green), TIMP3 (FIG. 4Q—green) and not the glaucomatous marker myocilin (FIG. 4M—red). When the stem cells were induced in SCGMIAH for one week (FIG. 4B, 4F, 4J, 4N, 4R), some of the cells lost the stem cell markers but gained the express of the TM markers. When the cells were induced in AH (FIG. 4C, 4G, 4K, 4O, 4S) or in 10% FBS (FIG. 4D, 4H, 4L, 4P, 4T), most of the cells lost the ability to express the stem cell markers but expressed the TM cell markers. Some of the induced cells were positive to the glaucomatous specific marker myocilin (FIG. 4N, 4O, P-red).

qPCR demonstrated that the transcript level of stem cell genes ABCG2 and Pax6 of the TMSC in SCGM increased at least 2-fold compared to that of the induced cells in SCGM/AH, in AH or in 10% FBS (FIG. 4U), qPCR also demonstrated that the relative gene expression of stem cell markers ABCG2, Pax6, CD73, CD90, CD166, CD117, Bmi1, Oct4, Notch 1, and KLF4 in induced TM cells was 50% or less that in passaged TM cells (FIG. 4V).

Figure 4W:
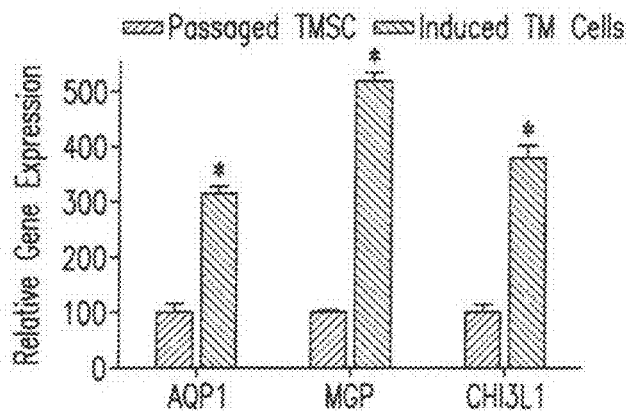

The transcript level of TM genes AQP1, MGP, and CHI3L1 of the induced TM cells were increased at least 2-fold as compared to that passaged TMSCs (FIG. 4W). The expression of glaucomatous gene myocilin in the TMSC in SCGM was also decreased compared to that of the induced cells. The difference between the TMSC and the induced TM cells was statistically significant by t-test (p<0.05). There was no significant difference in the expression of mucin 1 and ankyrin G between the TMSC and the induced cells. The differences among the induced cells also were not significant.

Figure 4X:
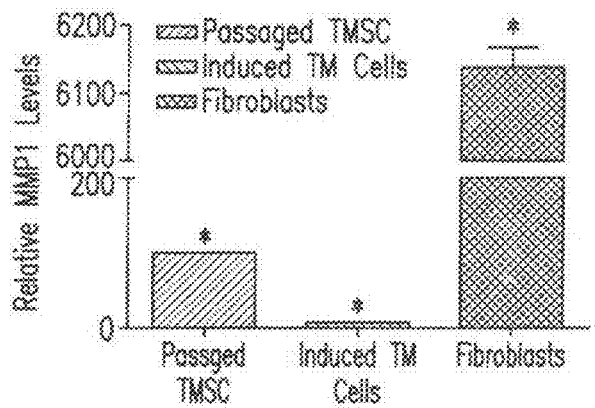

The expression of MMPI (interstitial collagenase) was analyzed via qPCR among passaged TMSCs, induced TM cells and fibroblasts. As shown in FIG. 4X, the expression of MMPI greatly varied among these three cell populations.

Phagocytosis by the Induced TM Cells

Trabecular meshwork cells have phagocytic activity which eliminates debris, pigment and other materials from the aqueous outflow drainage pathway and maintains the aqueous humor outflow pathway (14, 37, 38). A phagocytosis assay was performed with TMSC cultured in SCGM (FIG. 5A), with induced cells cultured in SCGM/AH (FIG. 5B), in AH (FIG. 5C), or in 10% FBS (FIG. 5D) and with primary TM cells (FIG. 5E) cultured in medium without fetal bovine serum and growth factors.

Rabbit IgG-opsonized Alexa 488 conjugated *Staphylococcus aureus* bioparticles were incubated with the cells at 37° C. for 1 h. After incubation, the cells were fixed in 4% PFA and then incubated with Alex 546 goat anti-rabbit IgG to bind any unphagocytosed extracullular bioparticles. The ingested bioparticles by the cells were green and the non-ingested bioparticles conjugated with the red second antibody showing yellow in FIG. 5A-5E. Only a few green particles were ingested by the TMSC in SCGM (FIG. 5A). In contrast, the induced cells (FIG. 5B-5D) and the primary TM cells (FIG. 5E) ingested many green bioparticles. The green particles, the non-ingested yellow bioparticles, and the number of the nuclei (blue) in each view were counted and at least ten different views were counted in each condition. The number of ingested bioparticles per cell was calculated as the number of ingested green ones, minus the number of non-ingested yellow ones, divided by the number of blue nuclei. FIG. 5F provides the statistical result of the phagocytic assay. The Y-axis shows the number of the bioparticles ingested per cell. The difference between the TMSC cultured in SCGM and the induced cells as well as the primary TM cells is statistically significant (p<0.0001) analyzed by ANOVA followed by Bartlett's test with Prism Graph Pad software (Prism; Graph Pad Software, San Diego, www.graphpad.com). There is no significant difference among the induced cells and the primary TM cells.

These data demonstrate that the induced cells function similarly to TM cells.

Multipotency of TMSC.

One well-documented aspect of adult stem cells is the ability to differentiate into a number of different cell types. This property was examined in the cloned TM stem cells by culturing them in different conditions. The TMSC was cultured in neural differentiation medium (NDM) containing EGF, FGF and retinoic acid for neural induction. By immunofluorescent staining, the cells positive for neurofilament (FIG. 6A), beta-tubulin III (FIG. 6B) and GFAP (FIG. 6C) were present among cells cultured in NDM. At the mean time, the cells cultured in NDM lost the expression of mucin 1. In contrast, the TMSC cultured in SCGM without induction were positive to mucin 1 (FIG. 6H) but negative to neurofilament (FIG. 6E), beta-tubulin III (FIG. 6F) and GFAP (FIG. 6G).

The TMSC was cultured in adipogenic differentiation medium (ADM) and adipogenc maintenance medium (AMM) for adipocytic induction. Oil red 0 stain was perform to identify lipoid deposits which are special to adipocytes. FIG. 6J shows the TM stem cells in SCGM had no lipoid materials with oil red O negative. After induction in ADM and maintaining in AMM, the TM stem cells changed to be positive to oil red O stain with lipoid deposits within the cells.

Real-time qPCR was carried out to compare the expression of adipocytic genes ap2 (which encodes ALBP) and leptin among stem cells maintained in SCGM or induced adipocytes in ADM. The expression of ap2 and leptin were increased in adipocytes, as compared to the expression of these genes in the stem cells. The increase was statistically significant as determined by t-test.

Our previous experiments showed that the corneal stromal stem cells were able to differentiate into keratocytes by culturing the stem cells as pellets in a medium containing FGF and ascorbic-2-phosphate39. We adopted this method to induce the keratocyte differentiation from TMSC. After culturing over 3 weeks as pellets, the TM stem cells secreted corneal stromal specific extracellular matrices keratan sulfate (FIG. 6K) and keratocan (FIG. 6L).

Figure 7B:
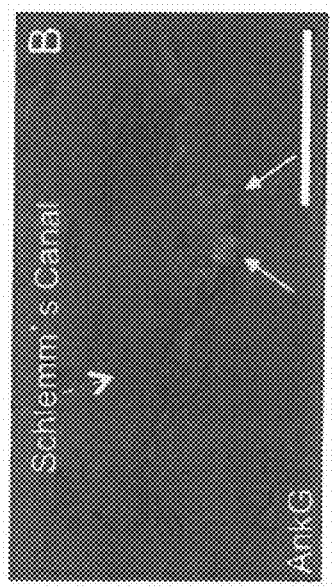
FIG. 7A-7Q demonstrates an exemplary injection of human TMSCs into mouse anterior chamber (AC). Human TMSC were injected into normal mouse AC for 1 week, 2 weeks and 4 weeks. At 2 weeks, the cryosections of the eyeballs were stained with TM marker AQPI FIG. 7A and TMSC marker AnkG FIG. 7B, Schlemm's canal is labeled by the dashed arrows; the white solid arrows point to the injected green ceils in the TM region; yellow arrows point out that the sclera is on the left and the cornea is on the right of the TM. TM tissue whole mount stain was performed an TMSC injection at 1 week FIG. 7D, 7I, 7N and 4 weeks FIG.
FIG. 7C-7G are stains with anti-AQP1 antibody which reacts with both human and mouse antigen; H-L are stains with anti-human specific CHI3L1 antibody; M-Q are stains for Muc1 antibody which is not specific as AQP1.
FIG. 7M shows the sclera is over the left; cornea is over the right while the TM is in the middle which applies to all the whole mount stain in FIG. 7A-7Q. The injected human TMSC or fibroblasts were prelabeled with Di0 as green. DAPI stains for nuclei as blue. Bars=50 um. Abbreviations: hTMSC, human trabecular meshwork stem cells; AC. Anterior chamber; TMSC-1w, 1 week after trabecular meshwork stem cell injection; Fibro-1w, 1 week after fibroblast injection.
Figure 7A:
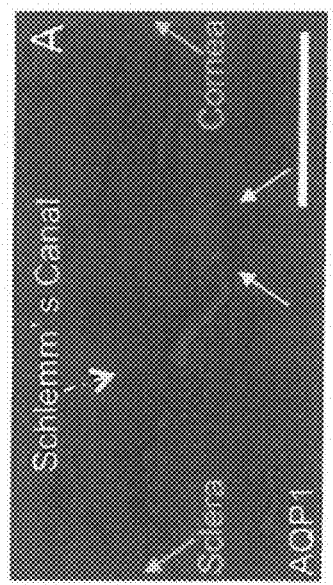

Deposition into trabecular meshwork of TMSC after anterior chamber injection. To detect whether the Passage-4 human TMSC can localize into the TM tissue after introducing into anterior chamber, we prelabeled the TMSC as green and injected 2 µl of 5×104 TMSC into normal mouse anterior chamber. FIGS. 7A and 7B show the immunofluorescent staining on the mouse TM cryosections 2 weeks after hTMSC injection. The injected green cells homed to the TM tissue pointed by white solid arrows (FIG. 7A, 7B). Some of the green cells were positive to the TM differentiation marker AQP1 (FIG. 7A-red) and some were positive to the stem cell marker ankyrin G (FIG. 7B-red).

FIG. 7C-7Q are the wholemount staining on mouse TM tissue with TMSC injection for 1 week (FIG. 7D, 71, 7N), 4 weeks (FIG. 7F, 7K, 7P); with fibroblast injection for 1 week (FIG. 7E, 73, 7O), 4 weeks (FIG. 7C, 7L, 7Q); and normal tissue without any injection as controls (FIG. 7C, 7H, 7M). TM cell antibody AQPI reacts to both mouse and human antigens; TM cell antibody CHZ3L1 is specific to human antigen; stem cell antibody mucin 1 reacts to both mouse and human antigens. Mucin 1 has been identified for the expression on corneal endothelium 40. FIG. 7C, 7H, 7M on the control tissue show that AQPI presented in the mouse TM cells as well as in the corneal endothelial cells (FIG. 7C) but human specific CHI3L1 antibody didn't stain any mouse cells (FIG. 7H); there were some cells positive to mucin 1 in both the TM and the endothelium (FIG. 7M).

FIG. 7D, 7I, 7N are stains on the tissue with TMSC injection for 1 week. 1 week after injection, there were some injected green human TMSC positive to AQP1 (FIG. 7D), some positive to human specific antibody CHI3L1 (FIG. 7I); the number of cells positive to stem cell marker mucin 1 increased (FIG. 7N) compared to the control without cell injection (FIG. 7M). There were very few injected green green cells in the TM region 1 week after injection with human fibroblasts (FIG. 7E, 7J, 7O) and no increase of AQPI expression (FIG. 7E), no human CHI3L1 expression (FIG. 7J), no increased mucin 1 expression (FIG. 7O).

4 weeks after cell injection, the number of injected green cells in the TM region was significant increased compared to that at 1 week after injection. Although more green cells were in the TM region, more injected TMSC were positive to mucin 1 (FIG. 7P) and less cells were positive to the differentiation markers CH13L1 (FIG. 7K) and AQP1 (FIG. 7F). Interestingly, although there were almost no injected fibroblasts in the TM region 1 week after injection, 4 weeks after fibroblast injection, there were more green cells in the TM region that that at 1 week (FIG. 7G, L, Q). There was no expression of human specific CHI3L1 among the injected green fibroblasts (FIG. 7L), although the green cells were in the TM region where AQP1 (FIG. 7E) and mucin I (FIG. 7O) were positive to the original mouse cells.

TABLE A

| Protein Name | Alternative Names | Reference |
|---|---|---|
| 14-3-3 | | Zhao X et al, 2004 |
| 14-3-3-zeta | YWHAZ, Tyrosine 3-MonooxygenaseTiryptophan 5-Monooxygenase Activation Protein-zeta, 34-3-3-delta, Exo1, FAS, factor activating ExoS | Vittal et al, 2005 |
| A20 | TNFAIP3 [TNF-alpha-induced protein 3, tumor necrosis factor-alpha-induced protein 3 | Michael et al, 2008 |
| AAC-11 | anti-apoptosis clone 11, API5, Apoptosis inhibitor 5, FiF, Fibroblast growth factor-2 interacting factor, FGF-2 interacting factor, API5L1, APIS-like-1 | Rozsa et ai, 2006 |
| AATF | apoptosis antagonizing transcription factor; Che-1 | Rozsa et al, 2006 |
| Activin A | EDF, erythroid differentiation factor, FRP, Follicle stimulating hormone releasing protein, Restrictin-P, WEHI-MIF, WEHI mesoderm inducing factor, INHA, inhibin-aipha, Inhib'sn-beta-A, INHB A | Zhao X et al, 2004; Rozsa et al, 2006 |
| ADAM 10 | disintegrin and metalloprotease domain 10, MADM, mammalian disintagrin meta7loprotease, CDw1.56c, CDI56c, kuxhanian, EC3.4.24.81 | Rozsa et al, 2006 |
| ADAM12 | (disintegrin and metalloprotease domain 12, Meltrin-alpha, MLTNA) | (Zhao X et al, 2004) |
| ADAM19 | MADDAM, rnetalloprotaase and disintegriri dendritic antigen marker, Meltrin-beta, ML'1'NB | Rozsa et al, 2006 |
| ADAM28 | disintegrin and metalloprotease domain 28 MDC-L, metalloproteinase-like disintegrin-like cysteine-rich protein L, MDC-3, metalloproteinase-like disintegrin-like cysteine-rich protein-3, ADAM23, disintegrin and metalloprotease domain 23 | Rozsa et al, 2006 |
| ADAMTSI | Disintegrin and metalloproteinase with thrombospondin motif-1, METH-1 | Luna et al, 2009; Rozsa et al, 2006; Keller et al, 2009 |
| ADAMTS3 | Disintegrin and metalloproteinase with thrombospondin motif-3, KIAA0366, Procollagen II amino propeptide-pi-ocessing enzyme, PC II-NP, Procollagen 1I N-proteinase | Rozsa ct al, 2006 |
| ADAMTS4 | Disintegrin and metalloproteinase with thrombospondin motif-4, Aggrecanase-1, hyalectanase | Keller et al, 2009 |
| ADAMTS5 | Disintegrin and metalloproteinase with thrombospondin motif-5, aggrccanase-2, implantin | Luna et al, 2009; Rozsa et al, 2006; Keller et al, 2009 |
| ADF | Adult T-cel 1 leukemia-derived factor; ATL-derived factor; 3B6-IL1 3136-ILI-like factor, 5ASP, surface-associated sullhydryl protein, TCGF[IL2]-receptor inducing factor, IL2-RIF, IL2 receptor inducing factor, TIA, IL2R/p55 inducin factor | Zhao X et ci, 200 |
| adipophilin | | Zhao X et ci, 2004 |
| Adrenomedullin | ADM, AM | Rozsa et al, 2006; Zhao X et al, 2004 |
| aFGF | acidic fibroblast growth factor, FGF-1, Fibroblast growth factor-1, FGF-alpha, Fibroblast growth factor-alpha, HBGF-1, heparin binding growth factor-1, Endothelial cell growth factor-alpha | Luna et al, 2009 |

TABLE A-continued

| | | |
|---|---|---|
| aFGF | acidic fibroblast growth factor, FGF-i, Fibroblast growth factor-1, FGF-alpha, Fibroblast growth factor-alpha, HBGF-1, heparin binding growth factor-1, Endothelial cell growth factor-alpha receptors | Alexander et al, 1998; Wordinger et at, 1998 |
| Agn.n | AGRN | Rozsa et al, 2006 |
| ALK3 | Activin receptor-like kinase 3, BMPRIA, bone morphogenetic protein receptor type IA, CD292 | Luna et al, 2009 |

| Protein Name | Alternative Names | Reference |
|---|---|---|
| alpha-l-antichyrnatrypsin | | Fukuchi et al, 1997 |
| alpha-l-macroglobulin receptors | | Howard et al, 1996 |
| alpha-l-proteinase inhibitor | | Fukuchi et al, 1997; Sawaguchi et ai, 1994 |
| Alpha-2-Macrog;obulin | Alpha-2MG, Alpha-2M, A2M | Fukuchi et al, 1997; Howard et al, 1996 |
| Alpha-B-crystallin | crystallin-alpha B or crystallin-alpha 2, alphaBC, CRYAB, CRYA2, REN-27, NY-REN-27, hspB5, heat shock protein beta-5 | Schlunck et al. 2008; Mitton et al, 1997; Zhao X et al, 2003; Zhao X et al, 2004; Vittal et al, 2005 |
| ANF | Atrial natriuretic factor, natriuretic peptide, atrionatriuretic factor, Alpha-ANP, Atrial natriuretic polypeptide, ANP, Atrial polypeptide, Atriopeptin, cardionatrin, cardionatrin I, NPPA receptors | Chang et al, 1996; Zhong L et al, 2003 |
| angiomotin-like-2 | AmotL-2, MASCOT, LCCP, Leman coiled-coil protein | Rozsa et al, 2006 |
| angiopoietin-1 | Ang-1, ANGPTI | Fan et al, 2008 |
| angiopoietiJl-2 | Ang-2, ANOPT2 | Borras et al 2006 |
| Angiopoietin-like-2 | ANGPTL2, ARP-2, angiopoietin-related protein-2 | Rozsa et al, 2006 |
| angiopoietin-like-4 | ANGP'I'L4, ARP-4, angiopoietin-related protein-4, FIAF, fasting induced adipose factor, HFARP, hepatic fibrinogen/angiopoletin-related protein, PGAR, peroxisome proliferator-activated receptor-gamma-related protein ANGPTL7, CDT6, cornea-derived transcript 6, Angiopoietin X, AngX | Luna et al, 2009; Vittal et al, 2005; Rozsa et al. 2006 |
| angiopoietin-like-7 | | Luna et al, 2009; Rozsa et al, 2006 |
| angiotensin-2 | | Savaskan et al, 2004 |
| angiotensin-2 receptors | | Shen F et al, 2001 |
| Annexin-1 | Annexin A1, ANX1, ANXA 1, lipocortin-1, LPC1, LCTI, LC1, Lipo1, macrocortin, renocortin, lipomodulin, GIF, glycosylation inhibiting factor, CB9, chromobindin-Π, calpactin-2 | Zhao X et al, 2004 |
| Annexin-2 | Annexin A2, ANX2, ANXA2, PAP-4, placental anticoagulant protein 4, Lipocortin-2, Endonaxin-2, Calpactin-1 | Zhao X et a1, 2004; Rozsa et al, 2006 |
| Annexin-5 | Annexin AS, ANXS, ANXA5, 35 kDa Calelectrin, 35-gamma Calcimedin, Anchoein C2, PAP-i, placental anticoagulant protein-I, CBP-J, Calphobindin-1, CBP, calphobindin, Endonexin-2, ENX2, Lipocortin V, Lipocortin-5, VAC-alpha, vascular anticoagulant-alpha, chromobindin-4, 32 kba calcimedin, EEP 32-2, PP4, placental protein-4, Ca$P33, calcium binding protein 33 kDa, CaB P3?, calcium binding protein 37 kDa | Rozsa et al, 2006 |
| antithrombin III | | Fukuchi et al, 1997 |
| BAG-1 | BCL2-associated athanogene-1, RAP46, receptor-associating protein 46 kDa, BCL2L6, BCL2-like-6 | Rozsa et al, 2006 |
| BAG-3 | BCL2-associated athanogene-3, CAIR-1, CAI stressed-1, B1S | Rozsa et al, 2006; Luna et al, 2009 |
| BAK | BAK-1, BCL2 antagonist/1ci. 11er, BCL2 homologous antagonist 1ciller, BCL2-like-7, BCL2L7 | Ishibashi et al, 2002 |
| BAX | BCL2 associated x protein, BCL2L4, BCL2-like-4 | Agarwal et al, 1999 |
| BCL2 | B-cell lymphomalleukemia-2 | Agarwal et al, 1999 |
| BCL2L13 | BCL2-like-13, MILL BCLrambo | (Rozsa et al, 2006) |
| BCL3 | B-cell lymphoma/leukemia-3 | Zhao X et al, 2004 |
| BCLxL | BCL2-like-1, BCL2L1 | Agarwal et al, 1999 |
| BDNF | Brain-derived neurotrophic factor | Wordinger et al, 2000 |

| Protein Name | Alternative Names | Reference |
|---|---|---|
| Beta-2-Microglobulin | Beta-2-M, B2M, Ly-m1 1, B13GF-2, bone-derived growth factor-2, CRG-8, cytokine responsive geΠe-8, Thymotaxin, G1P-2, granulocyte inhibitory protein | Rozsa et al, 2006 |
| betaglycan | TGFBR3, TOFR3, TGF-beta receptor type 3, Tumor necrosis factor superfamily, member 10 | Luna et al 2009 |

TABLE A-continued

| | | |
|---|---|---|
| Receptor for bFGF | Receptor for basic fibroblast growth factor, FGF-2, Fibroblast growth tactor-2, FGF-beta, Fibroblast growth factor-beta, HBOF-2, heparin binding growth factor-2 | Alexander et al, 1998; Ando et al, 2004; Polansky et al, 2000; Tripathi et al, 1997; Wordinger et al, 1998 |
| Biglycan | | Vittal et al, 2005 |
| BMP2 | (bone morphogenetic protein-2, bone morphogenetic protein-2A, BMP2A, BMP2-alpha) | (Luna et al, 2009; Rozsa et al, 2006) |
| BMP2 receptor | Receptor for bone morphogenetic protein-2, bone morphogenetic protein-2A, BMP2A, BMP2-alpha | (Xue W et al, 2006) |
| BMP6 | (DVR-6, decapentaplegic-Vg-related-6, Vgr-1, vegetal-specific-related-1) | (Luna et al, 2009) |
| BMP7 | (bone morphogenetic protein-7, QP-1, osteogenic protein-1, Eptotermin alfa, Osigraft) | (Fuchshofer et al, 2007) |
| BMP7 receptor | Receptor for bone morphogenetic protein-7, OP-I, osteogenic protein-1, Eptotermin alfa, Osigraft | (Fuchshofer et al, 2007; Fuchshofer et al, 2009) |
| BMPER | BMP binding endothelial regulator, Bone morphogeuetic protein-binding endothelial cell precursor-derived regulator, CRIM3, cysteine-rich BIvIP regulator-3, Crossveinless-2, Cv-2 | (Rozsa et al, 2006) |
| BMPR1A | bone morphogenic protein receptor type IA | (Rozsa et al, 2006) |
| B1l'IP2 | NIP-2, BCL2/adenovirus EIB 19 kDa protein interacting protein-$^2$ | (Ishibashi et al, 2002) |
| BNIP 3 | BCL2ladenovirus BIB 19 kDa protein nteracting protein-3, NIP-3 | (Rozsa et al, 2006) |
| BNIP3L | BCL2ladenovirus E 18 19 kDa protein interacting ptotein-3-like, $NIP3A, BCL2/adenovirus BIB 19 kDa protein interacting protein-3A, BNIP3-alpha, NIX, Nip3-like protein X | (Rozsa et al, 2006) |
| BNP receptor | Receptor for Brain natriuretic peptide, B-type natriuretic peptide, NPPB, ASIP, Aldosterone Secretion Inhibitory Factor, BNP(1-32), BNP-32, Brain natriuretic peptide-36, N-terminal proBNP, NT-proBNP, gamma-BNP | (Chang et al, 1996; Zhong L et al, 2003) |
| bradykinin receptor | Receptor for BK, BDK, BKN, Bradykinin(1-9), BK [1-9], Alpha-2-thiol proteinase inhibitor, Fitzgerald factor, Flaujeac factor, HMWK, HMWKa, High molecular weight kininogen, HMWK-kallikrein factor, KNG, KNG1, Kininogen, Kininogen-1, LMWK, Low molecular weight kininogen, Williams factor, Williams-Fitzgerald-Flaujeac factor | (Luna et al 2009; Webb et al, 2009; Abad et al, 2008; Webb et al, 2003, 2006; Llobet et al, 1999; Sharif and Xu, 1996) |
| BTCs1 | (B-cell translocation gene-1, BTG family member 1) | (Rozsa et al, 2006) |
| BTG3 | (B-cell translocation gene-3, BTG family member 3, ANA, Abundant in Neuroepithelium Area) | (Rozsa et al, 2006) |
| CI inhibitor | (C1IN1-1, Serpin 01) | (Razsa et al, 2006) |
| Cadherin-4 | | Leung YF et al, 2003 |
| Cadherin-11 | | Luna et al, 2009 |
| Caspase-4 | (CASP4, ICBrel-2, 1L1-beta Convertase-related-2, TX, transcript X, ICH-2, ICE and CED3 homolog-2) | (Fan et al, 2008) |
| caspa8e-6 | CASP6, MCH2, mammalian CED3 hamolog-2) | (Rpzsa et al, 2006) |
| caveolin-1 | (CAV1, caveolae protein 1, Caveolin, CAV, caveolae protein 22 kDa, Alpha-Caveolin, beta-Caveolin, VIP21, Vesicular Integral-membrane Protein of 21 kDa, VIP21/caveolin) | (Rozsa et al, 2006) |

| Protein Name | Alternative Names | Reference |
|---|---|---|
| CCL2 | (CC chemokine ligand 2, chemokine (C-C motif) ligand 2, GDCF, Glioma-derived monocyte chemotactic factor-2, GDCF-2, I1CI 1, JE, LDCF, MCAF, MC?, monocyte chemoattractant protein, MCP-1, monocyte chemoattractant protein-1, SMC-CF, smooth muscle cell chemotactic factor, TDCF, tumor-derived chemotactic factors, T5G-8, tumor necrosis factor-stimulated gene sequence-8, SCYA2) | (Fan et al, 2008; Zhao X et al, 2004; Vittal et al, 2005) |
| CCL7 | CC chemokine ligand 7, chemokine (C-C motif) ligand 7, SCYA7, MCP-3 , monocyte chemoattractant proteiII-3, FIC, Fibroblast-inducible cytokine, NC28, MARC, mast cell activation-related chemokine | Luna et al, 2009; Vittal et al, 2005 |
| CCL11 | CC chemakine ligand 11, chemokine (C-C motif) ligand 11, 3CYA11, Eotaxin, Botaxin-1 | Vittal et al, 2005 |
| CCL13 | CC chemokine ligand 13, chemokine (C-C motif) ligand 13, MCP-4, Monocyte chemotactic protein-4, NCCI, new CC chemolcine-1, Ck-beta-10, Chemokine-beta-10, SCYLI, SCYA13 | Vittal et al, 2005 |
| CCR2 | CC-Chemokine receptor 2, CC-CKR2A, CCR2A, CC-CKR2B, CCR2B, MCP-1 receptor A, MCR1 receptor B, CMKBR2, chemokaine-beta receptor 2, CD192 | Rozsa et al, 2006 |
| CD9 | 602-29 antigen, ALB6 antigen, BA2, BTCC-1, DRAF-27, Diphtheria toxin receptor associated protein 27 kDa, G1G2, MIC3, MRP-1, Motility-relatedprotein-1, NCA, neural cell surface antigen, p24, 5H-9, TSPAN29, tetraspanin 29 | (Rozsa et al, 2006) |

TABLE A-continued

| | | |
|---|---|---|
| CD13 | (alanyl aminopeptidase, nAP, ANPEP, alpha-aminoacyi-peptide hydrolase (microsomal), aminopeptidase N, PEPN, APN, Ai'M, aminopeptidase M, EC3.4.11.2, LAP1, microsomal aminopeptidase, MY 7, MCS-2, p156) | (Coupland et al, 1993) |
| CD24 | CD24a, 30F1, B2A2, BA-I, HIS50, f35A, heat stabte antigen, 31 ld, JHd, Ly52, M1/69, Nectadrin, LR-1, SCLC surface antigen Cluster-4, CI, -4 | Zhao X et al, 2004 |
| CD26 | 1F7, 2B9, SF8, ACT-3, ADABP, ADA binding protein, ADCP2, adenosine deaininase complexing protein 2, BT5/9, DPCRI, BPP4, dipeptidyl peptidase 4, HAM.4, intestinal dipeptidyl peptidase, EC3.4.14.5, OX61, TA1, TA5/9, THAM, thymocyte-activating molecule, TP103, WC10 antigen, FAP-beta, Fibrobiast activation protein-beta | Rozsa et al, 2006; Coupland et al, 1993 |
| CD29 | FNRB, fibronectin receptor beta subunit, ITGB 1, integrin-beta-1, platelet protein GPIIa, VLA-beta, very late activation antigen-beta, VLA-beta-1, VLA-4 beta subunit | FiHa etal, 2006; Peterson et al, 2005; Zhou L et al, 1999; Zhou L et al, 1996 |
| CD44 | CD44H, AnWj blood group antigen, ECMR-3, extracellular matrix receptor-3, HCAM, homing-associated cell adhesion molecule, FIermes-1, Hermes antigen, HUTCH-1, Indian blood group antigen, In blood group antigen, Ly24, MC56, MDU2, MDU3, M1C4, MUC 2-63, 0X49, PGP1, PGP 1.1, phagocytic glycoprotein-1 | Keller et al, 2007; Jumper et al, 1998; Li Z and Zhang H, 2004; Vittal et al, 2005 |
| CD46 | gp45-76, Hul.y-m5, MCP, membrane cofactor protein, measles virus receptor, MICIO, TLX, TRA-2-10, trophoblast-leukocyte common antigen, trophoblast-lymphocyte cross-reactive antigen | Rozsa et al, 2006 |
| CD49a | ITGAI, integrin-alpha-1, VLA-1, very late activation antigen I | (Zhou L et al, 1996; Zhou L et al, 1999) |
| CD49b | Br alloantigen, DX5, ECMR-2, extracellular matrix receptor-2, GPIa, HPA-5, human platelet antigen-5, ITGA2, integrin-alpha-2, platelet glycoprotein Ia/IIa, VLA-2, very late activation antigen 2, VLAA2, VLA2 receptor alpha 2 subunit, Zav alloantigen | (Luna et al, 2009; Dickerson et al, 1998; Filla eta 1, 2006; Zhou L et al, 1996) |

| Protein Name | Alternative Names | Reference |
|---|---|---|
| CD49c | CSAT antigen band 2 protein, FRP-2, fusion regulatory protein-2, GAP-B3, galactoprotein B3, ITGA3, integrin-alpha-3, MSK18, VLA-3, very late activation antigen 3, VLAA3, VLA-3 receptor alpha 3 subunit | (Dickerson et al, 1998; Zhou Let al, 1999; Zhou L et at, 1996) |
| CD49d | (TTGA4, integrin-alpha-4, VLA-4, very late activation antigen 4, VLAA4, VLA4 receptor alpha 4 subunit) (Dickerson et al, 1998; Peterson et al, 2005; Zhou L et al, 1999; Zhou L et at. 1996) | |
| CD49e | (fibronectin receptor alpha chain, FNRA, ITGA5, integrin-alpha-5, VLA-5, very late activation antigen 5, VLA-5-alpha) | (Luna et at, 2009; Dickerson et al, 1998; Peterson et al, 2005; Zhou L et at, 1999; Zhou I, et al, 1996) |
| CD49f | (ITGA6, integrin-alpha-6, platelet gppl, VLA-6, very late activation antigen 6, VLA-6 alpha chain) | (Luna et al, 2009; Zhou L et al, 1999; Zhou L et at, 1996) |
| CD29 | (FNRB, fibronectin receptor beta subunit, ITGB 1, integrin-beta-1, platelet protein GPIIa, VLA-beta, very late activation antigen-beta, VLA-beta-1, VLA-4 beta subunit) | (Junglas et al, 2009) |
| CD44 | (CD44H, AnWj blood group antigen, ECMR-3, extracellular matrix receptor-3, HCAM, h?ming-associated cell adhesion molecule, Hermes-1, Hermes antigen, HUTCH-1, Indian blood group antigen, In blood group antigen, Ly24, MC56, MDU2, MDU3, MIC4, MUC 2-63, OX49, PGP1, PGPi.1, phagocytic glycoprotein-1) | (Fan et al, 2008; Miller et al, 2007; Lin et at, 2007) |
| CD51 | (ITGAV, integrin-alpha-V, L230, MSK8 vitronectin receptor VNRA, vitronectin receptor alpha subunit) | (Junglas et al, 2009; Dickerson et al, 1998; Zbou L at al, 1999; Zhou Let al, 1996) |
| CD54 | (7F7, BB2, human rhiuovirus receptor, ICAM-1, intercellular adhesion molecule 1, IFN-gan$^{II}$aa regulated human melanoma-associated antigen, Ly47, MALA-2, Me14-D12, P358) | (Rozsa et al, 2006) |
| CD55 | (CD55a, CD55b, complement decay-accelerating factor, decay-accelerating factor, DAF, DAF-GPI, DAF-TM, GPI-DAF, TM-DAF, DAF1, decay-accelerating factor 1, DAF2, decay-accelerating factor 2, Cromer blood group antigen) | (Rozsa et al, 2006; Michael et al, 2008) |
| CD61 | (CD61A, F4, F11, GPIIbIIIa, HPA-1, human platelet antigen-1, HPA-4, human platelet antigen-4, ITGB3, integrin-beta-3, Pen alloantigen, Pen(a), Pen(b), PL(A1), platelet fibrinogen receptor beta subunit, platelet glycoprotein IIIa, GP3A, Yuk alloantigen, Yuk(a), Yuk(b), Zw alloantigen, Zw(a), Zw(h)) | (Filla etal, 2006; Zhou L et at, 1999; Zhou L at al, 1996; Rozsa et al, 2006) |

TABLE A-continued

| | | |
|---|---|---|
| CD62E | (ELAM, ELAM-1, endothelium leukocyte adhesion molecule 1, ESEL, E-selectin, selectin-E, S.ELE, GMP-140, GRMP, granulocyte membrane protein, 1.ECAM-2, leukocyte adhesion molecule 2, platelet alpha-granule membrane protein) | (Luna et al, 2009; Li et at, 2007; Zhou Q et aI, 2007) |
| CD63 | (81H, ADI, GP55, granulophysin, LIMP, lysosomal integral membrane protein, LIMP-1, lysosomal integral membrane protein-1, ME491, melanoma associated antigen ME491, MLAI, melanoma-associated antigen 1, NGA, neuroglandular antigen, NKi-C3, OMA81 H, ocular melanoma-associated antigen 81H, PLTGP40, platelet glycoprotein gg40, TSPAN30, tetraspanin 30) | (Rozsa et al, 2006) |
| CD87 | (MO3, PLAUR, plasminogen activator urokinase receptor, UPA-R, urokinase plasminogen activator receptor, URKR, urokinase receptor) | (Rozsa et al, 2006) |

| Protein Name | Alternative Names | Reference |
|---|---|---|
| CD95 | FAS, APO-1 apoptosis antigen-1, APT1, TNFRSF6, TNF receptor superfamily member 6, FASTM, FASL receptor | Agarwal et al, 1999; Rozsa et al, 2006 |
| CD 104 | (A6 Antigen, ITGB4, integrin-beta-4, TSP-180, tumor-specific protein 180) | (Zhou L et al, 1999) |
| CD105 | (E9 protein, endoglin, FIHT3, hereditary hemorrhagic telangiectasia type 1, ORW, Osler-Rendu-Weber syndrome, ORW1, SFI-2) | (Vittal et al, 2005) |
| CD106 | (alpha-4-beta-1 ligand, INCAM-€10, inducible cellular adhesion molecule 110 kDa, VCAM-1, vascular cellular adhesion molecule 1) | (Michael et aI, 2008; Zhao X et al. 2004; Vittal et al, 2005) |
| CD107a | (LAMP-I, lysosome-associated membrane glycoprotein-1, LAMPA, lysosome-associated membrane glycoprotein A, LGP120, lysosomal glycoprotein 120) | (Rozsa et al, 2006) |
| CD141 | (thrombomodulin, TM, THBD, THRM, Alpha-Thrombomodulin, Beta-Thrombomodulin, fetomodulin, FM) | (Luna et al, 2009; BoггЛs et al 2006; . Rozsa et al, 2006; Zhao X et al, 2004) |
| CD143 | (ACB, angiotensin converting enzyme, angiotensin-1 converting enzyme, dipeptidyl carboxypeptidase, dipeptidyl carboxypeptidase 1, EC3.4, 15.1, kininase 2, peptidase P, peptidyl dipeptidase A) | (Savaskan et al, 2004) |
| CD146 | (A32, BT14, L101, gpl30 antigen, MCAM, Melanoma cell adhesion molecule, MeICAM, melanoma adhesion molecule, MUdS, P1H12, S-endo 1, Gicerin, 1-gicerin, s-gicerin)) | (Rozsa et al, 2006; Vittal et al, 2005 |
| CD164 | (endolyn, endolyn-78, MGC-24, multiglycosylated core protein-24, MGC-г4v, MИC-24) | (Rozsa et al, 2006) |
| CD 166 | (2117 antigen, ALCAM, Activated leukocyte cell adhesion molecule, BEN, CD6I., –100, DM-GRASP, F84.1 antigen, HCA, Hematopoietic cell antigen, IC7, KG-CAM, MEMD, melanoma metastasizing clone D, metastasizing melanoma protein D, MuSC, Neurolin, SC-1) | (Rozsa et al, 2006) |
| CD225 | (fragilis, IFI17, interferon-induced protein 17, IFITM1, interferon-induced transmembrane protein 1, 9-27, Interferon-inducible protein 9-27, Leu13) | (Zhao X et al, 2004; Rozsa et al, 2006) |
| CD249 | (6C3, aminopeptidase A, angiotensinase A, APA, L-alpha-aspartyl(L-alpha-glutamyl)-peptide hydrolase, BP-I, BP-1/6C3 antigen, EAP, EC3.4.11.7, glutamyl aminopeptidase, gp160, RC38, ENPEP) | (Coupland et al, 1993) |
| CED6 | (engulfment adaptor PTB domain containing 1, gulp, GULP1) | (Zbao X et al, 2004) |
| Chemerin receptor | (RARR.ES2, retinoic acid receptor responder 2, tazarotene-induced gene-2, TIG-2) receptors (ChemR23, chemokine receptor 23, CMKLR1, chemokine-like receptor 1, Dez) | (Luna et al 2009) |
| CH[3L1 | (chi. tinase 3-li1ce-1, cartilage glycoprotein 39, gp39; gp39k HC-gp39, chondrocyte protein YKL40, YKL40, Chondrex) | (Rozsa et al, 2006; Zhao X et al, 2004) |
| CH13L2 | (chitinase 3-1ike-2, YKL39) | (Rozsa et al, 2006 |
| CNTF receptor | Receptor for: Ciliary neuronotrophic factor, ciliary neurotrophic factor, MANS, membrane-associated neurotransmitterstimulating factor | Liu X et a1, 2001 |
| collagen type 4 | (COL4A1, collagen-4, collagen-4-alpha-1, Arresten, Canstatin, Tumstatin) | Junglas et al, 2009; Zhao X et al, 2004 |
| collagen type 14 | (collagen-14, COL14A1, coilagen-14-alpha-1, undulin) | Vittal et al, 2005; Zhao X et al, 2004 |
| collagen type 15 | (Collagen-15, COL15A1, collagen-15-a1pha-1, Restin, Restin-1, Rest'tП -2, Restin-3, Restin-4) | Rozsa et al, 2006; Fuchshofez et al, 2007 |
| complement factor C3 | (ECI, Eosinophil cytotoxicity inhibitor, C3-beta-c, complement factor C3b, ETF-3, embryotrophic factor-3, HSE-MSF, hepatic sinusoidal endothelial cell-derived migration stimulating factor | Michael et al, 2008 |

TABLE A-continued

| Protein Name | Alternative Names | Reference |
|---|---|---|
| C5PG2 | (chondroitin sulfate proteoglycan 4) | (Zhao X et al, 2004) |
| CSRP2 | :(Cysteine and glycine rich protein 2) | (Zhao X et at, 2004) |
| CTGF | (Connective tissue growth factor, Hcs24, hypertrophic chondrocyte-specific gene product 24, Fisp-12, fibroblast inducible secreted protein-12, IGFBP8, Insulin-like growth factor binding protein-8, 1GFBPrP2, Insulin-like growth factor binding protein related protein-2, Ecogenin, endochondral ossification genetic factor, CCN2) | (1unglas et al, 2009; Fuchshofer et al, 2007; Rozsa et al, 2006; Vittal et at, 2005) |
| CTGF Receptor | Receptor for: Connective tissue growth factor, Hcs24, hypertrophic chandrocyte-specific gene product 24, Fisp-12, fibroblast inducible secreted protein-12, 1GFBP8, Insulin-like growth factor binding protein-8, IGFBPrP2, lnsulin-like growth factor binding protein related protein-2, Ecogenin, endochondral ossification genetic factor, CCN2 | (7unglas et al, 2009) |
| C-type natriuretic peptide Receptor | Receptor for: CNP, ANP-C, NPPC | (Chang et at, 1996; Zhong L et a1, 2003) |
| CX3CL1 | (fractalkine, FK N, FK, CX3 C membrane-anchored chemokine, C3Xkine, neurotactin, NTT, NTN, ABCD-3, SCYD1) | (Luna et al, 2009) |
| CXCL I | (CXC chemokine ligand 1, cheznokine (C-X-C motif) ligand 1, SCYB i, CINC-1, Cytokine induced neutrophil chemoattractant-1, fsp, fibroblast secretory protein, GR01, GRO-alpha, K C, MGSA, melanoma growth stimulatory activity, MGSA-alpha, melanoma growth stimulatory activity-alpha, NAP-3, neutrophil-activating prote r Π -3, N51) | (Michael et al. 2008 |
| CXCL3 | (CXC chemokine ligand 3, chemokine (C-X-C motif) ligand 3, CLNC-2-beta, Cytokine induced neutrophil chemoattraetant-2-beta, DCIP-1, DC inflammatory protein-1, GR03, GR0-gamma, growth regulated oncogene-gamma, growth-related oncogene-3, MGSA-gamma, melanoma growth stimulatory activity-gamma, MIP-2-beta, macrophage inflammatory protein-2-beta) | (Michael et al, 2008) |
| CXCL5 | (CXC chemokine ligand 5, chemokine (C-X-C motif) ligand 5, ENA-78, Epithelial neutrophil-activating protein 78, epithelial cell-derived neutrophil attractant-78, LIX, LPS induced CXC chemokine, AMCF-2, Alveolar macrophage chemotactic factor-2, SCYB5) | (Michael et al, 2008) |
| CXCL6 | (CXC chemokine ligand 6, chemokine (C-X-C motif) ligand 6, GCP-2, granulocyte chemotactic peptide-2, CKA-3, chemokine alpha 3, SCY86) | (Michael et al, 2008) |
| CXCL12 | (CXC chemokine ligand 12, chemokine (C-X-C motif) ligand 12, 1RH, intercrine reduced in hepatomas, hIRH, intercrine reduced in hepatomas, SDF-1-alpha, SDF-1-beta, SDF, SDF-1, Stromal cell-derived factor, Stromal cell-derived factor-1-alpha, 5tramal cell-derived factor-1-beta. PBSF, pre-B-cell growth stimulating factor, TI.SF, Thymic lymphoma cell stimulating factor, Thymic lymphoma cell stimulating factor-alpha, Thyniic lymphoma cell stimulating factor-beta, TLSF-alpha, TL5F-beta, TPAR-1, TPA repressed gene-1, SCYB 12) | (Vittal et al, 2005; Zhao X et al, 2004) |
| Cystatin B | | (Rozsa et al, 2006) |
| Cystatin C | (CS'1'3, Cystafiin-3, Gamma-TRACE, post-gamma globulin)) | (Rozsa et al, 2006; Leung YF et al, 2003 |
| DAP-3 | (Death associated protein 3, MRP-529, mitochondrial ribosomal protein S29)) | (Rozsa et al, 2006 |
| DDR2 | :(discoidin domain receptor 2, NTRKR3, neurotrophic tyrosine kinase receptor-related 3, tyro[4, CD167b) | (Luna et al, 2009) |
| Dickkopf-1 | (dkk-1, dickkopf-related protein 1, Sk) | (Luna et al, 2009) |
| dicldcopf-2 | (dickkopf-related protein 2, dkk-2) | (Zhao X et al, 2004) |

| Protein Name | Alternative Names | Reference |
|---|---|---|
| DR6 | (death receptor-6, TNFRSF21, TNF receptor superfamily member 21) | (Zhao .X et al, 2004) |
| DRAK1 | (DAP kinase-related apoptosis-inducing protein kinase-1, STK17A, serinefthreonine protein kinase 17A) | (Rozsa et al, 2006) |
| EBAF | (Endometrial bleeding associated factor, TGF-beta-4, TCFB4, lefty A, iefty-2) | (Zhao X et al, 2004) |
| EGF | (epidermal growth factor, EGF-URO, HMGF, human milk growth factor, PGF, prostatic growth factor, beta-Urogastrone, URO, URG, Urogastrone, tooth-1id factor) | (He and Li, 2001; He X and Li M, 1997) |
| EGF Receptor | Receptor for; epidermal growth factor, EGF-URO, HMGF, human milk growth factor, PGF, prostatic growth factor, beta-Urogastrone, URO, URG, Urogastrone, tooth-lid factor (erb, erbB1, HER 1) | (Alexander et al, 1998; Dai W and Li M, 1997; He X and Li M, 1997; Wordinger et al, 1998) |

TABLE A-continued

| | | |
|---|---|---|
| Egr-1 | (Early growth response gene-1, ETR103, d2, zif2b8, NGFI-A, nerve growth factor-inducible A, Krox-24, GOS-30, 00(01 switch gene 30, T1S8, TPA-inducible sequence-8, tetradecanoyl phorbol acetate-inducible sequence-8) | (Fan et al, 2008) |
| egr-3 | (Early growth response geΠe-3) | (Luna et at, 2009) |
| Endocan | ESM-1, endothelial cell-specific molecule 1 | Luna et al, 2009; Fan et al, 2008; Zhao X et al, 2004 |
| endothelia-1 | (ET-1(1-21), ET-1) | (Zhang X et at, 2003) |
| endothelin-1 Receptor endothelin-1 receptiors | (ET-1(1-21), FT-i) receptors | (Rozsa et al, 2006; Zhao X et al, 2004 Thierne et al, 2005; Hague et al, 1998; Kageyama et al, 1996; Kohmato et al, 1994; Rosenthal et al, 2005; Tao W et al,1998; Zhang X et al, 2003; Fan et al, 2008; Abad et al, 2008) |
| EphA4 | (Eph receptor A4, Sek, 5eki, HEK 8, human embryo kinase-8, tyrol, tyrosine-protein kinase 1) | (Fan etal, 2008; Rozsa et al, 2006) |
| ephrin B2 | (EFNB2, HTK ligand, HTKL, EPLG5, EPH-related receptor tyrosine kinase ligand-5, LERK5, Ligand of eph-related kinase-5, NLERK1) | (Vittal et al, 2005) |
| Epiregulin | (EREG, EPR) | (Rozsa et al, 2006) |
| Erythropoietin Receptor | (Epo, Ep, ECSA, erythroid colony stimulating activity, ESF, erythropoiesis stimulating factor) receptor | (Rozsa et al, 2006; Vittal et al, 2005) |
| FADD | (FAS-associated death domain protein, MORT-1, CAPi, cytotoxicity-dependent APO-1-associated protein 1, CAi'2, cytotoxicity-dependent APO-1-associated protein 2) | (Luna et al, 2009) |
| FAM3C | (cytokine-Oke protein family with sequence similarity 3 member C; lnterleukin-like EMT inducer, 1LE1) | (Rozsa et aI, 2006) |
| FAP-alpha | (fibroblast activation protein, Fibroblast activation protein-alpha, FAP, FAPA, seprase, 5eprase-s, seprase-1) | (Zhao X et al, 2004) |
| ferritiii | (H-Ferritin, FTH1, FTH, L-Fenitin, FTL, CD-GF, carcinoma-derived growth factor) | (Ishibashi et al, 2002) |
| FGF-5 | (Fibroblast growth factor-5, HBGF-5, heparin binding growth factor-5. SMAG-82, smooth muscle cell activation-induced gene-82 | (Fuchshofer et al, 2009) |

| Protein Name | Alternative 1Sames | Reference |
|---|---|---|
| FGF1Z1 | (fibroblast growth factor receptor-1, BFGFR, basic fibroblast growth factor receptor, FGFBR, FGFB receptor, flt-2, fms-like tyrosine kinase-2, flg, fms-like gene, N-sam, Cekl, chicken embryonic kinase 1, KAL2, Katlniann syndrome 2, CD331) | (Rozsa et al, 2006) |
| fibroleukin | (T49, pT49, FGL2, fΓbrinogen-like-2, HEP64) | (Rozsa et al, 2006; Zhao X et at, 2003) |
| Fibromodulin | (FMOD, collagen binding 59 kDa protein) | (Vittal et al, 2005) |
| fibronectin | (FN, fibronectin-1, FNI, LETS, large external transformation-sensitive protein, Fibrobiast surface antigen, SF antigen, SFA, Cig, CI globulin, cold-insoluble globulin, CSP, galactoprotein A, MSF, migration stimulating factor, Z protein) | (Junglas et al, 2009; Yu et ci, 2008; Lin et al, 2007; Vitial et ci, 2005; Fuchshofer et at, 2007; Sato and Roy, 2002; Steely et at, 1992; Worthen and Cleveland, 1982; Yue et at, 1990; Zhou L et al, 1998) |
| fibronectin receptor | (FN, fibronectin-1, FN1, LETS, large external transformation-sensitive protein, Fibroblast surface antigen, SF antigen, SFA, CIg, CI globulin, cold-insoluble globulin, CSP, galactoprotein A, MSF, migration stimulating factor, Z protein) receptors | (Calthorpe and Grierson, 1990) |
| Fibulin-1 | (FBLNI, BM-90) | (lshibashi et ai, 2002) |
| Fibulin-5 | (FBLN5, DANCE, developmental arteries and neural crest EGF-like, EVEC, embryonic vascular EGF-like repeat-containing protein) | (Zhao X et at, 2004) |
| follistatin | (FST, Follicle stimulating hormone suppressing protein, FSP, Activin-binding protein) | (Rozsa et at, 2006) |
| follistatin-like-1) | (TSC-3 6, TGF-beta-stimulated clone-36, follistatin-related protein, FRP, follistatin-like, occi, Flik, XFRP, *Xenopus laevis* follistatin-related protein | (Rozsa et al, 2006) |

TABLE A-continued

| | | |
|---|---|---|
| FLRG | (follistatin-related gene, follistatin-like-3, P'STL3) | (Fuchshofer et al, 2009; Rozsa et al, 2006; Zhao X et al, 2004; Ishibashi et at, 2002) |
| FPR1 | (formyl peptide receptor-1, fMLP receptor, FRP, N-formyl peptide receptor, formyl peptide receptor) | (Rozsa et al, 2006) |
| frizzled-7 | (FzB7, Fz7, FzE3) | (Zhao X et al, 2004) |
| gadd45-alpha) | (growth arrest and DNA damage induced gene-45-alpha, gadd45A, DDIT1, DNA damage-inducible transcript-1 | (Rozsa et al, 2006) |
| gadd45-beta | (growth arrest and DNA damage induced gene-45-beta, gadd45B, MyD118) | (Rozsa et al, 2006) |
| gadd 153 | (growth arrest and DNA damage induced gene-153, DD1T3, DNA damage-inducible transcript-3, CHOP, C/EBP-homologous protein, CHOP-iD, CtEBP-homologous protein-tO, C/EBP-reta, CCAAT/enhancer binding protein zeta) | (Leung YF et at, 2003) |
| galanin | (GAL, GALN, GLNN) | (Luna et al, 2009) |
| Galectin-I | (Gal-1, LGALS1, galactose-specific soluble lectin 1, L-14-I, Lactose-binding lectin I, S Lac lectin 1, Galaptin) | (Zhao X et at, 2004) |
| GAP43 | (growth associated protein 43, 3-50, 3D5 antigen, F1, pp46, P57, 7-5, p54(Ca)p, GAP48, neuromodulin) | (Rozsa et al, 2006) |
| gas-1 | (Growth arrest-specific gene-1) | (Fan et al, 2008; Zhao X et at, 2004; Leung YF et al, 2003; $oII as et at 2006) |

| Protein Name | Alternative Names | Reference |
|---|---|---|
| gas-7 | (Growth arrest-specific gene-7) | (Rozsa et al, 2006) |
| glypican-4 | (GPC4, K-glypican) | (Luna et at, 2009; Zhao X et at, 2004) |
| gp130 | (IL6ST, IL6 signal transducer, CDI30) | (Rozsa et al, 2006) |
| greIIilin-2 | (GREM2, PRDC, protein related to DAN and cerberus, CKTSF1B2, DAND3) | (Rozsa et at, 2006) |
| HB-EGF | (Heparin binding EGF-like factor, Heparin binding EGF-like growth factor, paΓ-2, prostate apoptosis response protein 2, DTR, Diphtheria toxin receptor) | (Fuchshofer et al, 2009; Zhao X et al, 2004) |
| HDGF | (hepatoma-derived growth factor, HuHGF, HMG 1 L2, high mobility group protein I-1ike-2) | (Rozsa et al, 2006) |
| HGF receptor | (hepatocyte growth factor, HGF/SF, Hepatocyte growth factorscatter factor, F-TCF, fibroblast tumor cytotoxie factor, HPTA, Hepatopoietin A, SF, scatter factor, TCF, tumor cytotoxic factor) | (Rozsa et at, 2006; Zhao X et al, 2004) |
| HGF receptor | (hepatocyte growth factor, HGF/SF, Hepatocyte growth factorscatter factor, F-TCF, fibrobiast tumor cytotoxic factor, HPTA, Hepatopoietin A, S$^P$', scatter factor, TCF, tumor cytotoxic factor) receptors (met) | (Alexander et al, 1998; Wordinger et al, 1998) |
| HMG-1 | (high mobility group protein-3, HMGB1, high mobility group box-1, amphoterin, DEF, Differentiation enhancing factor, Neurite growth-promoting protein, SBP-1, Sulfoglucuronyl carbohydrate binding protein-1) | (Ishibashi et al, 2002) |
| hsp27 | (hsp27a, hsp27b, hsp27c, heat shock protein 27, H5PB i, heat shock 27 kDa protein I, estrogen-regulated protein 24K. $p^{29}$ estrogen receptor-associated protein, estrogen receptor-related protein, GC1, germ ceH-dependentphosphoprotein-1) | (Zhao X et al, 2004; Rozsa et al, 2006) |
| hsp70 | heat shock protein 70 | Luna et al, 2009 |
| HSPA5 (heat shock 70 kDa protein 5, glucose | regulated protein 78, GRP7$) | (Leung YF et al, 2003) |
| HVEM | (Herpesvirus entry mediator, HveA, Herpes simplex virus entry protein A, EiveAt, , TR2, TNF receptor~like-2, ATAR, another TRP.F-associated receptor, TNFRSFI4, TNF receptor superfamily member 14, LIGHTR, LIGHT receptor) | (Tiwari et al, 2005) |
| ID4 | (Inhibitor of DNA binding-4, inhibitor of DNA binding/differentiation-4, iDB4) | (Rozsa et al, 2006) |
| 1FI16 | (interferon~induced protein 16, interferon-gamma-inducible protein-16) | (Rozsa et al, 2006) |
| IFITM3 | (interferon-induced transmembrane protein 3) | (Rozsa et al, 2006) |
| IFN-gamma receptor 2 | (interferon-gamma transducer 1) | (Luna et al, 2009) |
| IGF-1 | (Insulin-like growth factor-I, &ytluopoietic factor, mechano growth factor, MGF, ILGF1, somatomedin C, NSILA, non-suppressible insulin-like activity, Somatomedin A, Somatomedin C, sulfation factor) | (Cao V et al, 2002; Rozsa et al, 2006; Zhao X et al, 2003) |
| IGF-1 receptor | (Insulin-like growth factor-1, Erythropoietic factor, mechano growth factor, MGF, ILGF'1, somatomedin C, NSII.,A, non-suppressi$^b$Ie insulin-like activity, 5oniatornedin A, 5omatomedin C, sulfation factor) receptors (IGF1R, CD221) | (Ando et al1, 2004; Cao Vet al, 2002; Wordinger et al, 1998) |

TABLE A-continued

| | | |
|---|---|---|
| IGF-2 | (Insulin-like growth factor-2, Growth-promoting activity for vascular endothelial cells, T3M-11-derived growth factor, ILGF2, MSA, multiplication stimulating activity, NSILA, non-suppressibe insulin-like activity, Somatomedin A, sulfation factor, SGF, skeletal growth factor, HP1-SMP, HP3 -5MP, Somatomedin/insulin-like growth factor-like polypeptides) | (Rozsa et at, 2006) |

| Protein Name | Alternative Names | Reference |
|---|---|---|
| IGF-2 receptor | (Insulin-like growth factor-2, Growth-promoting activity for vascular endothelial cells, T3 M-11-derived growth factor, ILGF2, MSA, multiplication stimulating activity, NSILA, non-suppressible insulin-like activity, Somatomedin A, sulfation factor, 5GF, skeletal growth factor, HP1-8MP, I-IP3-5MP, Somatomedin/insulin-like growth factor-like polypeptides) receptors (IGF2R, CD222, mannose-6-phasphate receptor; tvIPR, CIM6PR, cation-independent mannose 6-phosphate receptor, MPRI, MPR300) | (Rozsa et al, 2006) |
| IGFBP2 | (Insulin-like growth factor binding protein-2) | (Fan et al, 2008; Ishibashi et al, 2002; Leung YF et al, 2003; Rozsa et al, 2006; Vittal et al, 2005) |
| IGFBP3 | (Insulin-like growth factor binding protein-3, BP-53, Growth hormone dependent binding protein, Binding protein-29) | (Fan et al, 2008; Rozsa et al, 2006; Zhao X et at, 2004 |
| 1GFBP4 | (Insulin-like growth factor binding protein-4, Colon cancer cell growth inhibitor, I-IT29-IGFBP, HT29 insulin-like growth factor binding protein) | (Ishibashi et al, 2002; Rozsa et al, 2006; Vittal et at, 2005) |
| IGFBP5 | (Insulin-like growth factor binding protein-5) | (Michael et al, 2008; Rozsa et al, 2006) |
| 1CT5F4 | ⌈immunoglobuiin superfamily gene 1⌋ | (Zhao X et at, 2004) |
| ILI-alpha | (ILIA, interleukin-l-alpha, BAF, B-cell activating factor, BCAF, B-cell activating factor, EP, endogenous pyrogens, LAF, lymphocyte activating factor, LEM, leukocyte endogenous mediator, MCF, mononuclear cell factor, MNCF, mononuclear cell factor, MP, mitogenic protein, TRF-3, T-cell replacing factor-3, Tumor inhibitory factor-2) | (Luna et al, 2009; Li et al, 2007) |
| IL1-alpha receptor | (IL1A, interleukin-I-alpha, BAF, B-cell activating factor, BCAF, B-ceff activating factor, EP, endogenous pyrogens, LAF, lymphocyte activating factor, LEM, leukocyte endogenous mediator, MCF, mononuclear cell factor, MNCF, mononuclear cell factor, MP, mitogenic protein, TRF-3, T-cell replacing factor-3, Tumor inhibitory factor-2) receptors (IL1R, 1L112A, IL1R1, IL1 receptor type 1, IL1RB, 1L1R2, ILI receptor type 2, CD121a, CD121b) | (Kelley et al, 2007; Li XY et al 2006; Alexander et al, 1998; Fleenor et al, 2003; Pang et al, 2003; Wordinger et al, 1998; Keller et al, 2009) |
| II.1-beta | (ILIB, interleukin-i-beta, Catabolin, Hl, Hematopoietin-1, IFN-beta inducing factor, Interleukin-beta, OAF, osteoclast activating factor) | (Fan et al, 2008) |
| IL1-beta receptor | (IL1B, interleukin-l-beta, Catabolin, HI, Hematopoietin-1, 1FN-beta inducing factor, Interleukin-beta, OAF, osteoclast activating factor) receptors (IL1R, ILIRA, IL1R1, ILI receptor type 1, IL1RB, ILiR2, II., I receptor type 2, CD121a, CD121b) | (Alexander et al, 1998; Wordinger et al, 1998) |
| ILI-beta Convertase | (ICE, IL1BC, IL1-beta converting enzyme, Caspase-1, CASP1) | (Agarwal et al, 1999) |
| IL4 receptor | Interleukin-4, BCDF-epsilon, B-cell differentiation factor-epsilon, BCDF-gamm.a, B-call differentiation factor-ganⅡna, BCGF-gamrua, B-cell growth factor-gamma, BCGF-1, B-cell growth factor-I, Binetrakin, BSF-1, B-cell stimulating factor-1, BSF-p1, B-cell stimulating factor pl, EL4-BCGF, EL4 B-cell growth factor, HCGF, Hodgkin's call growth factor, 1gE-EF, IgE enhancing factor, IgG1-enhancing factor, IgG1-induction factor, LMW-BCGF, low molecular weight B-cell growth factor, MaGEF, Mast cell growth enhancing factor, MCGF-2, mast cell growth factor-2, MFF, macrophage fusion factor, Pitrakinra, TCGF-2, T-ceH growth factor-2) receptors (CD 124) | Rozsa et al, 2006 |

TABLE A-continued

| Protein Name | Alternative Names | Reference |
| --- | --- | --- |
| 1L6 | (interleukin-6, 26 kDa protein, BSF-2, B-cell stimulating factor-2, CDF, CAT development factor, chollne acetyltransferase development factor, Cytolytic differentiation factor for T-lymphocytes, FDGI, fibroblast-derived growth inhibitor, HGF, hybridoma growth factor, HPGF, hybridoma/plasmacytoma growth factor, 1-iSF, hepatocyte stimulating factor, HSF-1, hepatocyte stimulating factor-1, ILHP1, lnterleukin-hemopoietin-1, MGI-2A, Macrophage-granulocyte inducer-2A, Myelorna GF, mycloma growth factor, NKAF, natural killer cell activating factor, TAF, T-ce11 activating factor, Thymocyte growth factor, TSF, thymocyte stimulating factor) | (Liton et al, 2009; Luna et al, 2009; Li et al, 2007; Rozsa et al, 2006) |
| 1L6 receptor | (interleukin-6, 26 kDa protein, BSF-2, B-cell stimulating factor-2, CDF, CAT development factor, choline acetyltransferase development factor, Cytolytic differentiation factor for T-lymphocytes, FDGI, fibroblast-derived growth inhibitor, HGF, hybridoma growth factor, HPGF, hybridoma/plasmacytoma growth factor, HSF, hepatocyte stimulating factor, HSF-1, hepatocyte stimulating factor-I, ILHP1, Interleukin-hemopoietin-1, MG1-2A, Macrophage-granulocyte inducer-2A, Myeloma GF, myeloma growth factor, NKAF, natural killer cell activating factor, TAF, T-cell activating factor, Thymocyte growth factor, TSF, thymocyte stimulating factor) receptors (C17t26) | (Liton et al, 2009) |
| IL-8 | interieukin-8, SCYBB, 3-19C, 9E3, ANAP, anionic neutrophil-activating peptide, Chemotaxin, CEF-4, CT/IL8, CXCL8, CXC chemoicine ligand 8, chemokine (C-X-C motif) ligand 8, EDNAP, endothelial-derived neutrophil-activating peptide, EMF-1, embryo fibroblast protein 1, Emoctakin, ENAP, Endothelial cell neutrophil-activating peptide, FDNAP, Fibroblast-derived neutrophil-activating peptide, FINAP, fibroblast-deriyed neutrophil-activating protein, GCF, granulocyte chemotactic factor, GCP, granulocyte chemotactic peptide, LAI, leukocyte adhesion inhibitor, LCF, lymphocyte chemotactic factors, LDNAP, leukocyte-derived neutrophil-activating peptide, LIF, leukocyte in6ibitory factor, LUCT, lung carcinoma-derived chemotaxin, LYNAP, lymphocyte-derived neutrophil-activating peptide, MDNAP, monocyte-derived neutrophil-activating peptide, MDNCF, monocyte-derived neutrophil chemotactic factor, MOC, monocyte-derived chemotaxin, MONAP, monocyte-derived neutrophil-activating peptide, NAF, neutrophil-activating factor, NAP-1, neutrophil-activating prot.ein-1, NCF, neutrophil chemotactic factor, NCP, neutrophil chemotactic protein, PLF, psoriatic leukotactic factor, TCF, T-cell chemotactic factor, TSG-1, Tumor necrosis factor-stimulated gene sequence-i) | (Luna et al 2009; Michael et al, 2008; Li et al, 2007; Ishibashi et al, 2002) |
| 1L10 receptor | Receptor for interleukin-10, B-TCGF, B-cell derived T-ce11 growth factor, CSIF, cytokine synthesis inhibitory factor, TG[F, T-ce11 growth inhibitory factor | (Rozsa et al, 2006) |
| IL12 | IL12A, IL12-alpha IL12B, 1L12-beta, IL.12-p35, 1L12-p40, ILL2-p70, Intaerleukin-12, Interleukin-12A, Interleukin-12B, CLMF, cytotoxic lymphocyte maturation factor, NKSF, natural killer cell stimulating factor, NKSF1, natural killer ce11 stimulatory factor-1, NKSF2, natural killer cell stimulatory factor-2, TcMF, CTL maturation factor, TSF, T-celi stimulating factor | (Zhao X et al, 2004) |
| IL13 receptors insulin receptors integrin alpha integrin beta | Receptor for Interleukin-13, NC30, P600 (CD220, INSR) | (Rozsa et al, 2006) (Kim, 2007) |
| IRAK1 | (IL1 receptor-associated kinase-1, Il2AK, IL1 receptor-associated kinase) | (Rozsa et al, 2006) |

| Protein Name | Alternative Names | Reference |
| --- | --- | --- |
| ITGBLI | integrin beta-1 | Rozsa et al, 2006 |
| ITM2B | (integral membrane protein 21₃ ; B12I) | (Rozsa et al, 2006) |
| jagged-1 | (7AG1, jagged, Serrate-1) | (Ishibashi et al, 2002) |
| JAM3 | (Junctional adhesion molecule 3, JAM-C, Junctional adhesion molecule C, Gi 11 antigen) | (Rozsa et al, 2006) |
| KGF receptors | Receptor for keratinocyte growth factor, HBGF-7, heparinbinding growth facto.r-7, FGF-7, fibroblast growth factor-7 | (Alexander et al, 1998) |
| Leptin receptor | (receptors for ob, oh/oh, obese protein, obesity factor) (OBR, CD295, db, dbldb, fatty, fa, fa/fa) | (Zhao X et al, 2004; Rozsa et al, 2006) |
| LIF | (ABAE cell growth-inhibitory activity; CDF, cholinergic differentiation factor, CNDF, cholinergic neuronal differentiation factor, D-Factor, differentiation stimulating factor, DIA, differentiation inhibiting activity, DIF, differentiation inducing factor, DRF, Differentiation-retarding factor, ES cell growth factor, ESCGF, embryonic stem cell growth factor, GATS, growth | (Rozsa et al, 2006) |

TABLE A-continued

|  |  |  |
|---|---|---|
|  | stimulatory activity for TS i cells, HILDA, human interleukin for Da cells, HSF-2, hepatocyte stimulating factor-2, HSF-3, hepatocyte stimulating factor-3, Lipoprotein lipase inhibitor, Ml differentiation inducing activity, MCGEF, mast cell growth-enhancing factor, MLPLI, melanoma-derived lipoprotein lipase inhibitor, OAF, osteoclast activating factor) |  |
| LIF receptor | (ABAE cell growth-inhibitory activity; CDF, cholinergic differentiation factor, CNDF, cholinergic neuronal differentiation factor, D-Factor, differentiation stimulating factor, DIA, differentiation inhibiting activity, DIF, differentiation inducing factor, DRF, Differentiation-retarding factor, ES cell growth factor, ESCGF, embryonic stem cell growth factor, GATS, growth stimulatory activity for TS I cells, HILDA, human interleuk'in for Da cells, HSF-2, hepatocyte stimulating factor-2, HSF-3, hepatocyte stimulating factor-3, Lipoprotein lipase inhibitor, MI differentiation inducing activity, MCGEF, mast cell growth-enhancing factor, MLFLI, melanoma-derived lipoprotein lipase inhibitor, OAF, osteoclast activating factor) receptors (CDI18) | (Alexander et al, 1998) |
| LTBP1 | (Latent TGF-beta binding protein-1) | (Fuchshofer et al, 2009) |
| LTBP2 | (Latent TGF-beta binding protein-2) | (Fuchsliofer et al, 2009; Vittal et al, 2005) |
| MAGEH1 | (melanoma antigen family Hl, Melanoma-associated antigen Hl, APR1, Apoptosis-related protein-1) | (Rozsa et al, 2006) |
| Metallothionein-3 | (MT-3, GIF, growth inhibition factor, GIFB, growth inhibitory factor brain, GRIF, neuronal growth inhibition factor) | (Rozsa et al, 2006) |
| metallothioneins |  | (Fan et al, 2008; Vittal et al, 2005; Leung YF et al, 2003) |
| MFG-E8 | (Milk fat globule epidermal growth factor-8, Lactadherin, BA46, GP55, Component 15/16, MGP57/53, rnedin, FDC-M1, SED1, secreted EGF repeat and discoidin domains containing protein 1) | (Rozsa et al, 2006) |
| MIC1 | (macrophage inhibitory cytokine-1, GDF15, growth/differentiation factor-15, FL74, PTGF-beta, Placental Transforming Growth Factor-beta, PDF, prostate-derived factor, PLAB, Placental bone morphogenetic protein, NAG-I, NSFi, ID activated gene-1) | (Rozsa et al, 2006; Vittal et at, 2005) |

| Protein Name | Alternative Names | Reference |
|---|---|---|
| MMP-1 | (matrix metalloproteinase-1, collagenase, collagenase-1, CL-1, CLG1, fibroblast collagenase, FΓbroᵇ Iast-type collagenase, interstitial collagenase, tissue collagenase, EC3.4.23.7) | (Alexander et al, 1998; Borr~s et al 2006; Oh et at, 2006; Pang et al, 2003; Rozsa et ii, 2006) |
| MMP--2 | (matrix metalloproteinase-Z, EC3.4,24.24, 70 kDa gelatinase, 72 kDa gelatinase, 72 kDa metalloproteinase, coHagenase type 4, collagenase type 4A, 72 1cDa type IV collagenase, Gelatinase 72 kDa, Gelatinase A, Type IV collagenase, Type IVA collagenase, neutrophil gelatinase) | (Fatma et al, 2009; 7unglas et iiI, 2009; Yn et al, 2008; sanka et al, 2007; WuDunn, 2001; Conlay et al, 2004; Husain et al, 2007; Kashiwagi et al, 2001; Oh et al, 2006; Shearer and Crosson, 2001; Shearer imd Crosson, 2002) |
| MMP-3 | (matrix metaꟈ loproteinase-3, stromelysin-1, STMY1, STRt, SL-1, transin, transin-1, collagenase activating protein, procollagenase activator, proteoglycanase) | (Luna et a1, 2009; KeHey et al, 2007; Fleenor et al, 2003; Oh et aI, 2006; Pang et al, 2003; Alexander et al, 1998; WuDunn, 2001) |
| MMP-9 | (matrix metalloprateinase-9, EC3.4.24.35, gelatinase B, 92 kDa gelatinase, 92 kDa type IV collagenase, or PMNL gelatinase, polymorphonuclear leulcocyte gelatinase, gelatinase type IV-13, collagenase type 5, callagenase-5, CL-5) | (dunglas et al, 2009; Alexander et al, 1998; Webb et xl, 2006; Pang et al, 2003) |
| MMP-10 | (matrix metalloproteinase-10, stromelysin-2, STMY2, SL-2, ST-2, transin-2, EC3.4.24.22) | (Luna et al, 2009) |
| MMP-11 | (matrix metalloproteinase-11, stramelysin-3, 5'1'MY₃ , SL-3, S'I'-3) | (Oh et al, 2006) |

TABLE A-continued

| | | |
|---|---|---|
| MMR-12 | (matrix rnetalloproteinase-12, macrophage elastase, macrophage metal1oe1astase, EC3.4.24.65, MME, HME) | (Oh et al, 2006) |
| MMP-14 | (matrix metalloproteinase-14, MT1-MMP, Membrane-type matrix metalloproteivase-1, MT-MMP-1, MMP-X1) | (Sanka et al, 2007; Miller et al, 2007; Oh et al, 2006) |
| MMP-15 | (matrix metalloproteinase-15, MT2-MMP, Membrane-type matrix metalloproteinase-2, MT-MMP-2) | (Oh et al, 2006; Vittal et al, 2005) |
| MMP-16 | (matrix metalloproteinase-16, MT3-MMP, Membrane-type matrix metalloproteinase-3, MT-MMP-3) | (Oh et at, 2006; Rozsa et al, 2006; Vittal et al, 2005) |
| MMP-17 | (matrix metalloproteinase-17, MT4MMP, Membrane-type matrix metalloproteinase-4, MT-MMP-4) | (Oh et al, 2006) |
| MMP-19 | (matrix metalloproteinase-19, RASI-1, rheumatoid arthritis synovium intlamed-1) | (Oh et al, 2006) |
| MMP-24 | (matrix metalloproteinase-24, MT5-MMP, Membrane-type matrix metalloproteinase-5, MT-MMP-5) | (Oh et al, 2006) |
| MNSF-beta | monoclonal nonspecific suppressor factor, hNSF, NSF, Nonspecific suppressor factor, MNSF-beta, Fau protein, Ubi-L, FSR-MuSV-associated ubiquitously expressed gene, fox, ♪B3, asrl, arsenite resistance-1) | (Rozsa et at, 2006) |
| Mortalin | (p66-ΓΠot-1, PBP74, pept'sde binding protein 74, grp75, glucose regulated protein 75) | (Luna et al, 2009) |

| Protein Name | Alternative Names | Reference |
|---|---|---|
| Mx | (rnyxovirus resistance 1, Mxl, MxA, 1F1-78k, interferon-inducible 78 kDa protein; IFI-78) | (Michael et at, 2008; Zhao X et al, 2004) |
| MyD88 | | (Rozsa et al, 2006) |
| Myocilin | (MYOC, T1GR, trabecular meshwork inducible GC response, trabecular meshwork inducible glucocorticoid response, GLC1A, JOAG, .10AG1) | (Clark et al, 2001; Fan et al, 2008; Fautsclt et ai, 2005; Hardy et al, 2005; Hoffman et al, 2009; Ishibashi et at, 2002; Kirstein et al, 2000; Lin et al, 2007; Nguyen et al, 1998; Ohazawa ci al, 2004; Pfeffer et al, 2009; Polansky at al; 2000; Rozsa at al, 2006; Sakai et al, 2007; Schlunck et al, 2008; Sohn at ai, 2002; Takahashi et al, 1998; Takahashi et al, 2000; Taniguchi et at, 2000; Ueda et al, 2000; Wentz Hunter et al, 2002; Zhao X et al, 2003) |
| Myocilin receptors | Receptor for (MYOC, TIGR, trabecular meshwork inducible GCresponse, trabecular meshwork inducible glncocorticoid response, GLC1A, 7OAG, 70AGI) | (Wentz Hunter et al, 2004) |
| NALP1 | (NACHT-LRR-PYD-containing protein-1, DEFCAP, death effector filament-forming CED4-like apoptosis protein, CARD7, caspase recruitment domain-containing protein-7, KIAA0926, NAC, nucleotide-binding domain and CARD containing protein, NLRP1, NLR family, pyrin-domain containing 1) | (Rozsa et al, 2006) |
| N-cadherin | (Neural cadherin, Cadharin-2, CDH2, A-CAM, adherens junction cell adhesion molecule, CDHN, neural calcium-dependent adhesion protein, CD325) | (Zhao X et al, 2004) |
| NELL-2 | (NEL-like 2, neural epidermal growth factor-like 2, NEL-like protein 2, NRP2, Ne1-related protein 2) | (Vittal et al, 2005) |
| Neuregulin-1 | (NRG-1, GGF, Glia1 growth factor, GGF-1, glial growth factor-1, NDF, rico differentiation factor, Acetylcholine receptor inducing activity, ARIA, Heregulin, heregulin-alpha, HGL, HRGA) | (Zhao X et al, 2004) |
| neuron-specific enolase | (NSE, Gamma-enolase, EC4.2.1.11, Enolase-2, ENO2, phosphopyruvate hydratase) | (Rozsa et al, 2006) |
| neuropeptide Y receptors | Receptor for NPY, Y Neuropeptide | (Luna et al, 2009) |
| neuropilin-1 | Neuropilin, NPN-1, NP-1, NRPI, A5-antigen, BDCA4, Blood dendritic call antigen 4, VEGF-165R, CD304) | Fuchshofer at al, 2009; Zhao X et al, 2004; Rozsa et al, 2006 |

TABLE A-continued

| | | |
|---|---|---|
| Nexin-1 | PN-1-alpha, Glia1-derived neurite promoting factor, GdNPF, Glia-derived nexin, GDN, NPP, neurite-promoting factor, Serpin E2 | Rozsa et at, 2006 |
| NG2 | (neuronal/glia12, AN2, MCSP, melanoma chondroitin sulfate proteoglycan, rnel-CSPG, MCSPG, melanoma chondroitin sulfate proteoglycan, CSPG4, chondroitin sulfate proteoglycan 4) | (Luna et al, 2009; Vittal at al, 2005) |

| Protein Name | Alternative Names | Reference |
|---|---|---|
| NGF | (nerve growth factor, 7S NGF, 7S nerve growth factor, NGF-alpha, Nerve growth factor-alpha, kallilcrein K1klb4, K1k1b4, NGF-beta, NG173, Nerve growth factor-beta, NGFG, NGF-gamma, Nerve growth factor-gamma, kallikrein Klklh3, K1k1b3) | (Wordinger et al, 2000) |
| NKEF-B | (Natural killer enhancing factor B, Peroxiredoxin-2, PRDX2, P1tX2, TDPX 1, thioredoxin-dependent peroxide reductase-1, Calpromotin, PRP, protector protein, Torin, TSA, thiol-specific antioxidant protein) | (Miyamoto et al, 2009; Vittal et al, 2005) |
| NKG7 | (natural killer cell group 7 sequence, natural killer cell protein 7, GiG1, G-CSF-inducedgene 1 protein) | (Vittal et al, 2005) |
| Norrin | (NDP, Norrie disease protein, EVR2, exudative vitreoretinopathy 2 protein, FEVR, familial exudative vitreoretinopathy) | (Rozsa et al, 2006) |
| NRAGE | (Neurotrophin receptor-interacting MAGE homolog, MAGED 1, melanoma antigen family D1, Melanoma-associatad antigen D], Dlxin-1) | (Rozsa et al, 2006) |
| NT-3 | (neurotrophin-3, ueuronotrophin-3, neurotrophic factor-3, NTF-3, HDNF, hippocampus-derived neurotrophic factor, NGF-2, Nerve growth factor-2) | (Wordinger et al, 2000) |
| NT-4 | (neurotrophin-4, neuronotrophin-4, neurotrophic factor-4) | (Wordinger et al, 2000) |
| 01P-1 | (osteoclast inhibitory peptide-1, TSA-1, thymic shared antigen-1, Sca-2, stem cell antigen-2, 9804, RIG-E, retinoic acid induced E, LY6E, lymphocyte antigen 6E, lymphocyte antigen 67, Ly67) | (Rozsa et al. 2006) |
| osteoglycin | (OGN, OIF, osteoinductive factor, K5PG25, Mimecan) | (Luna et al, 2009; Vittal et al, 2005; Zhao X et al, 2004) |
| osteoprotegerin | (OPG, FDCR-1, FDC-derived receptor-1, OCIF, osteoclastogenesis inhibitory factor, OCIFIOPG, OPG/OC1F, TNFRSFI 1B, TNF receptor superfarnily member 1 lB. TR1, TNF reeeptor-like-1) | (Rozsa et ai, 2006) |
| PA'-1 | Plasminogen activator inhibitor-1, PAI, plasminogen activator inhibitor, endothel'€ a1 plasminogen activator inhibitor, Serpin El, MSP', monocyte suppressor factor, ElF-i, EGF-inducible protein], roesosecrin | Fuchshofer et al, 2007; Fuchshofer et al, 2009; Junglas et al, 2009; Vittal et al, 2005; Fukuchi et al, 1997; Rozsa et al, 2006; Zhao X et al, 2004 |
| PA?P-A | pregnancy-associated plasma protein-A, Pappalysin-1, IGFBP4protease | Rozsa et al, 2006 |
| PDGF receptors | Receptor for platelet-derived growth factor, PDGF-1, PDGF-2, PDGF-A, PDGF-AA, PDGF-B, PDGF-BB, FDGF, fibroblast-derived growth factor, GDGF, glioma-derived growth factor-1, GDGF-2, glioma-derived growth factor-2, GSM, Glucocorticoid-suppressible mitogenic activity, MDF, mesangial cell proliferating factor, MDGF, monocyte-derived growth factor, OBIF, osteoblastogenesis inhibitory factor, ODGF, osteosarcorna-derived growth factor, T47D factor) | (Alexander et al, 1998; Vittal et al, 2005; Ando et al, 2004; Wordinger et al, 1998; Shearer and Crosson, 2001; tlsui et al, 2003; Zhao X et al, 2004) |
| PDGF-D | (platelet-derived growth factor-D, lris-expressed growth factor, IEGF, SCDGF-B, Spinal cord-derived growth factor-B) | (Zhao X et al, 2004) |
| Pentraxin-3 | Peutaxia-3, PTX3, TNFAIPS, tumor necrosis factor-alpha-induced protein 5, pentraxin-related gene rapidly induced by IL1-beta, TSG-14, tumor necrosis factor-stimulated gene sequence-14 | Luna et al, 2009; Zhao X et al, 2004 |
| periostin | POSTN, OSF-2, osteoblast-specific factor-2, periostin-like factor, PLP | Zhao X et al, 2004; Vittal et al, 2005 |
| PERP | p53 apoptosis effector related to Plv1P-22, TP53 apoptosis effector, KCP1, keratinocyte-associated protein 1, T1-lW | Rozsa et al, 2006 |

| Protein Name | Alternative Names | Reference |
|---|---|---|
| plexin-C1 | PLXNCI, VESPR, virus-encoded semaphorin protein receptor, CD232 | |
| perf⁊rin-1 | pore-forming protein-1, perforin, pore-forming protein, PFP, PFN, PRF 1, PFN 1 | Fan et al, 2008 |
| PR.ELP | _prolinelarginine-rich end leucine-rich repeat protein, prolargin | Rozsa et at, 2006) |
| proenkephalin | | Michael et al. 2008 |
| PTHrP | parathyroid hormone-like related protein, PTH-related protein, parathyroid hormone-related protein, PTHR, PTH-related peptide, Parathyroid hormone-related peptide, parathyroid hormone-like hormone, PTHLH | (Luna et a1, 2009) |

TABLE A-continued

| | | |
|---|---|---|
| RG54 | regulator of G-protein signaling 4 | Rozsa et al, 2006 |
| S100A10 | Calpactin-1 light chain, CALIL, Calpactin pI 1, CLP I i, p11. 42C, NGF-induced protein 42C, Annexia-2ligand, ANX2LG | Rozsa et al, 2006 |
| S 100A11 (calgizzarin, 5100C, MLN70, EMAP-1, Endothelial-monocyte activating polypeptide-I, EMAP, Endothelial | monocyte activating polypeptide, Meth A factor) (Zhao X et al, 2004) | |
| S10flAl2 Q( ) | pG, CGRP, calgranulin-related protein, Calgranulin C, CAAF-1, calcium-binding protein in amniotic fluid-1, ENRAGE, extracellular newly identified RAGE-binding protein, CO-Ag | Fan et al, 2008 |
| S100A13 | | Rozsa et al, 2006 |
| SDF-3 | Stromal cell-derived factor-3 | Rozsa et al, 2006 |
| Secretoneurin | SN, Chromogranin C, CHGC, SCG2, SgII, Secretogranin-2, gonadotrope polypeptide, GP-87, '1'SP86184, tyrosine-sulfated protein 86/84 kDa | Leung YF et al, 2003; Rozsa et al, 2006; Ishibashi et ai, 2002 |
| Semaphorin 3 A | SEMA3A, SEMA1, Semaphorin 3, sema III, collapsin-1, coil-i, Hsema-I, Semaphorin D, Sem D, SEMAD | Rozsa et al, 2006 |
| Semaphosin 3F | SEMA3F, Semaphorin 4, SEMA4, sema IV, Semaphorin K, SEMAK | Rozsa et al, 2006 |
| Semaphorin 6A | SEMA6A, Semaphorin Q, SEMAQ | Rozsa et al, 2006; Fan et al, 2008 |
| serum amyloid A | serum amyloid A, SAA, SAM, serum amyloid Al, SAA2, serum amyloid A2, SAAL, A-SAA, acute phase serum amyloid A | Fan et al, 2008; Rozsa et al, 2006 |
| sFRP1 | secreted frizzled-related protein I. FrzA, frizzled A, SARP-2, secreted apoptosis-related protein-2, FRP, frizzled-related protein | Rozsa et al, 2006; Zhao X et al, 2004 |
| sFRP2 | secreted frizzled-related protein 2, FRP2, frizzled-related protein 2, SARP-1, secreted apoptosis-related protein-1, SDF-5, stromal cell derived factor-5 | Fan et al, 2008 |
| SLPI | secretory leukocyte protease inhibitor, antileukoproteinase, ALP, BLPI, Bronchial leukocyte proteinase inhibitor, BMI bronchial mucus inhibitor, CUSI, cervical mucus inhibitor, HUSI-1, human seminal plasma inhibitorl, MPI, Mucus proteinase inhibitor, seminal plasma inhibitor | Rozsa et al, 2006 |
| S MAD 1 | Snia and Mad related protein-1, Mad, Mothers against decapentaplegic. Sma, MADH1, Mothers against decapentaplegic homolog 1, Mothers against DPP homolog 1, MADR1, Mad-related protein 1, BSPI, TGF-beta signaling protein-1, .IV41- | Rozsa et al, 2006 |
| SMAII7 | Sma and Mad related protein-7, MADH7, Mothers against DPP homolog 7, Mothers against DPP homolog 7, CRCS3, colorectal cancer susceptibility 3 | Fuchshofer et al, 2009 |
| SOCS5- | Suppressor of cytokine signaling-5, CIS6, Cytokine inducible 5H2-containing protein-6 | Rozsa et al. 2006 |

| Protein Name | Alternative Names | Reference |
|---|---|---|
| SOCSS | Suppressor of cytokine signaling-6, CIS4, Cytokiє te inducible 5I-T2-containing protein-4 | Rozsa et al, 2006 |
| SPARC | secreted protein acidic and rich in cysteine, osteonectin, }3 M-40, 43IC glycoprotein | Rhee et al, 2003; Rozsa et al, 2006; Vittal et al, 2005 |
| sprouty-1 | Spry-1 | Fan et al, 2008 |
| sprouty-4 | Spry-4 | Rozsa et al, 2006 |
| stanniocalcin 2 | STC2, STCRP, stanniocalcin-related protein | Fan et al, 2008 |
| STA'1'I | signal transducer and activator of transcription-1, STAT1-alpha, STAT1-beta, p91, 5tat91, p84 | Rozsa et al, 2006 |
| 5ᵤM01 | small ubiquitin-related modifier-1, Sentrin, Sentrin-1, UBI, 1, ubiquitin-like-1, PIC1, PML interacting clone-i, SMT3H3, SMT homolog 3, GMP1, GAP-modifying protein 1, SMT3C | Fan et al, 2008 |
| Syndecan-L | CD138, syndecan, 5DC1, Synd1, SD-I, 104-9 antigen, 1D4antigen, B-B2 antigen, $-B4 antigen, Mi15 | Luna et al, 2009 |
| TFT'T-2 | tissue factor pathway inhibitor-2, MSPI, matrix-associated serine protease inhibitor | Fuchshofer et al 2009 |
| TGF-alpha receptor | transforming growth factor-alpha, TGFA, TGF-A, MDGF-2, milk-derived growth factor-2, TCGF, transformed cell growth factor, wa-I, waved-i receptors | Wordinger et al, 1998 |
| TGF-beta | transforming growth factor-beta, TGFB, B-TGF, Aqueous humor lymphocyte inhibitory activity, IDIF, differentiation-inhibiting factor, EGI, epithelial cell-specific growth inhibitor; epithelial growth inhibitor, EIF, Epstein-Barr virus inducing factor, Epithelial cell growth inhibiting factor, G-TsF, g(iorna-derived "l'-cell suppressor factor, MDGF, milk-derived growth factor, MGF, milk growth factor, Polyergin, Simian BSC-1 cell growth inhibitor, SP factor, TCGF, transformed cell growth factor, TG1, tissue-derived growth inhibitor, TIF-1, tumor inducing factor-1 | Fatma et al, 2009 |

TABLE A-continued

| | | |
|---|---|---|
| TGF-beta-1 | transforming growth factor-beta-1, CIF-A, cartilage inducing factor A, 1SF, immunosuppressive factor, MGF-b, milk growth factor, PDGI, platelet-derived endothelial cell growth inhibitor | Liton et al, 2009; Li 1 et, 1996 |
| TGF-beta-1 receptor | transforming growth factor-beta-1, CIF-A, cartilage inducing factor A, ISF, immunosuppressive factor, MGF-b, milk growth factor, PDGI, platelet-derived endothelial cell growth inhibitor receptors | Liton et al, 2009; Li J et, 1996; Nakamura et al, 2002; Zhao X et al, 2004 |
| TGF-beta-2 | transforming growth factor-beta-2, TGFB2, G-TsF, Glioblastoma-derived T-cell suppressor factor, CIF-13, cartilage inducing factor S, Corneal epithelial inhibitor of stromal cell collagenase synthesis, DSF, decidual suppressor factor, MGF-a, milk growth factor. | Rozsa et al, 2006; Cao Y et al, 2004 |
| TGF-beta-2 receptor | transforming growth factor-beta-2, TGFB2, G-TsF, Glioblastoma-derived T-cell suppressor factor, CiF-8, cartilage inducing factor B, Corneal epithelial inhibitor of stromal cell coflagenase synthesis, DSF, decidual suppressor factor, MGF-a, milk growth factor receptors | Fuchshofer et al, 2009; Da et al, 2004; Fuchshofer et al, 2006, 2007; Li J et, 1996; Zhao X et al, 2004; Junglas et al, 2009; Keller et al, 2009 |
| TGF-beta-3 | transforming growth factor-beta-3, TGPβ3 | Luna et al, 2009; Rozsa et al, 2006 |

| Protein Name | Alternative Names | Reference |
|---|---|---|
| TGF-beta receptor | transforming growth factor-beta, TGFB, B-TGF, Aqueous humor lymphocyte inhibitory activity, DIF, differentiation-inhibiting factor, EGI, epithelial cell-specific growth inhibitor; epithelial growth inhibitor, EIF, Epstein-Barr virus inducing factor, Epithelial cell growth inhibiting factor, G-'I°sF, glioma-derived 'i'-cell suppressor factor, MIIGF, milk-derived growth factor, MGF, milk growth factor, Polyergin, simian BSC-1 cell growth inhibitor, SP factor, TCGF, transformed cell growth factor, TG1, tissue-derived growth inhibitor, TIF-1, tumor inducing factor-1 receptors | Alexander et al, 1998; Usui et al, 2003; Wordinger et al, 1998; Rozsa et al, 2006 |
| Thrombospondin-1 | Thrombospondin, TSP1, TSP, THBS1 | Fatma et al, 2009; Zhao X et al, 2004; Fuchshofer et al, 2007 |
| thrombospondin-2 | TSP2, THBS2 | Fan et al, 2008; Rozsa et al, 2006 |
| thymopoietin | Tpo, 'TP, TMPO, TP-5, thymopentin, thyrnopoietin 32-36, Lamina-associated polypeptide 2, LAP2 | Zhao X et al, 2004 |
| thyroid hormone receptors | | Duncan et al, 1999 |
| TIEG-I | TGF-beta-inducible early-response gene-1, KLF10, Krtippel-like factor 10, early growth response alpha, EGR-alpha | Luna et al, 2009 |
| TIMP-1 | tissue inhibitor of inetalloproteinases-[, TIMP metallopeptidase inhibitor 1, TIMP, tissue inhibitor of inetalloproteinases, HCI, human collagenase inhibitor, CLGI, 3/10, 16C8, Fibroblast elongation factor, fibroblast collagenase inhibitor, B 1 anticollagenase, Beta-1 anticoilagenase, BPA, erythroicl promoting activity, embryogenin-1, TPA-SI, TPA-induced protein 81 • | Sanka et al, 2007; Alexander et al, 1998; Conley et al, 2004; Fautsch et al, 2005; 7in and Wu, 2002; Oh et al, 2006; Pang et al, 2003; WuDunn, 2001 |
| TIMP-2 | tissue inhibitor of inetalloproteiπases-2, TIMP metallopeptidase inhibitor 2, CSC-21K, MI, CHIAMP, Chondrocyte-derived inhibitor of angiogenesis and metalloproteinase activity | Luna et al, 2009; Sanka et al, 2007; Alexander et al, 1998; 7in and Wu, 2002; Oh et al, 2006; Rozsa et al, 2006; , 2001 |
| TIMP-3 | tissue inhibitor of rraetalloproteinases-3, TIM? Metallopeptidase inhibitor 3, mitogen-inducible gene 5, mig-5; SFD, Sarsby fundus dystrophy | 7in and Wu, 2002; Oh et al, 2006 |
| TIMP-4 | tissue inhibitor of inetalloproteinases-4, TIM? Metallopeptidase inhibitor 4 | Oh et al, 2006 |
| Tissue factor | TF, TFA, thromboplastin, tissue thromboplastin, CD142, factor III, factor 3, F3, FIII, coagulation factor III | Rozsa et al, 2006 |
| TNFAIPI | tumor necrosis factor-alpha-induced protein 1, TNF-alpha-induced protein 1, TNFAIP, tumor necrosis factor-alpha-induced protein, TN1-alpha-induced protein, B 12, EDP1, endothelial TNF-alpha-induced protein I | Rozsa et al 2006 |

TABLE A-continued

| | | |
|---|---|---|
| TNFAIP2 | tumor necrosis factor-alpha-induced protein 2, TNF-alpha-induced protein 2, B94 | Vittal et al, 2005 |
| TNFAIP8 | tumor necrosis factor-alpha-induced protein 8, TNF-alpha-induced protein 8, NDED, NF-kappa-B-inducible DED-containing protein, 002-1, SCC-S2 | Rozsa et al, 2006 |

| Protein Name | Alternative Names | Reference |
|---|---|---|
| TNF-alpha Receptor | tumor necrosis factor-alpha, TNFSF2, TNF ligand superfamily member 2, Cachectin, CF, cytotoxic factor, CTX, cytotoxin, DIF, differentiation inducing factor, E?, endogenous pyrogens, Hemorrhagic factor, Macrophage-derived cytotoxic factor, 7774-derived cytotoxic factor, MCF, macrophage cytotoxic factor, MCT, macrophage cytotoxin, MD-FGF, monocyte-derived fibroblast growth factor, PCF, peritoneal cytotoxic factor, RCF, Released cytotoxic factor receptors | Kelley et al, 2007; Alexander et al, 1998; Wordinger et al, 1998; Pang et al, 2003; Keller et al, 2009 |
| TNF-beta receptor | tumor necrosis factor-beta, TNFB, Coleys toxin, LT, lymphotoxin, lymphotoxin-alpha, LT-alpha, LTA, Necrosin, NKCF, natural killer cytotoxic factor, NK-CIA, Natural killer colony-inhibiting activity, TNFSF1, TNF' ligand superfamily member 1 receptors | Alexander et al, 1998 |
| tPA | tissue plasminogen activator, tissue-type plasminogen activator, PLA.'1', plasminogen activator, tissue | Lana et al, 2009; Rozsa et al, 2006; 5hИTaП et al, 1988 |
| TRAF1 | Tumor necrosis factor receptor-associated factor-1, EBI-6, EBV induced gene-6 | Rozsa et al, 2006 |
| TRAIL | TNF-related apoptosis inducing ligand, APO-2 ligand, APO-2L, TL2, TNF-like-2, TNF ligand superfamily member 10, TNF5F10, Ly81, CD253 | Luna et al, 2009; Rozsa et al, 2006; Zhao X et al, 2003 |
| TRAIL receptor-4 | (TRAIL receptor-4, TRAIL-R4, DcR-2, Decoy receptor-2, TRUNDD, TRAIL receptor with a truncated death domain, TNFRSF10D, TNF receptor superfamily member 10D, CD264) (receptor for TNF-related apoptosis inducing ligand, APO-2 ligand, APO-2L, TL2, TNF-lilce-2, TNF ligand superЄamily member 10, TNFSF10, Ly81, CD253) | Zhao X et al, 2004 |
| transferrin | TRF, serotransferrin, siderophilin, DF-77, GPBP, granulocyte/pollen-biПding protein, Lung-derived growth factor receptors | Rozsa et al, 2006 |
| trkA | tropomyo sin-related kinase A, NTRK1, neurotrophic tyrosine kinase receptor 1 | Wordinger et al, 2000 |
| trkB | tropomyosin-related kinase B, NTRK2, neurotrophic tyrosine kinase receptor 2 truncated | Wordinger et al, 2000 |
| trkC | tropomyosin-related kinase C, NTRK3, neurotrophic tyrosine kinase receptor 3 | Wordinger et al, 2000 |
| Tryptophanyl-tRNA synthetase | TrpRS, WARS, Tryptophan-tRNA Ligase | Ishibashi et al, 2002; Leung YF et al, 2003 |
| TSC-22 | TGF-beta-stitnulated cloПe-22, TSC22D1, TSC22 domain family member 1 | Leung YF et al, 2003 |
| TSG-6 | tumor necrosis factor-stimulated sequeПce-6, TNFAIP6, tumor necrosis factor-alpha-induced protein 6, TNFIP6, tumor necrosis factor-induced protein 6, PS4 | Luna et al, 2009; Fuchshofer et al, 2009; Rozsa et al, 2006; Zhao X et al, 2004 |
| TST..,P | thymic stromal derived lymphopoietin, Thymic stromal lymphopoietin | Luna et al, 2009 |

| Protein Name | Alternative Names | Reference |
|---|---|---|
| VEGF | vascular endothelial growth factor, VEGF-A, vascular endothelial growth factor A, VEGF-1, vascular endothelial growth factor-1., VEG/PF, vascular endothelial growth factor/vascular permeability factor, C'iD-VEGF, glioma-derived vascular endothelial growth factor, VAS, Vasculotropin, Vascular endothelial cell proliferation factor, VPF, vascular permeability factor, FSdGF, Folliculo stellate cell-derived growth factor | Fuchshofer et al, 2009; Rozsa et al, 2006 |
| VEGF Receptor | vascular endotheiial growth factor, VEGF-A, vascular endothelial growth factor A, VEGF-1, vascular endothelial growth factor-I, VFG/PF, vascular endothelial growth factor/vascular permeability factor, C'iD-VEGF, glioma-derived vascular endothelial growth factor, VAS, Vasculotropin, Vascular endothelial cell proliferation factor, VPF, vascular permeability factor, FSdGF, Folliculo stellate cell-derived growth factor receptors | Alexander et al, 1998; Ando et al, 2004 |

TABLE A-continued

| | | |
|---|---|---|
| VEGF-C | vascular endothelial growth factor C, VEGF-2, Vascular endothelial growth factor-2, flt-4 ligand, flt-4L | Luna et al, 2009; Rozsa et al. 2006 |
| WIIt-2b | Wnt-13, Wnt-2b1, Wnt-2b2 | Rozsa et al, 2006 |
| Wnt-5a | | Rozsa et al, 2006 |

Abad E et al., Investigative Ophthalmology and Visual Science 49(2): 677-686 (2008);
Agarwai R et al., Experimental Eye Research 68(5): 583-590 (1999);
Alexander J P et al Cunerit Eye Research 17(3): 276-285 (1998);
Ando A et aL, Nippon Ganka Gakkai Zasshi 108(9): 549-553 (2004);
Borras T et al., Experimental Eye Research 82(6): 1002-1010 (2006);
Caithorpe C M and Grierson I, Experimental Eye Research 51(1): 39-48 (1990);

Cao Y et al., Zhonghua Yan K e Za Zhi 40(4): 254-257 (2004);
Cao Y et al., Journal of Huazhong University of Science and Technology Medical Sciences 24(1): 87-9, 94 (2004);
Cao Y et al., Journal of Huazhong University of Science and Technology Medical Sciences 22(1): 69-72 (2002);
Chang A T et al., Current Eye Research 15(2): 137-143 (1996);
Clark A F et al., investigative Ophthalmology and Visual Science 42(8): 1769-1780 (2001);
CoII ley S M et al., Investigative Ophthalmology and Visual Science 45(2): 473-479 (2004);
Coupland S E et al., Graefes Archive of Clinical and Experimental Ophthalmology 231(9): 533-540 (1993);
Da B et al., Journal of Huazhong University of Science and Technology Medical Sciences 24(5): 490-492, 496 (2004);

Dai W and Li M, Zhonghua Yan K e Za Zhi 33(6): 413-416 (1997);
Dickerson J E et al., Experimental Eye Research 66(6): 731-738 (1998);
Duncan K G et al., Graefes Archive of Clinical and Experimental Ophthalmology 237(3): 231-240 (1999);
Fan B J et al., Investigative Ophthalmology and Visual Science 49(5): 1886-1897 (2008);
Fatma N et al., Free Radicals Research 43(9): 783-795 (2009);
Fautsch M P et al., Investigative Ophthalmology and Visual Science 46(8): 2848-2856 (2005);
Filla M S et al., Investigative Ophthalmology and Visual Science 47(5): 1956-1967 (2006);
Fleenor D L et aL, Investigative Ophthalmology and Visual Science 2003 Aug; 44(8): 3494-3501 (2003);
Fuchshofer R et al., investigative Ophthalmology and Visual Science 47(3): 794-801 (2006);
Fuchshofer R et al., Investigative Ophthalmology and Visual Science 48(2): 715-726 (2007);
Fuchshofer R et al., Experimental Eye Research 88(6): 1020-1032 (2009);
Fukuchi T et al., Nippon Ganka Gakkai Zasshi 101(3): 265-271 (1997);
Gasiorowski J Z and Russell P, Experimental Eye Research 88(4): 671-675 (2009);
Hague M S et al,. Current Eye Research 17(12): 1110-1117 (1998);

Hardy K M et al., Journal of Biological Chemistry 280(32): 28917-28926 (2005);
He X and Li M, Zhonghua Yan K e Za Zhi 37(1): 50-52 (2001);
He X and Li M, Zhonghua Yan K e Za Zhi 33(6): 406-409 (1997);
Hoffman E A et al., Investigative Ophthalmology and Visual Science 50(3): 1313-1318 (2009);
Howard G C et al., Archives of Biochemistry and Biophysics 333(1): 19-26 (1996);
Husain S et aL, Journal of Pharmacology and Experimental Therapeutics 320(1): 258-265 (2007);
Ishibashi T et aL, investigative Ophthalmology and Visual Science 43(12): 3691-3697 (2002);

Jin M and Wu J, Zhonghua Yan K e Za Zhi 38(5): 298-301 (2002);
Jurnper M D et al, Ophthalmic Research 30(5): 314-320 (1998);
Junglas B et al., Experimental Eye Research 88(6): 1065-1075 (2009);
Kageyama M et al, Journal of Ocular Pharmacology and Therapeutics 12(4): 433-440 (1996);

Kashiwagi K et al., Journal of Glaucoma 10(4): 271-276 (2001);

Keller K E et al., Investigative Ophthalmology and Visual Science 48(3): 1164-1172 (2007);

Keller K et al., Investigative Ophthalmology and Visual Science #### (2009);
Kelley M J et al., Investigative Ophthalmology and Visual Science 48(7): 3126-3137 (2007);
Kim J W, Korean Journal of Ophthalmology 21(1): 39-44 (2007);
Kirstein L et al., Genes Cells 5(8): 661-676 (2000);
Kohmoto H et aL, Current Eye Research 13(3): 197-202 (1994);
Leung Y F et aL, Molecular Vision 9: 425-439 (2003);
Li G et aL, Molecular Vision 13: 2282-2288 (2007);
Li J et al., Investigative Ophthalmology and Visual Science 37(13): 2778-2782 (1996);

Li X Y et aL, Zhonghua Yan K e Za Zhi 42(11): 977-979 (2006);
Li Z and Zhang H, Journal of Huazhong University of Science and Technology Medical Sciences 24(5): 486-489 (2004);
Lin S et al., Current Eye Research 32(1): 43-50 (2007);
Liton P B et aL, Molecular Vision 15: 326-334 (2009);
Liu X et aL, Experimental Eye Research 72(6): 711-717 (2001);
Llobet A et al., Investigative Ophthalmology and Visual Science 40(1): 113-125 (1999);
Luna C et al., Food Chemistry and Toxicology 47(1): 198-204 (2009);
Luna C et aL, Molecular Vision 15: 534-544 (2009);
Ltitjen-Drecoll E Functional morphology of the trabecular meshwork in primate eyes. Progress in Retinal and Eye Research 18(1): 91-119 (1999);
Matsumoto Y and Johnson D H Trabecular meshwork phagocytosis in glaucomatous eyes. Ophthalmologica 211(3): 147-152 (1997);
Michael I et al., Investigative Ophthalmology and Visual Science 49(9): 3981-3987 (2008);
Miller A M et al Lactate treatment causes NF-kappaB activation and CD44 shedding in cultured trabecular meshwork cells. Investigative Ophthalmology and Visual Science 48(4):1615-1621 (2007);

Milton K P et al., Biochemical Biophysical Research Communications 235(1): 69-73 (1997);
Miyamoto N et al Nipradilol and timolol induce Foxo3a and peroxiredoxin 2 expression and protect trabecular meshwork cells from oxidative stress. Investigative Ophthalmology and Visual Science 50(6): 2777-2784 (2009);
Nakamura Y et al Signaling mechanism of TGF-beta1-induced collagen contraction mediated by bovine trabecular meshwork cells. Investigative Ophthalmology and Visual Science 43(11): 3465-3472 (2002);
Nguyen T D et al Gene structure and properties of TIGR, an olfactarnedin-related glycoprotein cloned from glucocorticoid-induced trabecular meshwork cells. Journal of Biological Chemistry 273(11): 6341-6350 (1998);
Obazawa M et al Analysis of porcine optineurin and myocilin expression in trabecular meshwork cells and astrocytes from optic nerve head. Investigative Ophthalmology and Visual Science 45(8): 2652-2659 (2004);
Oh D J et al Effect of latanoprost on the expression of matrix metalloproteinases and their tissue inhibitors in human trabecular meshwork cells. Investigative Ophthalmology and Visual Science 47(9): 3887-3895 (2006);
Pang iH et al Expression of matrix metalloproteinases and their inhibitors in human trabecular meshwork cells. Investigative Ophthalmology and Visual Science 44(8): 3485-3493 (2003);

TABLE A-continued

Peterson J A et al Heparin II domain of fibronectin uses alpha4beta1 integrin to control focal adhesion and stress fiber formation, independent of syndecan-4. Journal of Biological Chemistry 280(8): 6915-6922 (2005);
Pfeffer B A et al A selective glucocorticoid receptor agonist (SEGRA) induces decreased myocilin protein and gene expression in cultured monkey trabecular meshwork cells when compared to traditional ocular steroids. Investigative Ophthalmology and Visual Science#### (2009);
Polansky J R et al Regulation of TiGR/MYOC gene expression in human trabecular meshwork cells. Eye 14(Pt 3 B): 503-514 (2000);
Rhee D J et al The matricellular protein SPARC is expressed in human trabecular meshwork. Experimental Eye Research 77(5): 601-607 (2003);
Rosenthal R et al Effects of ML-7 and Y-27632 on carbachol-and endothelin-l-induced contraction of bovine trabecular meshwork. Experimental Eye Research 80(6): 837-845(2005);
Rozsa F W et aL, Molecular Vision 12: 125-141 (2006);
Sakai H et at, Journal of Cellular Physiology 213(3): 775-784 (2007);

Sanka K et aL, Investigative Ophthalmology and Visual Science 48(5): 2105-2114 (2007);
Sato T and Roy S, Investigative Ophthalmology and Visual Science 43(1): 170-175 (2002);
Savaskan E et aL, Ophthalmic Research 36(6): 3 12-320 (2004);
Sawaguchi S et aL, Investigative Ophthalmology and Visual Science 35(1): 251-261 (1994);
Schlunck G et aL, Investigative Ophthalmology and Visual Science 49(1): 262-269 (2008);
Sharif N A and Xu S X., Experimental Eye Research 63(6): 631-637 (1996);
Shearer T and Crosson C E, Experimental Eye Research 73(1): 25-35 (2001);
Shearer T W and Crosson C E, Investigative Ophthalmology and Visual Science 43(9): 3016-3020 (2002);

Shen F et at, [Yan K e Xue Bao 17(4): 209-212 (2001);
Sherwood M E and Richardson T M, Experimental Eye Research 1988 Jun; 46(6): 881-895(1988);
Shuman M A et al., Investigative Ophthalmology and Visual Science 29(3): 401-405 (1988);
Sohn S et al., Investigative Ophthalmology and Visual Science 43(12): 3680-3685 (2002);
Steely H T et aL, Investigative Ophthalmology and Visual Science 33(7): 2242-2250 (1992);
Takahashi H et at, Current Eye Research 20(2): 81-84 (2000);
Takahashi H et al., Biochemical Biophysical Research Communications 248(1): 104-109 (1998);
Taniguchi F et al., Investigative Ophthalmology and Visual Science 41(8): 2070-2075 (2000);
Tao W et al., Current Eye Research 17(1): 31-38 (1998);
Thieme H et aL, Ophthalmic Research 37(6): 293-300 (2005);
Tiwari V et al., Journal of Virology 79(20): 13173-13179 (2005);
Tripathi R C et at, Experimental Eye Research 64(3): 335-341 (1997);
Ueda J et al., Journal of Histochemistry and Cytochemistry 48(10): 1321-1330 (2000);
Usui T et al., British Journal of Ophthalmology 87(3): 357-360 (2003);
Vittal V et al, Investigative Ophthalmology and Visual Science 46(8): 2857-2868 (2005);
Webb J G et al., Experimental Eye Research 76(3): 283-289 (2003);
Webb J G et al., Journal ofd Ocular Pharmacology and Therapeutics 22(5): 310-316 (2006);
Webb J G et al, Experimental Eye Research 89(2): 126-132 (2009);

Wentz-Hunter K et al., Journal of Cellular Physiology 200(1): 45-52 (2004);

Wentz-Hunter K et al., Journal of Cellular Physiology 190(1): 46-53 (2002);
Wordinger R J et aL, Investigative Ophthalmology and Visual Science 39(9): 1575-1589 (1998);
Wordinger R J et al., Investigative Ophthalmology and Visual Science 41(12): 3833-3841 (2000);
Worthen D M and Cleveland P H., Investigative Ophthalmology and Visual Science 23(2): 265-269 (1982);
WuDunn D, Experimental Eye Research 88(4): 718-723 (2009);
WuDunn D, Current Eye Research 22(5): 394-397 (2001);
Xue W et aL, Investigative Ophthalmology and Visual Science 47(3): 997-1007 (2006);
Yu AL et aL, Investigative Ophthalmology and Visual Science 49(11): 4872-4880 (2008);
Yue BY et aL, Experimental Cell Research 187(1): 65-68 (1990);
Zhang X et ai., Experimental Eye Research 82(6): 968-973 (2006);
Zhang X et al., Investigative Ophthalmology and Visual Science 44(12): 5301-5308 (2003);
Zhao X et al., Investigative Ophthalmology and Visual Science 44(5): 1945-1952 (2003);
Zhao X et aL, Investigative Ophthalmology and Visual Science 45(11): 4023-4034 (2004);
Zhong L et al., Journal of Ocular Pharmacology and Therapeutics 19(5): 425-436 (2003);
Zhou L et al., Investigative Ophthalmology and Visual Science 37(1): 104-113 (1996);
Zhou L et aL, In Vitro Cellular and Developmental Biology Animals 35(3): 144-149 (1999);
Zhou L et aL, Current Eye Research 17(2): 211-217 (1998);
Zhou L et al., Current Eye Research 19(5): 395-402 (1999);

Zhou Q et al., Zhongguo Yi Xue K e Xue Yuan Xue Bao 29(3): 394-397 (2007);

The following represents a listing of the references cited in Example 2:

1. Stamer W D, Seftor R E, Snyder R W, et al. Cultured human trabecular meshwork cells express aquaporin-I water channels. Current eye research. 1995; 14:1095-1100.
2. Alvarado J, Murphy C, Polansky J, et al. Age-related changes in trabecular meshwork cellularity. investigative ophthalmology & visual science. 1981; 21:714-727.
3. He Y, Leung K W, Zhang Y H, et al. Mitochondrial complex I defect induces ROS release and degeneration in trabecular meshwork cells of POAG patients: protection by antioxidants. Investigative ophthalmology & visual science. 2008; 49:1447-1458.
4. Verfaillie C M. Adult stem cells: assessing the case for pluripotency. Trends in cell biology. 2002; 12:502-508.
5. Beltrami A P, Barlucchi L, Torella D, et al. Adult cardiac stem cells are multipotent and support myocardial regeneration. Cell. 2003; 114:763-776.
6. Tropepe V, Coles B L, Chiasson B J, et al. Retinal stem cells in the adult mammalian eye. Science. 2000; 287: 2032-2036.
7. Coles B L, Angenieux B, Inoue T, et al. Facile isolation and the characterization of human retinal stem cells. Proc Natl Acad Sci USA. 2004; 101:15772-15777.
8. Arsenijevic Y, Villemure J G, Brunet J F, et al. Isolation of multipotent neural precursors residing in the cortex of the adult human brain. Exp Neurol. 2001; 170:48-62.
9. Oshima K, Senn P, Heller S. Isolation of sphere-forming stem cells from the mouse inner ear. Methods Mol Biol. 2009; 493:141-162.
10. Jiang Y, Jahagirdar B N, Reinhardt R L, et al. Pluripotency of mesenchymal stem cells derived from adult marrow. Nature. 2002; 41:41-49.
11. Goodell M A, Brose K, Paradis G, et al. Isolation and functional properties of rnurirxe hematopoietic stem cells that are replicating in vivo. J Exp Med. 1996; 183:1797-1806.

12. Gonzalez P, Epstein D L, Luna C, et al. Characterization of free-floating spheres from human trabecular meshwork (HTM) cell culture in vitro. Experimental eye research. 2006; 82:959-967.
13. McGowan S L, Edelhauser H F, Pfister R R, et al. Stem cell markers in the human posterior limbus and corneal endothelium of unwounded and wounded corneas. Molecular vision. 2007; 13:1984-2000.
14. Zhang X, Ognibene C M, Clark A F, et al. Dexamethasone inhibition of trabecular meshwork cell phagocytosis and its modulation by glucocorticoid receptor beta. Experimental eye research. 2007; 84:275-284.
15. Du Y, Funderburgh M L, Mann M M, et al. Multipotent stem cells in human corneal stroma. Stem cells (Dayton, Ohio). 2005; 23:1266-1275.
16. Du Y, Carlson E C, Funderburgh M L, Birk D E, Pearlman F, Guo N, Kao W W Y, Funderburgh J L. Stem Cell Therapy Restores Transparency to Defective Murine Corneas. Stem Cells. 2009.
17. McKenna K C, Xu Y, Kapp J A. Injection of soluble antigen into the anterior chamber of the eye induces expansion and functional unresponsiveness of antigen-specific CD8-h T cells. J Immunol. 2002; 169:5630-5637.
18. Sarkadi B, Orban Ti, Szakacs G, et al. Evaluation of ABCG2 expression in human embryonic stem cells: crossing the same river twice? Stem cells (Dayton, Ohio). 28:174-176.
19. Zhou S, Schuetz J D, Bunting K D, et a). The ABC transporter Bcrp1IABCG2 is expressed in a wide variety of stem cells and is a molecular determinant of the side-population phenotype. Nature medicine. 2001; 7:1028-1034.
20. Martin C M, Meeson A P, Robertson S M, et al. Persistent expression of the ATP-binding cassette transporter, Abcg2, identifies cardiac SP cells in the developing and adult heart. Developmental biology. 2004; 265:262-275.
21. Yin L, Castagnino P, Assoian R K. ABCG2 expression and side population abundance regulated by a transforming growth factor beta-directed epithclial-mesenchyrnal transition. Cancer research. 2008; 68:800-807.
22. Yoshida S, Shimmura S, Nagoshi N, et al. Isolation of multipotent neural crest derived stem cells from the adult mouse cornea. Stem cells (Dayton, Ohio). 2006; 24:27 14-2722.
23. Sivak J M, Mohan R, Rinehart W B, et al. Pax-6 expression and activity are induced in the reepithelializing cornea and control activity of the transcriptional promoter for matrix metalloproteinase gelatinase B. Developmental biology. 2000; 222:41-54.
24. Akinci M A, Turner H, Taveras M, et al. Molecular profiling of conjunctival epithelial side-population stem cells: atypical cell surface markers and sources of a slow-cycling phenotype. investigative ophthalmology & visual science. 2009; 50:4162-4172.
25. P. Challa P G, P. B. Liton, et al. Gene expression profile in a novel cell type in primary cultures of human trabecular meshwork. Investigative ophthalmology & visual science. 2003; 44:E-Abstract 3164.
26. Kelley M J, Rose A Y, Keller K E, et al. Stem cells in the trabecular meshwork: present and future promises. Experimental eye research. 2009; 88:747-751.
27. Stamer W D, Snyder R W, Smith B L, et al. Localization of aquaporin CHIP in the human eye: implications in the pathogenesis of glaucoma and other disorders of ocular fluid balance. Investigative ophthalmology & visual science. 1994; 35:3867-3872.
28. Liton P B, Luna C, Challa P, et al. Genome-wide expression profile of human trabecular meshwork cultured cells, nonglaucomatous and primary open angle glaucoma tissue. Molecular vision. 2006; 12:774-790.
29, Vittitow 7, Borras T. Genes expressed in the human trabecular meshwork during pressure-induced homeostatic response. Journal of cellular physiology. 2004; 201:126-137.
30. Liton P B L Y, Luna C, et al. Identification of genes differentially expressed by Chitinase 3-like 1 in human trabecular meshwork cells. IOVS. 2009; 50:4859.
31. Alexander J P, Samples J R, Van Buskirk E M, et al. Expression of matrix metalloproteinases and inhibitor by human trabecular meshwork. Investigative ophthalmology & visual science. 1991; 32:172-180.
32. Zhou S, Morris J7, Barnes Y, et al. Berp1 gene expression is required for normal numbers of side population stem cells in mice, and confers relative protection to mitoxantrone in hematopoietic cells in vivo. Proceedings of the National Academy of Sciences of the United States of America. 2002; 99:12339-12344.
33. Scharenberg C W, Harkey M A, Torok-Storb B. The ABCG2 transporter is an efficient Hoechst. 33342 efflux pump and is preferentially expressed by immature human hematopoietic progenitors. Blood. 2002; 99:507-512.
34. Kim M, Turnquist H, Jackson J, et al. The multidrug resistance transporter ABCG2 (breast cancer resistance protein 1) effluxes Hoechst 33342 and is overexpressed in hetta.atopoietic stem cells. Clin Cancer Res. 2002; 8:22-28.
35, Telford W G, Bradford J, Godfrey W, et al. Side population analysis using a violet-excited cell-permeable DNA binding dye. Stem cells (Dayton, Ohio). 2007; 25:1029-1036.
36. Mathew G, Timm E A, Jr., Sotomayor P, et al. ABCG2-mediated DyeCycle Violet efflux defined side population in benign and malignant prostate. Cell cycle (Georgetown, Tex. 2009; 8:1053-1061.
37. Bill A. Editorial: The drainage of aqueous humor. Investigative ophthalmology. 1975; 14:1-3.
38. Johnson D H, Richardson T M, Epstein D L. Trabecular meshwork recovery after phagocytic challenge. Current eye research. 1989; 8:1121-1 130.
39. Du Y, Sundarraj N, Funderburgh M L, et al. Secretion and organization of a cornea-lice tissue in vitro by stem cells from human corneal stroma. Investigative ophthalmology & visual science. 2007; 48:5038-5045.
40. Jung S E, Sea K Y, Kim H, et al. Expression of MUC1 on corneal endothelium. of human. Cornea. 2002; 21:691-695.
41. Ding X W, Wu J H, Jiang C P. ABCG2: a potential marker of stem cells and novel target in stem cell and cancer therapy. Life sciences. 86:631-637.
42. Stone E M, Fingert J H, Alward W L, et al. Identification of a gene that causes primary open angle glaucoma. Science (New York, N.Y. 1997; 275:668-670.
43. Wang N, Chintala S K, Fini M E, et al. Activation of a tissue-specific stress response in the aqueous outflow pathway of the eye defines the glaucoma disease phenotype. Nature medicine. 2001; 7:304-309.

Example 3

Materials and Methods

Primary Cell Culture

De-identified human corneas were obtained from the Center for Organ Recovery & Education (Pittsburgh, Pa.). Donor human corneas including scleral rim and trabecular meshwork (TM) not usable for transplantation were used for experiments. Cells from three donors at ages of 23-, 41- and 55-year old were used in the experiments shown. For each cell population, every experiment was repeated at least once. After careful removal of the iris, a cut was made through the inner edge of Schwalbe's line and the TM tissue was peeled off. We processed TMSC as either explant culture or dissociated cell culture. For explant culture, the tissue was cut into pieces and put in a 25-cm$^2$ culture flask. Stem cell growth medium (SCGM) was added and the culture was left undisturbed for 10-14 days. For dissociated cell culture, the dissected TM tissue was digested in 0.3 mg/ml collagenase type-L (Sigma-Aldrich, St. Louis, Mo.) in Dulbecco's modified Eagle's medium (DMEM) at 37° C. for 20-22 hours. After digestion, the cells were filtered through a 70 μm mesh and washed twice with DMEM. Cells were seeded at 2×10$^4$ cells/cm$^2$ in SCGM. For both cultures, cells were passaged at 80-90% confluency by trypsinization and seeded at 2-5× 10$^3$ cells/cm$^2$ in SCGM or seeded for clonal expansion by limiting dilution at 30 cells in a 96-well plate (0.3 cells/well). On average, about 1-10 percent of the 96 wells had clones with small cells which were picked up for subcultivation at 2-3 weeks after seeding. Among them, about ⅓-½ could be continuously passaged up to 30-50 population doublings. At least 6 clones from 3 donors were used and repeated in this study. SCGM was modified from a corneal endothelial cell culture medium[16] containing OptiMEM-1 (Invitrogen) supplemented with 5% fetal bovine serum (FBS) (Hyclone), 10 mg/ml EGF (Upstate Biotechnologies), 100 μg/ml bovine pituitary extract (Biomedical Technologies), 20 μg/ml ascorbic acid, 200 μg/ml calcium chloride, 0.08% chondroitin sulfate (Sigma-Aldrich), 100 IU/ml penicillin, 100 μg/ml streptomycin and 50 μg/ml (Sigma-Aldrich). Primary TM cells were cultured in DMEM without FBS or any growth factors.

Isolation of Stem Cells by Side Population (SP) Cell Sorting.

SP cell sorting was carried out as previously described (17-19) using DyeCycle Violet (DCV) dye (Invitrogen) with minor modifications. After 2-3 passages, 5×10$^5$ to 2×10$^6$ trypsinized cells were incubated at 1×10$^6$ cells/ml in prewarmed DMEM with 2% FBS and 10 μM DCV for 100 minutes at 37° C. To inhibit DCV efflux, 1×10$^5$ to 5×10$^5$ cells were preincubated for 20 minutes with 25 μg/ml fumitremorgin C before DCV incubation. After staining, the cells were washed twice in Hanks' balanced salt solution (HBSS) with 2% FBS and stored on ice. Immediately before sorting, 2 μg/ml propidium iodide was added to identify nonviable cells. Cells were analyzed on FACSAria flow cytometer high-speed cell sorter (BD Biosciences, San Jose, Calif.), using 405-nm excitation. Cells showing reduced fluorescence at both blue (450 nm) and red (670 nm), designated SP cells, were collected. A small proportion of non-SP cells were collected separately as control. Dead cells stained with propidium iodide were omitted from the population. The sorted SP and non-SP cells were cultured and passaged without cloning for further studies.

Flow Cytometry

Clonal passaged TMSC were trypsinized and cell suspensions were passed through a 40-μm filter-cap tube to remove debris. Antibodies used are listed in Table 3. For cell surface marker staining, fluorescent conjugated antibodies (CD73-PE, CD90-Alexa 647, CD166-FITC) or appropriate isotype controls were incubated with cells on ice for 30 minutes followed by washed in 1% bovine serum albumin (BSA) in PBS once and resuspended in the same buffer for flow analysis using FACSAria flow cytometer (BD Biosciences). 2 μg/ml propidium iodide was added to identify nonviable cells. For unconjugated antibody staining (Bmi1, AQP1, CHI3L1), cells were fixed in 1% paraformaldehyde on ice for 30 minutes and permeabilized with 0.1% Triton X-100 for 10 minutes. Cells were blocked in 10% heat-inactivated goat serum and stained with primary antibodies followed by secondary antibodies, 30 minutes on ice each. After washing, cells were resuspended in 1% BSA for flow analysis.

Multipotential Differentiation of Clonal Isolated TMSC

Neural differentiation: Clonal TMSC were seeded onto 35 mm dishes coated with FNC 7 Coating Mix (AthenaES, Baltimore, Md.) at 1×10$^4$ cells/cm$^2$ in neural differentiation medium (NDM) containing Advanced D-MEM with 10 mg/ml EGF, 10 mg/ml FGF2, 1 μM all-trans retinoic acid (17). The medium was changed every 3 days and fresh 1 μM all-trans retinoic acid was added each time. The cells were cultured for 1-2 weeks for neural induction.

Adipogenic Differentiation

Adipocytes were induced as previously described(20) with minor modifications. TMSC were seeded onto 1% gelatin (Sigma-Aldrich) coated 35-mm dishes at 2×10$^4$ cells/cm$^2$ and cultured in adipogenic differentiation medium (ADM) for 7 days, switched to adipogenic maintenance medium (AMM) for 4 days, then cycled again through ADM (7 days) and AMM (4 days) before fixation for histology or lysis for RNA. ADM consists of DMEM with 10% FBS, 1 μM dexamethasone, 0.5 mM methylisobutylxanthine, 10 μg/ml recombinant human insulin, 200 μM indomethacin. AMM contains DMEM with 15% FBS, 10 μg/ml insulin for 4 days.

Corneal Keratocyte Differentiation

Keratocyte differentiation was carried out as previously described (19). In brief, 3×10$^5$ TMSC were collected in a conical-bottom 15-mL tube, centrifuged at 1500 rpm (400 g) for 5 minutes to form a pellet. The pellets were cultured in SCGM for 3 days and then changed into keratocyte differentiation medium (KDM) (Advanced D-MEM (Invitrogen) with 10 mg/mL fibroblast growth factor 2 and 0.5 mM ascorbic acid) which was changed every 3 days for up to 3 weeks. Pellets cultured in SCGM served as control.

TM Cell Differentiation

Bovine aqueous humor (AH) was collected from enucleated bovine eyes by inserting a 27-gauge needle through the corneal limbus. AH was pooled and centrifuged at 10,000 g for 1 hour at 4° C. followed by filtering through 0.22 μm (8) Steriflip Filter Units (50 ml) (Millipore, Billerica, Mass.). The AH was aliquoted and stored at −80° C. for later use. TM cell differentiation was induced by culturing TMSC 35-mm dishes in three different conditions: 50% AH in SCGM, 100% AH, or DMEM/F12 plus 10% FBS. The media were changed every 3 days for up to 10 days.

Phagocytosis Assay

Assessment of phagocytosis was performed following the procedures described by Zhang et al(21) with minor modifications. In brief, Alexa-488 conjugated *Staphylococcus aureus* bioparticles (from heat- or chemically killed *S. aureus*) were incubated with opsonizing reagent (purified rabbit IgG antibody) (Invitrogen) at 37° C. for 1 hour to enhance particle uptake. The cells were incubated with opsonized Alexa-488 conjugated *S. aureus* bioparticles at a ratio of 20 bioparticles per cell at 37° C. for 1 hour. After incubation, the cells were fixed with 4% paraformaldehyde solution for 15 minutes at room temperature (RT) and incubated with Alexa-546 goat-anti-rabbit IgG secondary antibody for 1 hour. The secondary antibody binds to the extracellular bioparticles opsonized with rabbit IgG, so the unphagocytosed bioparticles can be excluded when counting. Cell nuclei were labeled with 4',6-diamidino-2-phenylindole (DAPI, Invitrogen) at 1 µg/ml for 10 minutes. Cellular phagocytosis of bioparticles was visualized and imaged with an Olympus FluoView FV1000 confocal microscope. The number of phagocytosed bioparticles was quantified by counting the cells and total bioparticles ingested by these cells. At least ten individual views per condition were counted and averaged. The data were analyzed statistically by one-way ANOVA followed by the Tukey post-test to assess the significance of differences between all groups.

Quantitative Reverse Transcription-Polymerase Chain Reaction (qRT-PCR)

Cells were lysed with RLT buffer in the RNeasy mini kit (Qiagen, Valencia, Calif.) and RNAs were isolated following the manufacturer's instructions including treatment with DNAse I (Invitrogen) and concentration by ethanol precipitation. cDNAs were transcribed from the RNAs using SuperScript II reverse transcriptase (Invitrogen). qRTPCR of cDNAs was performed by direct dye binding (SYBR Green; Applied Biosystems) as previously described(17). Primers for SYBR assays were designed using online software (Primer 3) with the sequences shown in Table 4. Amplification of 18S rRNA was performed for each cDNA (in triplicate) for normalization of RNA content. A negative control lacking cDNA was also included in each assay. Relative mRNA abundance was calculated as the Ct for amplification of a gene-specific cDNA minus the average Ct for 18S expressed as a power of 2 ($2-\Delta\Delta Ct$). Three individual gene-specific values thus calculated were averaged to obtain mean±SD.

Histology

Cells cultured directly on 35-mm tissue culture dishes were rinsed briefly in PBS, fixed in 4% paraformaldehyde at RT for 15 minutes, rinsed in PBS, and stored at 4° C. in 50% glycerol and 50% PBS (v/v) until staining. Cells cultured as pellets were rinsed and fixed in 4% paraformaldehyde and embedded in optimal cutting temperature embedding compound (OCT, Tissue-Tek OCT, Electron Microscopy Sciences, Hatfield, Pa.) and cut into 8 µm sections, stored at −20° C. until staining. Nonspecific binding was blocked with 10% heat-inactivated goat serum. Sections were incubated overnight at 4° C. with primary antibodies (shown in Table 3). After three washes, anti-mouse Alexa-488 or -10 546, anti-rabbit Alexa-546 or -647 secondary antibodies and nuclear dye DAPI were added and incubated for 2 hours at RT. Samples were imaged using a confocal microscope (Olympus) with a 40× oil objective.

Oil Red O Stain for Adipogenic Differentiation

Oil red O (Sigma-Aldrich) was prepared at 0.5% in isopropanol, diluted to 0.3% in water and filtered before use. Cells were stained with oil red O for 20 minutes and rinsed with 60% isopropanol followed by hematoxylin stain for nuclei. Bright-field micrography was performed with a 40× objective.

Immunoblotting

Cells were lysed directly in 1×SDS sample buffer, heated at 95° C. for 5 minutes, and sonicated until solubilized. Protein concentration was determined by Bio-Rad DC Protein Assay (Bio-Rad, Hercules, Calif.) and then β-mercaptoethanol was added to a final concentration of 1% to the lysates and heated at 70° C. for 20 minutes. An equal amount of protein was loaded to precast 4-20% gradient (Bio-Rad) and electrophoresis was performed for 1 hour at 200V. Protein was transferred to PVDF membrane (Millipore) and blocked for 1 hour at RT in blocking buffer (1% gelatin in PBS). Membranes were incubated with primary antibodies diluted in blocking buffer with 0.1% Tween-20 followed by incubation with IRDye 680LT goat-anti-mouse, IRDye 800CW goat-anti-rabbit or IRDye donkey-anti-goat secondary antibodies for Odyssey Infrared Imaging System (LI-COR Biosciences, Lincoln, Nebr.). Fluorescent signal was visualized with LI-COR substrate followed by detection and capture of 16-bit images with an Odyssey Infrared Imager (LI-COR Biosciences).

Results

Side Population (SP) Cells Express Stem Cell Markers

We previously isolated SP cells from human corneal stroma using the DNA-binding dye Hoechst 33342 17, 22 which is excited by ultraviolet light. Here we employed DyeCycle Violet Dye which is excited by violet light rather than ultraviolet laser in order to isolate SP cells from TM tissue. Both dyes can be actively effluxed by ATP-binding cassette transporter proteins and will generate an SP cell population(18, 23). To confirm the dissected TM tissue was not contaminated with adjacent corneal stromal tissue, the expression of TM specific markers AnkG(15) and CHI3L1 (24); corneal stromal marker keratocan (KERA)(25); and AQP1, expressed in both keratocytes(26) and TM(27), were compared on the TM tissue and the adjacent stromal tissue by qRT-PCR. FIG. 8A shows unfractionated cells from TM contain a small but significant side population which was collected by fluorescence-activated cell sorting (FACS). The percentage of SP cells ranged from 0.1-1.5% of the total population across multiple sorts. The isolated SP and non-SP cells were further expanded in SCGM and at passage-eight, gene expression was analyzed by qRT-PCR (FIG. 8B). The expression of stem cell genes ABCG2, Notch1, MUC1 and AnkG of SP cells was approximately 1.5 to 2-fold higher than that of non-SP cells. The expression of TM genes AQP1, MGP and CHI3L1 was approximately 4-fold lower in SP cells compared to non-SP cells. SP cells had almost no MYOC or ELAM-1 expression. The differences between SP and non-SP cells are statistically significant (p<0.05). FIG. 8C confirms that the isolated TM tissue which generated the SP cells was TM and not cornea. The isolated TM expressed AnkG(12) AQP1 and CHI3L1 but not the corneal gene KERA. In contrast, corneal stroma expressed AQP1 and KERA, but not AnkG nor CHI3L1.

Clonal Cultured TMSC are Distinct from Primary TM Cells

TMSC isolated by clonal growth and expanded in SCGM were initially compared with unfractionated primary TM cells cultured in medium without FBS or any growth factors. Immunofluorescent staining shows clonal TMSC were positive for stem cell markers ABCG2, Notch1, OCT4, AnkG, MUC1; but not TM cell markers TIMP3, CHI3L1, AQP1, MGP or MYOC (FIGS. 9A-9E). In contrast, primary TM cells expressed these TM cell markers but not stem cell markers (FIGS. 9F-9J). qRT-PCR result (FIG. 9K) shows clonal TMSC, compared to primary TM cells, have significantly increased expression of stem cell genes (ABCG2, Notch1, MUC1, AnkG), decreased expression of TM genes (AQP1, MGP, CHI3L1), and decreased expression of MYOC. The differences of each transcript between the two groups are statistically significant (p<0.05).

Flow cytometry was used to assess the purity of clonal passaged TMSC. FIG. 10A-10F revealed passage-four TMSC enriched with stem cell markers CD73, CD90, CD166 and Bmi1 (>95%) and lowered in TM markers AQP1 and CHI3L1 (<10%). This experiment was repeated on passage-two and passage-six TMSC with similar results.

Passaged TMSC are Multipotent

Figures 11A, 11B, 11C, 11D:
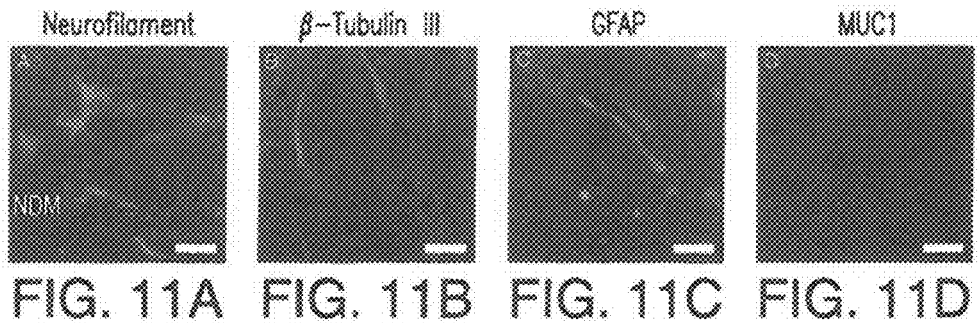
FIG. 11A-11I demonstrate induction of neural cell differentiation from TMSC. Immunofluorescent staining on neural markers neurofilament, β-tubulin III, GFAP and TMSC marker MUC1 shows different expression between TMSC in NDM FIG. 11A-11D(A-D) for neural induction and in SCGM (EH) to stem cell maintenance. DAPI stains nuclei blue. Bars=50 μm.
Figures 11E, 11F, 11G, 11H:
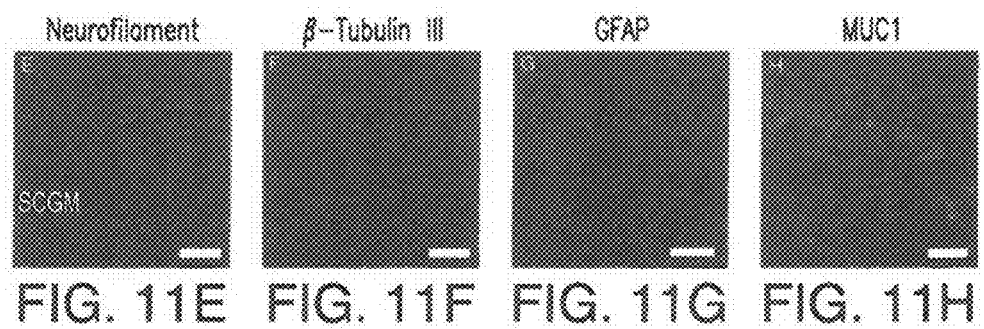
Figure 11I:
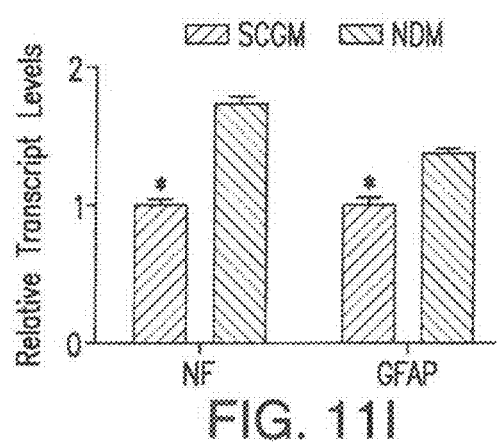

One of the characteristics of adult stem cells is multipotency, the ability to differentiate into a number of different cell types. We examined this property of the cloned TMSC by culturing them in different conditions. When TMSC were cultured in neural differentiation (13) medium containing EGF, FGF, and retinoic acid, expression of neurofilament protein, β-tubulin III and GFAP was observed (FIGS. 11A-11C), whereas MUC1 expression disappeared (FIG. 11D). In contrast, TMSC cultured in SCGM were MUC1 positive (FIG. 11H) without neural marker expression (FIGS. 11E-11G). Analysis of mRNA levels (FIG. 11I) confirmed significantly upregulated transcript of both neurofilament and GFAP after induction (p<0.05).

Under conditions inducing adipocytes, oil red O stained distinct intracellular lipid deposits in the induced TMSC (FIG. 12B) which were not present in TMSC cultured in SCGM (FIG. 12A). mRNA levels for adipocyte markers ap2 and Leptin were significantly increased (p<0.05) after induction in ADM/AMM compared to TMSC in SCGM (FIG. 12C).

Figure 13A:
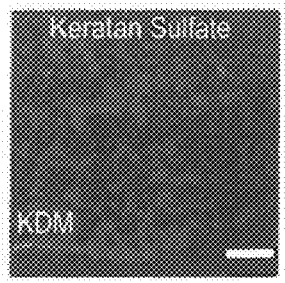
FIG. 13A-G demonstrate induction of corneal keratocyte differentiation from TMSC. Cryosections of TMSC cultured as pellets in KDM FIG. 13A-13B or in SCGM FIG. 13C-13D were stained with keratan sulfate FIG. 13A, 13C and keratocan FIG. 13B, 13D. Human corneal stromal stem cells cultured as pellets in KDM served as positive control were also stained with keratan sulfate FIG. 13E and keratocan FIG. 13F. DAPI stains nuclei blue. Bars=50 μm.
Figure 13B:
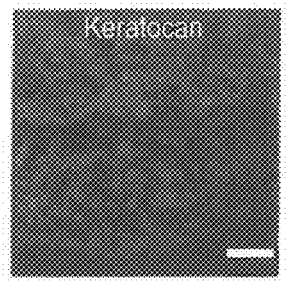
Figure 13C:
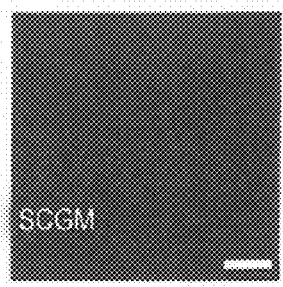
Figure 13D:
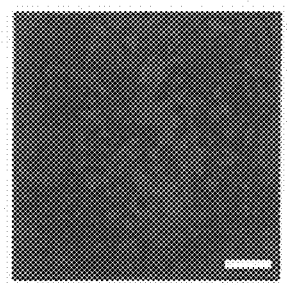
Figure 13E:
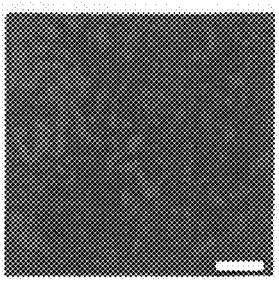
Figure 13F:
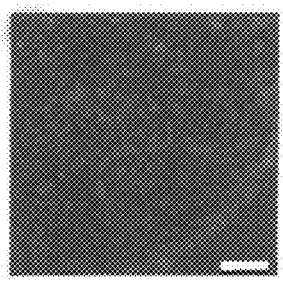
Figure 13G:
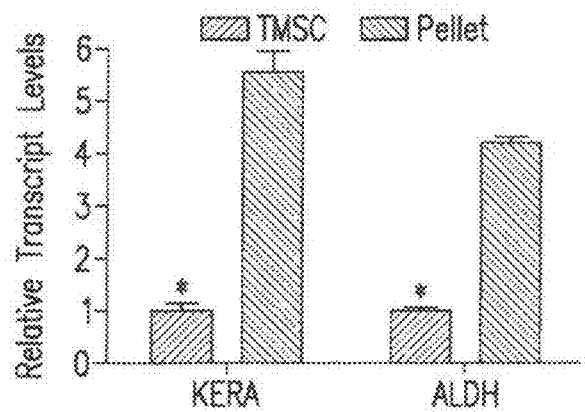

When TMSC were cultured as pellets in a medium shown to induce keratocyte phenotype(19), TMSC secreted corneal stromal specific extracellular matrix components keratan sulfate (FIG. 13A) and keratocan (FIG. 13B), similar to the pellets from human corneal stromal stem cells (FIGS. 13E-13F). When TMSC were cultured as pellets in SCGM, however, they formed fragile aggregates, little extracellular matrix, and did not stain for keratan sulfate and keratocan (FIGS. 13C-13D). FIG. 13G shows increased mRNA expression of keratocan (KERA) and ALDH after keratocyte induction. The upregulation is significant (p<0.05).

TMSC Differentiate into TM Cells with Phagocytic Function

TM cells function to maintain aqueous humor outflow and proper intraocular pressure with phagocytic activity and secretion of specific enzymes and extracellular matrix(4). TM cell number decreases with age and affects intraocular pressure(6-9). We examined if TMSC can differentiate into TM cells. Clonal TMSC were incubated in several media in order to induce TM cell differentiation: 50% bovine aqueous humor in SCGM (SCGM/AH), 100% bovine aqueous humor (AH), or DMEM/F12 containing 10% FBS.

Figure 15A:
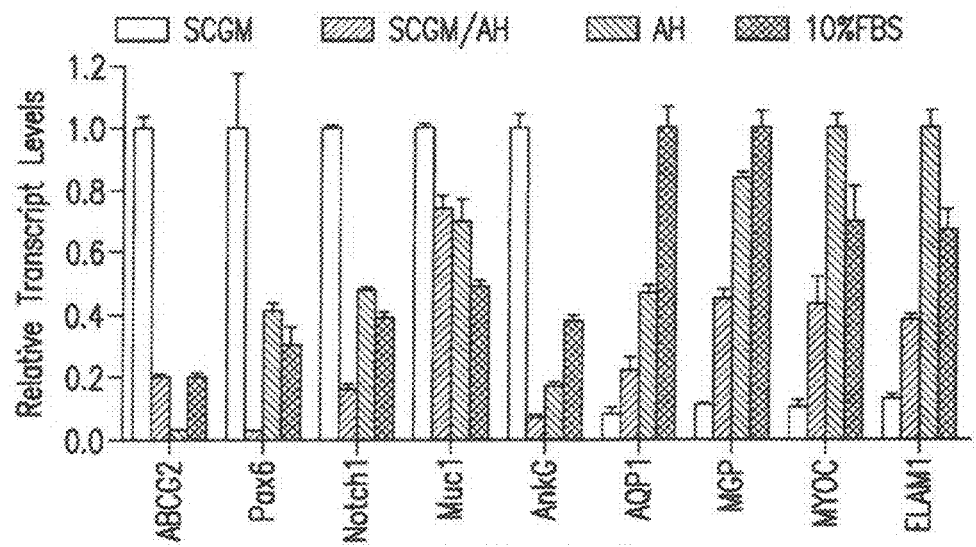
FIG. 15A-B demonstrate different gene expression of TMSC and induced TM cells by qRT-PCR and Western blotting.

The expression of stem cell- and TM cell-markers was compared by immunofluorescence, qRT-PCR and Western blotting. FIGS. 14A-14E show TMSC cultured in SCGM retained expression of stem cell markers ABCG2, Notch1, OCT4, AnkG, MUC1; but not TM differentiation markers TIMP3, CHI3L1, AQP1, MGP, and not MYOC. When cultured in SCGM/AH (FIGS. 14F-14J), in AH (FIGS. 14K-14O), or in 10% FBS (FIGS. 14P-14T), TMSC lost expression of stem cell markers but expressed the TM markers. Some induced TM cells were found to become MYOC positive (FIG. 14T, red).

qRT-PCR (FIG. 15A) revealed expression of ABCG2, Pax6, Notch1, MUC1, and AnkG to be decreased while expression of AQP1 and MGP increased upon TMSC differentiation in SCGM/AH, AH or 10% FBS. The expression of MYOC and ELAM-1 also increased after induction. Expression differences of all genes between TMSC in SCGM and induced cells in AH or in 10% FBS were statistically significant (p<0.05, oneway ANOVA followed by Dunnett's post-test). The differences between cells in SCGM and SCGM/AH were not consistently statistically significant. There were no statistical differences between cells in AH and 10% FBS.

Figure 15B:
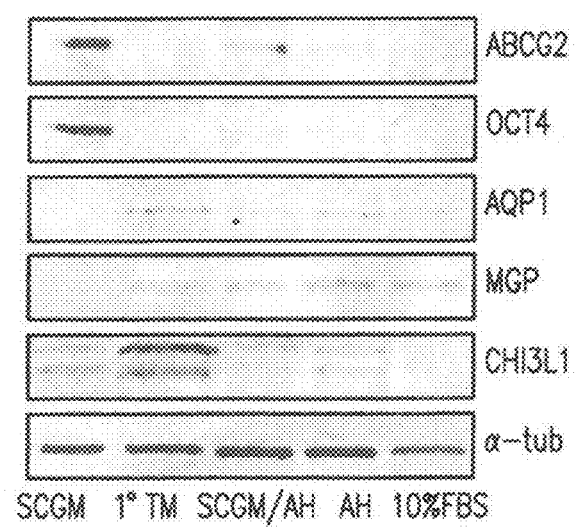

Western blotting (FIG. 15B) identified ABCG2 and OCT4 expression in clonal TMSC but not in primary TM cells. A low level of ABCG2 was detected in cells cultured in SCGM/AH but not in cells in AH or 10% FBS. AQP1 and MGP were expressed in primary TM cells and induced cells but not in TMSC. CHI3L1 appeared as a doublet migrating at ~39 kDa in primary and induced TM cells and weakly in TMSC. The lower molecular weight band may represent a glycosylation variant of the protein(28).

TM cells have phagocytic activity which eliminates debris, pigment, and other materials from the aqueous to maintain the outflow pathway (21, 29, 30). Phagocytic ability of the TMSC was assessed using fluorescently tagged *S. aureus* bioparticles comparing clonal TMSC, induced and primary TM cells (FIGS. 16A-16E). Ingested *S. aureus* bioparticles appear green. On average, 0.18 green particles per cell were ingested by TMSC in SCGM (FIG. 16F). In contrast, TMSC induced in SCGM/AH ingested 1.12 particles per cell; AH, 1.61; 10% FBS, 1.83, and primary TM cells had 2.11 particles per cell. ANOVA followed by Dunnett's test shows the increase in phagocytic activity by TSMC to be significant (p<0.0001) under all conditions; but none of the induced TSMC differed significantly from the activity of primary TM cells.

DISCUSSION

In this report we describe the isolation and characterization of a population of stem cells from human TM. These cells can be isolated as a side population by FACS or by clonal growth. In culture they present a homogeneous population displaying antigenic markers previously characterized for mesenchymal stem cells (ABCG2, CD73, CD90, CD166 and Bmi1) as well as expressing gene products associated with pluripotent stem cells (Notch1, OCT4). Their stem cell character was confirmed by the ability of these cells to display phenotypic properties of cells from several different developmental lineages (neural, adipose, cornea) under culture conditions known to induce differentiation of multipotent stem cells. These cells are capable of differentiating into TM cells with phagocytic function and expressing TM markers AQP1, MGP, CHI3L1 and TIMP3 in the presence of aqueous humor or 10% serum. All of these indicate that these cells represent a resident population of adult stem cells in the human TM.

These results confirm and extend conclusions of previous studies suggesting stem cells in human TM. Challa et al described 'novel' cells in primary TM cultures expressing MUC-1 and AnkG(15). Kelley et al confirmed the expression suggesting it might be associated with a stem cell population(14). Gonzalez et al found cultured TM cells capable of forming free-floating neurospheres, a function associated with neural stem cells(12). More recently, McGowan et al observed cells expressing Oct-3/4, nestin, telomerase, PAX6, and Sox2 in the peripheral endothelium and TM of human corneas(13).

The above data confirm the presence of a stem cell population in TM which expressed MUC1, AnkG, PAX6, and Oct4. Expression of these markers clearly distinguish TMSC from typical mesenchymal stem cells. PAX6 is a homeobox gene essential to ocular development and is present in some adult ocular tissues but not generally present in TM31. PAX6 is present in corneal stromal stem cells(17, 32) but is not expressed by mesenchymal stem cells(33). MUC1 is a cell surface mucin associated with breast and other epithelial cancers(34). AnkG was recently described as essential for production of new neurons in the brain(35) and was described with higher expression in Schwalbe's cells that have been postulated to be responsible for cell regeneration in the TM(15). The expression of these three genes in the TMSC, therefore, defines markers distinguishing these cells from bone marrow-derived mesenchymal stem cells.

Similarly, the ability to differentiate to functional TM cells is a novel and, at current time, unique property of this cell population. The observation that TMSC differentiate to TM cells in the presence of fetal bovine serum suggests that differentiation to TM is the default lineage for these cells, implying that they are indeed a specialized population of stem cells, not mesenchymal stem cells from the vasculature or other tissues. The identification of cells that naturally differentiate to TM in vitro can be useful as a research tool to better understand steps in the developmental lineage of these rare cells. The ability to expand the numbers of TMSC provides access to large number of homogeneous TM cells for study in vitro, a facility not previously available from such a small tissue.

The above data show that TMSC express characteristic TM proteins after induction. These markers have essential roles in TM function and help to establish that TMSC can reestablish primary TM functions maintaining aqueous outflow. The water channel aquaporin 1 (AQP1) has been detected in the TM in vivo(27) as well as in cultured human TM cells and plays an important role in modulation of aqueous outflow(5). Matrix Glaprotein (MGP) has the ability to function in the TM as a calcification inhibitor[36] and may be a key contributor to intraocular pressure homeostasis by regulating calcification and hardening of the TM(37). Aqueous humor contains chitinase 3-like 1 (CHI3L1) which has a protective role against inflammation, ECM remodeling and cell death in the outflow pathway(24). Myocilin expression in TM cells is induced upon treatment with dexamethasone, TGF-β or mechanical stretch and may lead to impaired outflow resistance(38). TM cells induced from TMSC with 10% serum also showed increased myocilin expression (FIG. 15). This may be a result of the steroid content of fetal bovine serum or simply reflect the difference in myocilin expression between TMSC and TM cells (as observed in FIG. 9).

TM cells have phagocytic activity that is essential in maintaining normal aqueous outflow. We report here that TMSC after induction demonstrated phagocytic function almost as strong as primary TM cells. These are important findings that provide a biological source of differentiated TM cells for stem cell-based therapy on glaucoma.

TABLE 3

| Antibody | Type | Source | Catalog# |
|---|---|---|---|
| ABCG2 | Mouse monoclonal | Chemicon | MAB4146 |
| Mucin1 | Mouse monoclonal | Santa Cruz | Sc-7313 |
| Ankynn GG | Mouse monoclonal | Santa Cruz | Sc-12719 |
| AQP1 | Rabbit polyclonal | Santa Cruz | Sc-20810 |
| MGP | Mouse monoclonal | Santa Cruz | SC-81546 |
| CHI3L1 | Goat polyclonal | R&D | AF2599 |
| TIMP3 | Mouse monoclonal | Santa Cruz | Sc-101578 |
| MYOC | Rabbit polyclonal | Santa Cruz | Sc-20976 |
| OCT4 | Rabbit polyclonal | Santa Cruz | Sc-9081 |
| Notch 1 | Mouse monoclonal | BD Pharmingen | 552466 |
| CD73 | PE-conjugated | eBioscience | 12-0731-81 |
| CD90 | Alex Fluor 6470-conjugated | Biolegend | 328115 |
| CD166 | FITC-conjugated | Biological | KO04-4 |
| Bmi1 | Mouse monoclonal | Millipore | 05-637 |
| Neurofilament | Mouse monoclonal | Sigma | N0142 |
| β-tubulin III | Mouse monoclonal | Chemicon | MAB1637 |
| GFAP | Mouse monoclonal | Chemicon | MAB360 |
| Keratan Sulfate | Mouse monoclonal | Kind gift from Dr. Bruce Katerson | |
| Keratocan | Goat polyclonal | Kind gift from Dr. Winston Kao | |
| α-tubulin | Mouse monoclonal | Sigma | T5168 |

TABLE 4

| Gene Name | DNA Sequence | | Seq. Id. No. |
|---|---|---|---|
| 18S Ribosomal RNA | Forward: | CCCTGTAATTGGAATGAGTCCAC | 45 |
| | Reverse: | GCTGGAATTACCGCGGCT | 46 |
| ABCG2 | Forward: | TGCAACATGTACTGGCGAAGA | 47 |
| | Reverse: | TCTTCCACAAGCCCCAGG | 48 |
| Pax6 | Forward: | CAATCAAAACGTGTCCAACG | 49 |
| | Reverse: | TAGCCAGGTTGCGAAGAACT | 50 |
| Notch1 | Forward: | AGTCTCTGCAGTGCTGGAAGTA | 51 |
| | Reverse: | CTTGCAGTACTGGTCGTACAGG | 52 |
| Muc1 (Mucin1) | Forward: | CCATTCCACTCCACTCAGGT | 53 |
| | Reverse: | CCACATGAGCTTCCACACAC | 54 |
| AnkG (AnkyrinG) | Forward: | CATTCCTCCACGCAAGTGTA | 55 |
| | Reverse: | GTGGGTTGGCCAGTTTATGT | 56 |
| AQP1 (Aquaporin1) | Forward: | CTGCACAGGCTTGCTGTATG | 57 |
| | Reverse: | TGTTCCTTGGGCTGCAACTA | 58 |
| MGP | Forward: | GCCGCCTTAGCGGTAGTAACTCTCTGCTGAGGGGAATATGA | 59 |
| | Reverse: | | 60 |
| CHI3L1 | Forward: | CCTTGACCGCTTCCTCTGTAGTGTTGAGCATGCCGTAGAG | 61 |
| | Reverse: | | 62 |
| MYOC (Myocilin) | Forward: | AAGCCCACCTACCCCTACAC | 63 |
| | Reverse: | TCCAGTGGCCTAGGCAGTAT | 64 |
| ELAM1 | Forward: | ACACCTCCACGGAAGCTATG | 65 |
| | Reverse: | AATTGCAACCAGGTGTGTGTA | 66 |
| MMP1 | Forward: | TGGACCTGGAGGAAATCTTG | 67 |
| | Reverse: | AGAATGGCCGAGTTCATGAG | 68 |
| Neurofilament | Forward: | GAGGAACACCAAGTGGGAGA | 69 |
| | Reverse: | CTCCTCCTCTTTGGCCTCTT | 70 |
| GFAP | Forward: | ACTACATCGCCCTCCACATC | 71 |
| | Reverse: | CAAAGGCACAGTTCCCAGAT | 72 |
| ap2 | Forward: | CATGGCCAAACCTAACATGA | 73 |
| | Reverse: | AATTCCTGCCCAGTATGAA | 74 |

TABLE 4-continued

| Gene Name | DNA Sequence | Seq. Id. No. |
|---|---|---|
| Leptin | Forward: TCCTGGATTCCTTTCCTTCA | 75 |
|  | Reverse: CAATCGAGGAGGGCAGAATA | 76 |
| KERA (keratocan) | Forward: ATCTGCAGCACCTTCACCTT | 77 |
|  | Reverse: CATTGGAATTGGTGGTTTGA | 78 |
| ALDH | Forward: CATTGGCACCTGGAACTACC | 79 |
|  | Reverse: GGCTTGAGGACCACTGAGTT | 80 |

The following is a list of references cited in Example 3.
1. Gupta D. *Glaucoma diagnosis and management*: Lippincott Williams & Wilkins; 2004.
2. Le A, Mukesh B N, McCarty C A, Taylor H R. Risk factors associated with the incidence of open-angle glaucoma: the visual impairment project. *Invest Ophthalmol Vis Sci* 2003; 44:3783-3789.
3. Levkovitch-Verbin H. Animal models of optic nerve diseases. *Eye (Lond)* 2004; 18:1066-1074.
4. Buller C, Johnson D H, Tschumper R C. Human trabecular meshwork phagocytosis. Observations in an organ culture system. *Investigative ophthalmology & visual science* 1990; 31:2156-2163.
5. Stamer W D, Seftor R E, Snyder R W, Regan J W. Cultured human trabecular meshwork cells express aquaporin-1 water channels. *Curr Eye Res* 1995; 14:1095-1100.
6. Alvarado J, Murphy C, Polansky J, Juster R. Age-related changes in trabecular meshwork cellularity. *Invest Ophthalmol Vis Sci* 1981; 21:714-727.
7. He Y, Leung K W, Zhang Y H, et al. Mitochondrial complex I defect induces ROS release and degeneration in trabecular meshwork cells of POAG patients: protection by antioxidants. *Invest Ophthalmol Vis Sci* 2008; 49:1447-1458.
8. Lutjen-Drecoll E. Morphological changes in glaucomatous eyes and the role of TGFbeta2 for the pathogenesis of the disease. *Exp Eye Res* 2005; 81:1-4.
9. Alvarado J, Murphy C, Juster R. Trabecular meshwork cellularity in primary open-angle glaucoma and nonglaucomatous normals. *Ophthalmology* 1984; 91:564-579.
10. Daley G Q, Scadden D T. Prospects for stem cell-based therapy. *Cell* 2008; 132:544-548.
11. Verfaillie C M. Adult stem cells: assessing the case for pluripotency. *Trends Cell Biol* 2002; 12:502-508.
12. Gonzalez P, Epstein D L, Luna C, Liton P B. Characterization of free-floating spheres from human trabecular meshwork (HTM) cell culture in vitro. *Exp Eye Res* 2006; 82:959-967.
13. McGowan S L, Edelhauser H F, Pfister R R, Whikehart D R. Stem cell markers in the human posterior limbus and corneal endothelium of unwounded and wounded corneas. *Mol Vis* 2007; 13:1984-2000.
14. Kelley M J, Rose A Y, Keller K E, Hessle H, Samples J R, Acott T S. Stem cells in the trabecular meshwork: present and future promises. *Exp Eye Res* 2009; 88:747-751.
15. Challa P, Gonzalez P, Liton P B, Caballero M, Epstein D L. Gene expression profile in a novel cell type in primary cultures of human trabecular meshwork. *Invest Ophthalmol Vis* 2003; 44:E-Abstract 3164.
16. Mimura T, Joyce N C. Replication competence and senescence in central and peripheral human corneal endothelium. *Investigative ophthalmology & visual science* 2006; 47:1387-1396.
17. Du Y, Funderburgh M L, Mann M M, SundarRaj N, Funderburgh J L. Multipotent stem cells in human corneal stroma. *Stem Cells* 2005; 23:1266-1275.
18. Telford W G, Bradford J, Godfrey W, Robey R W, Bates S E. Side population analysis using a violet-excited cell-permeable DNA binding dye. *Stem Cells* 2007; 25:1029-1036.
19. Du Y, Sundarraj N, Funderburgh M L, Harvey S A, Birk D E, Funderburgh J L. Secretion and organization of a cornea-like tissue in vitro by stem cells from human corneal stroma. *Invest Ophthalmol Vis Sci* 2007; 48:5038-5045.
20. Patel A N, Park E, Kuzman M, Benetti F, Silva F J, Allickson J G. Multipotent menstrual blood stromal stem cells: isolation, characterization, and differentiation. *Cell Transplant* 2008; 17:303-311.
21. Zhang X, Ognibene C M, Clark A F, Yorio T. Dexamethasone inhibition of trabecular meshwork cell phagocytosis and its modulation by glucocorticoid receptor beta. *Exp Eye Res* 2007; 84:275-284.
22. Du Y, Carlson E C, Funderburgh M L, et al. Stem cell therapy restores transparency to defective murine corneas. *Stem Cells* 2009; 27:1635-1642.
23. Goodell M A, Brose K, Paradis G, Conner A S, Mulligan R C. Isolation and functional properties of murine hematopoietic stem cells that are replicating in vivo. *J Exp Med* 1996; 183:1797-1806.
24. Liton P B L Y, Luna C, et al. Identification of genes differentially expressed by Chitinase 3-like 1 in human trabecular meshwork cells. *IOVS* 2009; 50:4859.
25. Liu C Y, Birk D E, Hassell J R, Kane B, Kao W W. Keratocan-deficient mice display alterations in corneal structure. *J Biol Chem* 2003; 278:21672-21677.
26. Ruiz-Ederra J, Verkman A S. Aquaporin-1-facilitated keratocyte migration in cell culture and in vivo corneal wound healing models. *Exp Eye Res* 2009; 89:159-165.
27. Stamer W D, Snyder R W, Smith B L, Agre P, Regan J W. Localization of aquaporin CHIP in the human eye: implications in the pathogenesis of glaucoma and other disorders of ocular fluid balance. *Invest Ophthalmol Vis Sci* 1994; 35:3867-3872.
28. Recklies A D, Ling H, White C, Bernier S M. Inflammatory cytokines induce production of CHI3L1 by articular chondrocytes. *J Biol Chem* 2005; 280:41213-41221.
29. Bill A. Editorial: The drainage of aqueous humor. *Invest Ophthalmol* 1975; 14:1-3.
30. Johnson D H, Richardson T M, Epstein D L. Trabecular meshwork recovery after phagocytic challenge. *Curr Eye Res* 1989; 8:1121-1130.
31. Collinson J M, Quinn J C, Hill R E, West J D. The roles of Pax6 in the cornea, retina, and olfactory epithelium of the developing mouse embryo. *Dev Biol* 2003; 255:303-312.
32. Funderburgh M L, Du Y, Mann M M, SundarRaj N, Funderburgh J L. PAX6 expression identifies progenitor cells for corneal keratocytes. *Faseb J* 2005; 19:1371-1373.
33. Nagai A, Kim W K, Lee H J, et al. Multilineage potential of stable human mesenchymal stem cell line derived from fetal marrow. *PLoS One* 2007; 2:e1272.
34. Mukhopadhyay P, Chakraborty S, Ponnusamy M P, Lakshmanan I, Jain M, Batra S K. Mucins in the pathogenesis of breast cancer: implications in diagnosis, prognosis and therapy. *Biochim Biophys Acta* 2011; 1815:224-240.

35. Paez-Gonzalez P, Abdi K, Luciano D, et al Ank3-dependent SVZ niche assembly is required for the continued production of new neurons. *Neuron* 2011; 71:61-75.
36. Xue W, Comes N, Borras T. Presence of an established calcification marker in trabecular meshwork tissue of glaucoma donors. *Investigative ophthalmology & visual science* 2007; 48:3184-3194.
37. Vittitow J, Borras T. Genes expressed in the human trabecular meshwork during pressure-induced homeostatic response. *J Cell Physiol* 2004; 201:126-137.
38. Tamm E R. Myocilin and glaucoma: facts and ideas. *Prog Retin Eye Res* 2002; 21:395-428.

All description herein relating to compositions or methods of treatment also should be construed to define "uses" of the invention. For example, the invention includes use of a source of salicylic acid for the treatment of conditions identified herein or achieving a therapeutic goal identified herein (e.g., lowing blood glucose in a human in need thereof). Likewise, the invention also includes use of a source of salicylic acid for manufacture of a medicament for such treatment purposes.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. With respect to aspects described as a range, all subranges and individual values are specifically contemplated.

Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention. Additional features and variations of the invention will be apparent to those skilled in the art front the entirety of this application, and all such features are intended as aspects of the invention.

Various references are cited herein which are hereby incorporated by reference in their entireties.

What is claimed:

1. A method of decreasing intraocular pressure in an eye, comprising administering into an eye of a subject in need thereof a composition comprising a therapeutic amount of an isolated population of multipotent stem cells and a pharmaceutically acceptable carrier, diluent, or excipient; wherein the administered multipotent stem cells differentiate, in the eye, into trabecular meshwork cells and thereby increase cell density in the trabecular meshwork and decrease the intraocular pressure in the eye.

2. The method of claim 1, wherein the medical condition is glaucoma.

3. The method of claim 1, wherein the composition is injected into the eye of the subject.

4. The method of claim 3, wherein the composition is injected into the TM or Schlemm's canal of the eye.

5. The method of claim 1, wherein the multipotent stem cells in the composition are comprised, in releasable form, in a matrix or capsule and the matrix or capsule is implanted into the anterior chamber, trabecular meshwork, or Schlemm's canal of the subject such that following administration, multipotent stem cells are released at that location and locate in the trabecular meshwork, increasing its cell density.

6. A method of increasing cell density in a trabecular meshwork (TM) of an eye, comprising administering into an eye of a subject in need thereof a therapeutic amount of a composition comprising an isolated population of multipotent stem cells; wherein the administered multipotent stem cells differentiate, in the eye, into trabecular meshwork cells and thereby increase cell density in the TM.

7. The method of claim 6, wherein the medical condition is glaucoma.

8. The method of claim 6, wherein the composition is injected into the eye of the subject.

9. The method of claim 8, wherein the composition is injected into the TM or Schlemm's canal of the eye.

10. The method of claim 6, wherein the multipotent stem cells in the composition are comprised, in releasable form, in a matrix or capsule and the matrix or capsule is implanted into the anterior chamber, trabecular meshwork, or Schlemm's canal of the subject such that following implantation multipotent stem cells are released at that location and locate in the trabecular meshwork, increasing its cell density.

11. A method of increasing outflow of aqueous humor from an eye, comprising administering into an eye of a subject in need thereof a therapeutic amount of a composition comprising an isolated population of multipotent stem cells and a pharmaceutically acceptable carrier, diluent, or excipient; wherein the administered multipotent stem cells differentiate, in the eye, into trabecular meshwork cells and thereby increase cell density in the trabecular meshwork and increase the outflow of aqueous humor.

12. The method of claim 11, wherein the medical condition is glaucoma.

13. The method of claim 11, wherein the composition is injected into the eye of the subject.

14. The method of claim 13, wherein the composition is injected into the TM or Schlemm's canal of the eye.

15. The method of claim 11, wherein the multipotent stem cells in the composition are comprised, in releasable form, in a matrix or capsule and the matrix or capsule is implanted into the anterior chamber, trabecular meshwork, or Schlemm's canal of the subject such that following implantation multipotent stem cells are released at that location and locate in the trabecular meshwork, increasing its cell density.

* * * * *